United States Patent
Purwar et al.

(10) Patent No.: US 12,331,114 B2
(45) Date of Patent: Jun. 17, 2025

(54) HUMANIZED ANTI-CD19 CHIMERIC ANTIGEN RECEPTOR, ITS NUCLEIC ACID SEQUENCE AND ITS PREPARATION

(71) Applicant: INDIAN INSTITUTE OF TECHNOLOGY BOMBAY, Mumbai (IN)

(72) Inventors: Rahul Purwar, Mumbai (IN); Alka Dwivedi, Mumbai (IN); Atharva Karulkar, Mumbai (IN); Srisathya Srinivasan, Mumbai (IN)

(73) Assignee: INDIAN INSTITUTE OF TECHNOLOGY BOMBAY, Mumbai (IN)

( * ) Notice: Subject to any disclaimer, the term of this patent is extended or adjusted under 35 U.S.C. 154(b) by 282 days.

(21) Appl. No.: 16/969,788

(22) PCT Filed: Feb. 12, 2019

(86) PCT No.: PCT/IN2019/050111
§ 371 (c)(1),
(2) Date: Aug. 13, 2020

(87) PCT Pub. No.: WO2019/159193
PCT Pub. Date: Aug. 22, 2019

(65) Prior Publication Data
US 2021/0002366 A1 Jan. 7, 2021

(30) Foreign Application Priority Data
Feb. 13, 2018 (IN) .............................. 201821005458

(51) Int. Cl.
| | |
|---|---|
| *C07K 16/28* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C12N 15/86* | (2006.01) |

(52) U.S. Cl.
CPC .......... *C07K 16/2803* (2013.01); *A61K 40/11* (2025.01); *A61K 40/31* (2025.01); *A61K 40/4211* (2025.01); *A61P 35/00* (2018.01); *C07K 14/7051* (2013.01); *C07K 14/70517* (2013.01); *C07K 14/70578* (2013.01); *C12N 15/86* (2013.01); *A61K 2239/48* (2023.05); *C07K 2317/24* (2013.01); *C07K 2317/53* (2013.01); *C07K 2317/56* (2013.01); *C07K 2317/565* (2013.01); *C07K 2317/567* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

2014/0271635 A1* 9/2014 Brogdon .......... C07K 14/70503
536/23.53

OTHER PUBLICATIONS

June et al., N Engl J Med. Jul. 5, 2018;379(1):64-73. doi: 10.1056/NEJMra1706169. PMID: 29972754 PMCID: PMC7433347.*
Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Edwards et al., J Mol Biol. Nov. 14, 2003;334(1): 103-18.*
Goel et al., J Immunol. Dec. 15, 2004; 173(12):7358-67.*
Llyod et al., Protein Eng Des Sel. Mar. 2009;22(3):159-68. doi: 10.1093/protein/gzn058. Epub Oct. 29, 2008.*
Lescar, et al. Journal of Biological Chemistry 270.30 (1995): 18067-18076.*
Kanyavuz et al., Nat Rev Immunol. Jun. 2019;19(6):355-368. doi: 10.1038/S41577-019-0126-7.*
June et al., Science. Mar. 23, 2018;359(6382):1361-1365. doi: 10.1126/science.aar6711. PMID: 29567707.*

* cited by examiner

*Primary Examiner* — Michael Szperka
(74) *Attorney, Agent, or Firm* — Rivka Friedman

(57) ABSTRACT

The present invention relates to novel humanized anti-CD19chimeric antigen receptor containing an optimized anti-CD19 binding domain effective against the treatment of disease associated with expression of the Cluster of Differentiation 19 protein (CD19), and to a nucleic acid molecule encoding the humanized CAR. The invention also encompasses a process forth preparation of the CAR, composition containing the CAR, vectors containing the polynucleotide encoding the CAR and cells expressing the Carat their surface, in particular for their use in immunotherapy.

16 Claims, 6 Drawing Sheets
Specification includes a Sequence Listing.

SEQUENCE LISTING

<160> NUMBER OF SEQ ID NOS: 66

<210> SEQ ID NO 1
<211> LENGTH: 119
<212> TYPE: PRT
<213> ORGANISM: Artificial Sequence
<220> FEATURE:
<223> OTHER INFORMATION: Synthesized - Humanized anti-CD19 binding
      domain heavy chain variable region

<400> SEQUENCE: 1

```
Gln Val Gln Leu Gln Gln Trp Gly Ala Gly Leu Leu Lys Pro Ser Glu
1               5                   10                  15

Thr Leu Ser Leu Thr Cys Ala Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Ser Ser Ser Leu Lys
    50                  55                  60

Ser Val Thr Ile Ile Lys Asp Thr Ser Lys Asn Gln Phe Phe Leu Lys
65                  70                  75                  80

Leu Ser Ser Val Thr Ala Ala Asp Thr Ala Val Tyr Tyr Cys Ala Arg
                85                  90                  95

His Tyr Tyr Tyr Gly Gly Ser Tyr Ala Met Asp Tyr Trp Gly Gln Gly
            100                 105                 110

Thr Thr Val Thr Val Ser Ser
        115
```

<210> SEQ ID NO 2
<211> LENGTH: 119
<212> TYPE: PRT
<213> ORGANISM: Artificial Sequence
<220> FEATURE:
<223> OTHER INFORMATION: Synthesized - Humanized anti-CD19 binding
      domain heavy chain variable region

<400> SEQUENCE: 2

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Ser Ser Ser Leu Lys
    50                  55                  60

Ser Val Thr Ile Ser Val Asp Thr Ser Lys Asn Gln Phe Ser Leu Lys
65                  70                  75                  80

Leu Ser Ser Val Thr Ala Ala Asp Thr Ala Val Tyr Tyr Cys Ala Arg
                85                  90                  95

His Tyr Tyr Tyr Gly Gly Ser Tyr Ala Met Asp Tyr Trp Gly Gln Gly
            100                 105                 110

Thr Thr Val Thr Val Ser Ser
        115
```

<210> SEQ ID NO 3
<211> LENGTH: 107
<212> TYPE: PRT

```
<213> ORGANISM: Artificial Sequence
<220> FEATURE:
<223> OTHER INFORMATION: Synthesized - Humanized anti-CD19 binding
      domain light chain variable region

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Val Glu Ile Lys
            100                 105

<210> SEQ ID NO 4
<211> LENGTH: 25
<212> TYPE: PRT
<213> ORGANISM: Artificial Sequence
<220> FEATURE:
<223> OTHER INFORMATION: Synthesized - Humanized anti-CD19 binding
      domain HCVR framework region 1

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Val Ser
            20                  25

<210> SEQ ID NO 5
<211> LENGTH: 25
<212> TYPE: PRT
<213> ORGANISM: Artificial Sequence
<220> FEATURE:
<223> OTHER INFORMATION: Synthesized - Humanized anti-CD19 binding
      domain HCVR framework region 1

<400> SEQUENCE: 5

Gln Val Gln Leu Gln Gln Trp Gly Ala Gly Leu Leu Lys Pro Ser Glu
1               5                   10                  15

Thr Leu Ser Leu Thr Cys Ala Val Tyr
            20                  25

<210> SEQ ID NO 6
<211> LENGTH: 10
<212> TYPE: PRT
<213> ORGANISM: Artificial Sequence
<220> FEATURE:
<223> OTHER INFORMATION: Synthesized - Humanized anti-CD19 binding
      domain HCVR CDR 1

<400> SEQUENCE: 6

Gly Val Ser Leu Pro Asp Tyr Gly Val Ser
1               5                   10

<210> SEQ ID NO 7
<211> LENGTH: 14
```

```
<212> TYPE: PRT
<213> ORGANISM: Artificial Sequence
<220> FEATURE:
<223> OTHER INFORMATION: Synthesized - Humanized anti-CD19 binding
      domain HCVR framework region 2

<400> SEQUENCE: 7

Trp Ile Arg Gln Pro Pro Gly Lys Gly Leu Glu Trp Leu Gly
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthesized - Humanized anti-CD19 binding
      domain HC CDR2

<400> SEQUENCE: 8

Val Ile Trp Gly Ser Glu Thr Thr Tyr Tyr Ser Ser Ser Leu Lys Ser
1               5                   10                  15

<210> SEQ ID NO 9
<211> LENGTH: 31
<212> TYPE: PRT
<213> ORGANISM: Artificial Sequence
<220> FEATURE:
<223> OTHER INFORMATION: Synthesized - Humanized anti-CD19 binding
      domain HCVR framework region 3

<400> SEQUENCE: 9

Val Thr Ile Ile Lys Asp Thr Ser Lys Asn Gln Phe Phe Leu Lys Leu
1               5                   10                  15

Ser Ser Val Thr Ala Ala Asp Thr Ala Val Tyr Tyr Cys Ala Arg
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthesized - Humanized anti-CD19 binding
      domain HCVR framework region 3

<400> SEQUENCE: 10

Val Thr Ile Ser Val Asp Thr Ser Lys Asn Gln Phe Ser Leu Lys Leu
1               5                   10                  15

Ser Ser Val Thr Ala Ala Asp Thr Ala Val Tyr Tyr Cys Ala Arg
            20                  25                  30

<210> SEQ ID NO 11
<211> LENGTH: 12
<212> TYPE: PRT
<213> ORGANISM: Artificial Sequence
<220> FEATURE:
<223> OTHER INFORMATION: Synthesized - Humanized anti-CD19 binding
      domain HC CDR3

<400> SEQUENCE: 11

His Tyr Tyr Tyr Gly Gly Ser Tyr Ala Met Asp Tyr
1               5                   10

<210> SEQ ID NO 12
<211> LENGTH: 11
<212> TYPE: PRT
<213> ORGANISM: Artificial Sequence
<220> FEATURE:
```

<223> OTHER INFORMATION: Synthesized - Humanized anti-CD19 binding
      domain HCVR framework region 4

<400> SEQUENCE: 12

Trp Gly Gln Gly Thr Thr Val Thr Val Ser Ser
1               5                   10

<210> SEQ ID NO 13
<211> LENGTH: 23
<212> TYPE: PRT
<213> ORGANISM: Artificial Sequence
<220> FEATURE:
<223> OTHER INFORMATION: Synthesized - Humanized anti-CD19 binding
      domain LCVR framework region 1

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 14
<211> LENGTH: 11
<212> TYPE: PRT
<213> ORGANISM: Artificial Sequence
<220> FEATURE:
<223> OTHER INFORMATION: Synthesized - Humanized anti-CD19 binding
      domain LC CDR1

<400> SEQUENCE: 14

Arg Ala Ser Gln Asp Ile Ser Lys Tyr Leu Asn
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthesized - Humanized anti-CD19 binding
      domain LCVR framework region 2

<400> SEQUENCE: 15

Trp Tyr Gln Gln Lys Pro Gly Lys Ala Pro Lys Leu Leu Ile Tyr
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Synthesized - Humanized anti-CD19 binding
      domain LC CDR2

<400> SEQUENCE: 16

His Thr Ser Arg Leu His Ser Gly
1               5

<210> SEQ ID NO 17
<211> LENGTH: 31
<212> TYPE: PRT
<213> ORGANISM: Artificial Sequence
<220> FEATURE:
<223> OTHER INFORMATION: Synthesized - Humanized anti-CD19 binding
      domain LCVR framework region 3

<400> SEQUENCE: 17

Val Pro Ser Arg Phe Ser Gly Ser Gly Ser Gly Thr Asp Phe Thr Phe

```
                1               5                  10                 15
Thr Ile Ser Ser Leu Gln Pro Glu Asp Ile Ala Thr Tyr Tyr Cys
            20                  25                 30

<210> SEQ ID NO 18
<211> LENGTH: 9
<212> TYPE: PRT
<213> ORGANISM: Artificial Sequence
<220> FEATURE:
<223> OTHER INFORMATION: Synthesized - Humanized anti-CD19 binding
      domain LC CDR3

<400> SEQUENCE: 18

Gln Gln Gly Asn Thr Leu Pro Tyr Thr
1               5

<210> SEQ ID NO 19
<211> LENGTH: 10
<212> TYPE: PRT
<213> ORGANISM: Artificial Sequence
<220> FEATURE:
<223> OTHER INFORMATION: Synthesized - Humanized anti-CD19 binding
      domain LCVR framework region 4

<400> SEQUENCE: 19

Phe Gly Gly Gly Thr Lys Val Glu Ile Lys
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Synthesized - VH-VL linker sequence

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 24
<212> TYPE: PRT
<213> ORGANISM: Artificial Sequence
<220> FEATURE:
<223> OTHER INFORMATION: Synthesized - CD8 alpha transmembrane domain

<400> SEQUENCE: 21

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 22
<211> LENGTH: 45
<212> TYPE: PRT
<213> ORGANISM: Artificial Sequence
<220> FEATURE:
<223> OTHER INFORMATION: Synthesized - CD8 alpha hinge region

<400> SEQUENCE: 22

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
```

<210> SEQ ID NO 23
<211> LENGTH: 42
<212> TYPE: PRT
<213> ORGANISM: Artificial Sequence
<220> FEATURE:
<223> OTHER INFORMATION: Synthesized - 4-1BB costimulatory domain

<400> SEQUENCE: 23

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 24
<211> LENGTH: 112
<212> TYPE: PRT
<213> ORGANISM: Artificial Sequence
<220> FEATURE:
<223> OTHER INFORMATION: Synthesized - CD3 zeta signaling domain

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
<211> LENGTH: 485
<212> TYPE: PRT
<213> ORGANISM: Artificial Sequence
<220> FEATURE:
<223> OTHER INFORMATION: Synthesized - Humanized anti-CD19 CAR amino
      acid sequence

<400> SEQUENCE: 25

Met Ala Leu Pro Val Thr Ala Leu Leu Leu Pro Leu Ala Leu Leu Leu
1               5                   10                  15

His Ala Ala Arg Pro Gln Val Gln Leu Gln Gln Trp Gly Ala Gly Leu
            20                  25                  30

Leu Lys Pro Ser Glu Thr Leu Ser Leu Thr Cys Ala Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Leu Gly Val Ile Trp Gly Ser Glu Thr Thr Tyr Tyr
65                  70                  75                  80

Ser Ser Ser Leu Lys Ser Val Thr Ile Ile Lys Asp Thr Ser Lys Asn

```
                        85                  90                  95
Gln Phe Leu Lys Leu Ser Ser Val Thr Ala Ala Asp Thr Ala Val
            100                 105                 110
Tyr Tyr Cys Ala Arg His Tyr Tyr Gly Gly Ser Tyr Ala Met Asp
            115                 120                 125
Tyr Trp Gly Gln Gly Thr Thr Val Thr Val Ser Ser Gly Gly Gly
            130                 135                 140
Ser Gly Gly Gly Ser Gly Gly Gly Ser Asp Ile Gln Met Thr
145                 150                 155                 160
Gln Ser Pro Ser Ser Leu Ser Ala Ser Val Gly Asp Arg Val Thr Ile
            165                 170                 175
Thr Cys Arg Ala Ser Gln Asp Ile Ser Lys Tyr Leu Asn Trp Tyr Gln
            180                 185                 190
Gln Lys Pro Gly Lys Ala Pro Lys Leu Leu Ile Tyr His Thr Ser Arg
            195                 200                 205
Leu His Ser Gly Val Pro Ser Arg Phe Ser Gly Ser Gly Ser Gly Thr
            210                 215                 220
Asp Phe Thr Phe Thr Ile Ser Ser Leu Gln Pro Glu Asp Ile Ala Thr
225                 230                 235                 240
Tyr Tyr Cys Gln Gln Gly Asn Thr Leu Pro Tyr Thr Phe Gly Gly Gly
            245                 250                 255
Thr Lys Val Glu Ile Lys Thr Thr Thr Pro Ala Pro Arg Pro Pro Thr
            260                 265                 270
Pro Ala Pro Thr Ile Ala Ser Gln Pro Leu Ser Leu Arg Pro Glu Ala
            275                 280                 285
Cys Arg Pro Ala Ala Gly Gly Ala Val His Thr Arg Gly Leu Asp Phe
            290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Lys Arg Gly Arg Lys
            325                 330                 335
Lys Leu Leu Tyr Ile Phe Lys Gln Pro Phe Met Arg Pro Val Gln Thr
            340                 345                 350
Thr Gln Glu Glu Asp Gly Cys Ser Cys Arg Phe Pro Glu Glu Glu Glu
            355                 360                 365
Gly Gly Cys Glu Leu Arg Val Lys Phe Ser Arg Ser Ala Asp Ala Pro
            370                 375                 380
Ala Tyr Gln Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
            405                 410                 415
Glu Met Gly Gly Lys Pro Arg Arg Lys Asn Pro Gln Glu Gly Leu Tyr
            420                 425                 430
Asn Glu Leu Gln Lys Asp Lys Met Ala Glu Ala Tyr Ser Glu Ile Gly
            435                 440                 445
Met Lys Gly Glu Arg Arg Arg Gly Lys Gly His Asp Gly Leu Tyr Gln
            450                 455                 460
Gly Leu Ser Thr Ala Thr Lys Asp Thr Tyr Asp Ala Leu His Met Gln
465                 470                 475                 480
Ala Leu Pro Pro Arg
            485

<210> SEQ ID NO 26
```

<211> LENGTH: 1458
<212> TYPE: DNA
<213> ORGANISM: Artificial Sequence
<220> FEATURE:
<223> OTHER INFORMATION: Synthesized - Humanized anti-CD19 CAR
      nucleotide sequence

<400> SEQUENCE: 26

```
atggccctgc ctgtgacagc tctgctgctg cctcttgctc tgcttctgca tgctgctaga    60
cctcaggttc agctgcagca atggggagcc ggactgctga agccttctga cactctgtct   120
ctgacctgtg ccgtcagcgg agtgtctctg cctgattacg gcgtgtcctg gatcagacag   180
cctcctggca aggactgga atggctggga gtgatctggg gcagcgagac aacctactac   240
agcagcagcc tgaagtccgt gaccatcatc aaggacacca gcaagaacca gttcttcctg   300
aagctgagca gcgtgacagc cgccgataca gccgtgtact actgcgccag acactactac   360
tacggcggca gctacgccat ggattattgg ggccagggca ccacagtgac agtttctagc   420
ggaggcggag aagtggtgg cggaggttct ggcggcggag atctgatat ccagatgaca   480
cagagcccta gcagcctgtc tgcctctgtg ggcgatagag tgaccattac tgcagagcc   540
agccaggaca tctccaagta cctgaactgg tatcagcaga agcccggcaa ggcccctaag   600
ctgctgatct accacacaag cagactgcac agcggcgtgc caagcagatt ttctggcagc   660
ggctctggca ccgacttcac cttcaccatt tctagcctgc agcctgagga tatcgccacc   720
tactattgcc agcagggcaa caccctgcct tacacctttg gcggaggcac caaggtggaa   780
atcaagacca ccacaccagc tcctcggcct ccaactcctg ctcctacaat tgcctctcag   840
cctctgagcc tgaggcctga agcttgtaga cctgctgctg gcggagccgt gcataccaga   900
ggactggatt tcgcctgcga catctacatt tgggccctc tggctggaac atgtggcgtg   960
ctgctgctct ccctggtcat caccctgtac tgcaagcggg gcagaaagaa gctgctgtac  1020
atcttcaagc agcccttcat gcggcccgtg cagacaacac aagaggaaga tggctgctcc  1080
tgcagattcc ccgaggaaga agaaggcggc tgcgagctga gagtgaagtt ctccagatct  1140
gccgacgctc ctgcctatca gcagggccag aatcagctgt acaacgagct gaatctgggg  1200
cgcagagaag agtacgacgt gctggacaag agaaggggca gagatcctga tgggcggc   1260
aagcccagac ggaagaatcc tcaagagggc ctgtataatg agctgcagaa agacaagatg  1320
gccgaggcct acagcgagat cggaatgaag ggcgaacgca agaggcaa gggccacgat  1380
ggactgtatc agggcctgag cacagccacc aaggatacct atgatgccct gcacatgcag  1440
gccctgccac ctagataa                                                1458
```

<210> SEQ ID NO 27
<211> LENGTH: 485
<212> TYPE: PRT
<213> ORGANISM: Artificial Sequence
<220> FEATURE:
<223> OTHER INFORMATION: Synthesized - Humanized anti-CD19 CAR amino
      acid sequence

<400> SEQUENCE: 27

Met Ala Leu Pro Val Thr Ala Leu Leu Leu Pro Leu Ala Leu Leu Leu
1               5                   10                  15

His Ala Ala Arg Pro Gln Val Gln Leu Gln Gln Trp Gly Ala Gly Leu
            20                  25                  30

Leu Lys Pro Ser Glu Thr Leu Ser Leu Thr Cys Ala Val Tyr Gly Val
        35                  40                  45

-continued

```
Ser Leu Pro Asp Tyr Gly Val Ser Trp Ile Arg Gln Pro Pro Gly Lys
    50              55                  60
Gly Leu Glu Trp Leu Gly Val Ile Trp Gly Ser Glu Thr Thr Tyr Tyr
 65              70                  75                  80
Ser Ser Ser Leu Lys Ser Val Thr Ile Ser Val Asp Thr Ser Lys Asn
                 85                  90                  95
Gln Phe Ser Leu Lys Leu Ser Ser Val Thr Ala Ala Asp Thr Ala Val
                100                 105                 110
Tyr Tyr Cys Ala Arg His Tyr Tyr Gly Gly Ser Tyr Ala Met Asp
            115                 120                 125
Tyr Trp Gly Gln Gly Thr Thr Val Thr Val Ser Ser Gly Gly Gly Gly
    130                 135                 140
Ser Gly Gly Gly Gly Ser Gly Gly Gly Gly Ser Asp Ile Gln Met Thr
145                 150                 155                 160
Gln Ser Pro Ser Ser Leu Ser Ala Ser Val Gly Asp Arg Val Thr Ile
                165                 170                 175
Thr Cys Arg Ala Ser Gln Asp Ile Ser Lys Tyr Leu Asn Trp Tyr Gln
            180                 185                 190
Gln Lys Pro Gly Lys Ala Pro Lys Leu Leu Ile Tyr His Thr Ser Arg
        195                 200                 205
Leu His Ser Gly Val Pro Ser Arg Phe Ser Gly Ser Gly Ser Gly Thr
    210                 215                 220
Asp Phe Thr Phe Thr Ile Ser Ser Leu Gln Pro Glu Asp Ile Ala Thr
225                 230                 235                 240
Tyr Tyr Cys Gln Gln Gly Asn Thr Leu Pro Tyr Thr Phe Gly Gly Gly
                245                 250                 255
Thr Lys Val Glu Ile Lys Thr Thr Thr Pro Ala Pro Arg Pro Pro Thr
            260                 265                 270
Pro Ala Pro Thr Ile Ala Ser Gln Pro Leu Ser Leu Arg Pro Glu Ala
        275                 280                 285
Cys Arg Pro Ala Ala Gly Gly Ala Val His Thr Arg Gly Leu Asp Phe
    290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Lys Arg Gly Arg Lys
                325                 330                 335
Lys Leu Leu Tyr Ile Phe Lys Gln Pro Phe Met Arg Pro Val Gln Thr
            340                 345                 350
Thr Gln Glu Glu Asp Gly Cys Ser Cys Arg Phe Pro Glu Glu Glu Glu
        355                 360                 365
Gly Gly Cys Glu Leu Arg Val Lys Phe Ser Arg Ser Ala Asp Ala Pro
    370                 375                 380
Ala Tyr Gln Gln Gly Gln Asn Gln Leu Tyr Asn Glu Leu Asn Leu Gly
385                 390                 395                 400
Arg Arg Glu Glu Tyr Asp Val Leu Asp Lys Arg Gly Arg Asp Pro
                405                 410                 415
Glu Met Gly Gly Lys Pro Arg Arg Lys Asn Pro Gln Glu Gly Leu Tyr
            420                 425                 430
Asn Glu Leu Gln Lys Asp Lys Met Ala Glu Ala Tyr Ser Glu Ile Gly
        435                 440                 445
Met Lys Gly Glu Arg Arg Arg Gly Lys Gly His Asp Gly Leu Tyr Gln
    450                 455                 460
Gly Leu Ser Thr Ala Thr Lys Asp Thr Tyr Asp Ala Leu His Met Gln
```

Ala Leu Pro Pro Arg
            485

<210> SEQ ID NO 28
<211> LENGTH: 1461
<212> TYPE: DNA
<213> ORGANISM: Artificial Sequence
<220> FEATURE:
<223> OTHER INFORMATION: Synthesized - Humanized anti-CD19 CAR
      nucleotide sequence

<400> SEQUENCE: 28

```
atggccctgc ctgtgacagc tctgctgctg cctcttgctc tgcttctgca tgccgccaga      60
cctgaagtga agctgcaaga gtctggacct ggactggtgg cccctttctca gtctctgtct     120 gtgacctgta ccgtcagcgg agtgtctctg cctgattacg gcgtgtcctg gatcagacag     180
cctcctagaa aaggcctgga atggctgggc gtgatctggg gcagcgagac aacctactac     240
aacagcgccc tgaagtcccg gctgaccatc atcaaggaca cagcaagag ccaggtgttc      300 ctgaagatga acagcctgca gaccgacgac accgccatct actactgcgc caagcactac     360
tactacggcg gcagctacgc catggattat tggggccagg gcaccagcgt gacagtttct     420
tctggtggcg gaggatctgg cggaggtgga agcggcggag cggatctga tatccagatg      480 acccagacca aagcagcct gtctgcctct ctgggcgata gagtgaccat cagctgtaga     540
gccagccagg acatctccaa gtacctgaac tggtatcagc agaaaccga cggcaccgtg     600 aaactgctga tctaccacac cagcagactg cactctggcg tgccaagcag attttctggc     660
agcggctctg gcaccgacta cagcctgaca atcagcaacc tggaacaaga ggatatcgct     720
acctacttct gccagcaagg caacaccctg ccttacacct ttggcggagg caccaagctg     780
gaaatcacca ccacaacacc cgctcctaga ccacctacac cagctcctac aatcgccagc     840
cagcctctgt ctctgaggcc tgaagcttgt agacctgctg ctgcggagc cgtgcatacc     900 agaggactgg atttcgcctg cgacatctac atttgggccc ctctggctgg aacatgtggc     960
gtgctgctgc tgagcctggt catcaccctg tattgcaagc ggggcagaaa gaagctgctc    1020
tacatcttca gcagcccctt catgcggccc gtgcagacca cacaagagga agatggctgc    1080
tcctgcagat tccccgagga agaagaaggc ggctgcgagc tgagagtgaa gttctccaga    1140
tctgccgacg ctcctgccta ccagcaggga cagaaccagc tgtacaacga gctgaacctg    1200
gggagaagag aagagtacga cgtgctggat aagcggagag caggaccc tgagatgggc    1260 ggaaagccta acggaagaa tccccaagag gcctgtata atgagctgca gaaagacaag    1320
atggccgagg cctacagcga gatcggaatg aagggcgagc gcagaagagg caagggccac    1380
gatggactgt atcagggcct gagcacagcc accaaggata cctatgatgc cctgcacatg    1440
caggccctgc cacctagata a                                             1461
```

<210> SEQ ID NO 29
<211> LENGTH: 27
<212> TYPE: PRT
<213> ORGANISM: Artificial Sequence
<220> FEATURE:
<223> OTHER INFORMATION: Synthesized - 4-1BB transmembrane domain

<400> SEQUENCE: 29

Ile Ile Ser Phe Phe Leu Ala Leu Thr Ser Thr Ala Leu Leu Phe Leu
1               5                   10                  15

```
Leu Phe Phe Leu Thr Leu Arg Phe Ser Val Val
            20                  25

<210> SEQ ID NO 30
<211> LENGTH: 21
<212> TYPE: PRT
<213> ORGANISM: Artificial Sequence
<220> FEATURE:
<223> OTHER INFORMATION: Synthesized - CD8 alpha leader sequence

<400> SEQUENCE: 30

Met Ala Leu Pro Val Thr Ala Leu Leu Leu Pro Leu Ala Leu Leu Leu
1               5                   10                  15

His Ala Ala Arg Pro
            20

<210> SEQ ID NO 31
<211> LENGTH: 62
<212> TYPE: DNA
<213> ORGANISM: Artificial Sequence
<220> FEATURE:
<223> OTHER INFORMATION: Synthesized - CD8 alpha leader sequence

<400> SEQUENCE: 31
atggccctgc ctgtgacagc cctgctgctg cctctggctc tgctgctgca tgccgctaga      60
cc                                                                    62

<210> SEQ ID NO 32
<211> LENGTH: 1184
<212> TYPE: DNA
<213> ORGANISM: Artificial Sequence
<220> FEATURE:
<223> OTHER INFORMATION: Synthesized - EF-1 alpha promoter sequence

<400> SEQUENCE: 32
cgtgaggctc cggtgcccgt cagtgggcag agcgcacatc gcccacagtc cccgagaagt      60
tggggggagg ggtcggcaat tgaaccggtg cctagagaag gtggcgcggg gtaaactggg     120
aaagtgatgt cgtgtactgg ctccgccttt ttcccgaggg tggggagaa ccgtatataa      180 gtgcagtagt cgccgtgaac gttctttttc gcaacgggtt tgccgccaga acacaggtaa    240
gtgccgtgtg tggttcccgc gggcctggcc tctttacggg ttatggccct tgcgtgcctt    300
gaattacttc cacctggctg cagtacgtga ttcttgatcc cgagcttcgg gttgaagtg     360 ggtgggagag ttcgaggcct tgcgcttaag gagccccttc gcctcgtgct tgagttgagg    420
cctggcctgg gcgctgggc cgccgcgtgc gaatctggtg gcaccttcgc gcctgtctcg    480
ctgctttcga taagtctcta gccatttaaa attttgatg acctgctgcg acgcttttt      540 tctggcaaga tagtcttgta aatgcgggcc aagatctgca cactggtatt tcggtttttg    600
gggccgcggg cggcgacggg gcccgtgcgt cccagcgcac atgttcggcg aggcggggcc    660
tgcgagcgcg gccaccgaga atcgacgggg gtagtctca agctggcgg cctgctctgg      720 tgcctggcct cgcgccgccg tgtatcgccc cgccctgggc ggcaaggctg gcccggtcgg    780
caccagttgc gtgagcggaa agatggccgc ttcccggccc tgctgcaggg agctcaaaat    840
ggaggacgcg gcgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttggggggag ggttttatg    1020 cgatggagtt tccccacact gagtgggtgg agactgaagt taggccagct tggcacttga    1080
```

```
tgtaattctc cttggaattt gccctttttg agtttggatc ttggttcatt ctcaagcctc      1140
agacagtggt tcaaagtttt tttcttccat ttcaggtgtc gtga                      1184
```

<210> SEQ ID NO 33
<211> LENGTH: 488
<212> TYPE: PRT
<213> ORGANISM: Artificial Sequence
<220> FEATURE:
<223> OTHER INFORMATION: Synthesized - Humanized anti-CD19 CAR amino
      acid sequence

<400> SEQUENCE: 33

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Trp Gly Ala Gly Leu
            20                  25                  30

Leu Lys Pro Ser Glu Thr Leu Ser Leu Thr Cys Ala Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Leu Gly Val Ile Trp Gly Ser Glu Thr Thr Tyr Tyr
65                  70                  75                  80

Ser Ser Ser Leu Lys Ser Val Thr Ile Ile Lys Asp Thr Ser Lys Asn
                85                  90                  95

Gln Phe Phe Leu Lys Leu Ser Ser Val Thr Ala Ala Asp Thr Ala Val
            100                 105                 110

Tyr Tyr Cys Ala Arg His Tyr Tyr Gly Gly Ser Tyr Ala Met Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Ile Ser Lys Tyr Leu Asn Trp Tyr Gln
            180                 185                 190

Gln Lys Pro Gly Lys Ala Pro Lys Leu Leu Ile Tyr His Thr Ser Arg
        195                 200                 205

Leu His Ser Gly Val Pro Ser Arg Phe Ser Gly Ser Gly Ser Gly Thr
    210                 215                 220

Asp Phe Thr Phe Thr Ile Ser Ser Leu Gln Pro Glu Asp Ile Ala Thr
225                 230                 235                 240

Tyr Tyr Cys Gln Gln Gly Asn Thr Leu Pro Tyr Thr Phe Gly Gly Gly
                245                 250                 255

Thr Lys Val Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Ile Ser Phe Phe Leu Ala Leu Thr Ser Thr Ala Leu
305                 310                 315                 320

Leu Phe Leu Leu Phe Phe Leu Thr Leu Arg Phe Ser Val Val Lys Arg
                325                 330                 335

Gly Arg Lys Lys Leu Leu Tyr Ile Phe Lys Gln Pro Phe Met Arg Pro
```

```
            340                 345                 350
Val Gln Thr Thr Gln Glu Glu Asp Gly Cys Ser Cys Arg Phe Pro Glu
        355                 360                 365
Glu Glu Glu Gly Gly Cys Glu Leu Arg Val Lys Phe Ser Arg Ser Ala
    370                 375                 380
Asp Ala Pro Ala Tyr Gln Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser
        435                 440                 445
Glu Ile Gly Met Lys Gly Glu Arg Arg Arg Gly Lys Gly His Asp Gly
    450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg
                485

<210> SEQ ID NO 34
<211> LENGTH: 1485
<212> TYPE: DNA
<213> ORGANISM: Artificial Sequence
<220> FEATURE:
<223> OTHER INFORMATION: Synthesized - Humanized anti-CD19 CAR
      nucleotide sequence

<400> SEQUENCE: 34
ggatccgcca ccatggcatt gcctgttaca gctctgctgc tgcctctggc tctgcttctg      60
catgctgcta gacctcaggt tcagctgcag caatggggag ccggactgct gaagccttct     120
gagacactgt ctctgacctg tgccgtcagc ggagtgtctc tgcctgatta cggcgtgtcc     180
tggatcagac agcctcctgg caaaggactg aatggctggg agtgatctg gggcagcgag      240 acaacctact acagcagcag cctgaagtcc gtgaccatca tcaaggacac cagcaagaac     300
cagttcttcc tgaagctgag cagcgtgaca gccgccgata gccgtgta ctactgcgcc       360 agacactact actacggcgg cagctacgcc atggattatt ggggccaggg caccacagtg     420
acagtttcta gcggaggcgg aggaagtggc ggcggaggat ctggcggtgg tggttctgat     480
atccagatga cacagagccc tagcagcctg tctgcctctg tgggcgatag agtgaccatt     540
acctgtcggg ccagccagga catctccaag tacctgaact ggtatcagca gaagcccggc     600
aaggccccta gctgctgat ctaccacaca agcagactgc acagcggcgt gccaagcaga      660
ttttctggca gcggctctgg caccgacttc accttcacca tttctagcct gcagcctgag     720
gatatcgcca cctactattg ccagcagggc aacaccctgc cttacacctt ggcggaggc     780 accaaggtgg aaatcaagac caccacacca gctcctcggc tccaactcc tgctcctaca      840 attgcctctc agcctctgag cctgaggcct gaagcttgta gacctgctgc tggcggagcc     900
gtgcatacca gaggactgga tttcgcctgc gacatcatct cattctttct ggccctgacc     960
agcacagccc tgctgtttct gctgttcttt ctgacactgc ggttcagcgt ggtcaagcgg    1020
ggaagaaaga agctgctgta catcttcaag cagcccttca tgcggcccgt gcagacaaca    1080
caagaggaag atggctgctc ctgcagattc cccgaggaag aagaaggcgg ctgcgagctg    1140
agagtgaagt tctctagatc tgccgacgct cccgcctacc agcagggaca gaatcagctg    1200
```

```
tacaacgagc tgaatctggg gcgcagagaa gagtacgacg tgctggataa gagaagaggc   1260
agagatcccg agatgggcgg caagcctcgg agaaagaatc ctcaagaggg cctctacaat   1320
gagctgcaga agacaagat  ggccgaggcc tacagcgaga tcggaatgaa gggcgaacgc   1380
agaagaggaa agggccacga cggactgtat cagggcctga gcacagccac caaggatacc   1440
tatgatgccc tgcacatgca ggccctgcct ccaagatgaa tcgat               1485

<210> SEQ ID NO 35
<211> LENGTH: 357
<212> TYPE: DNA
<213> ORGANISM: Artificial Sequence
<220> FEATURE:
<223> OTHER INFORMATION: Synthesized - Humanized anti-CD19 binding
      domain heavy chain variable region nucleotide sequence

<400> SEQUENCE: 35
caggttcagc tgcagcaatg gggagccgga ctgctgaagc cttctgagac actgtctctg    60
acctgtgccg tgtatggcgt gtccctgcct gattacggcg tgtcctggat tagacagcct   120
cctggcaaag gcctggaatg gctgggagtg atctggggca gcgagacaac ctactacagc   180
agcagcctga gtccgtgac  catcagcgtg gacaccagca gaaccagtt  ctccctgaag   240 ctgtctagcg tgacagccgc cgataccgcc gtgtactact gtgccagaca ctactactac   300
ggcggcagct acgccatgga ttattggggc cagggcacca cagtgacagt ttctagc      357

<210> SEQ ID NO 36
<211> LENGTH: 357
<212> TYPE: DNA
<213> ORGANISM: Artificial Sequence
<220> FEATURE:
<223> OTHER INFORMATION: Synthesized  - Humanized anti-CD19 binding
      domain heavy chain variable region nucleotide sequence

<400> SEQUENCE: 36
caggttcagc tgcagcaatg gggagccgga ctgctgaagc cttctgagac actgtctctg    60
acctgtgccg tgtatggcgt gtccctgcct gattacggcg tgtcctggat tagacagcct   120
cctggcaaag gcctggaatg gctgggagtg atctggggca gcgagacaac ctactacagc   180
agcagcctga gtccgtgac  catcagcgtg gacaccagca agaaccagtt ctccctgaag   240
ctgtctagcg tgacagccgc cgataccgcc gtgtactact gtgccagaca ctactactac   300
ggcggcagct acgccatgga ttattggggc cagggcacca cagtgacagt ttctagc      357

<210> SEQ ID NO 37
<211> LENGTH: 321
<212> TYPE: DNA
<213> ORGANISM: Artificial Sequence
<220> FEATURE:
<223> OTHER INFORMATION: Synthesized - Humanized anti-CD19 binding
      domain light chain variable region

<400> SEQUENCE: 37
gatatccaga tgacacagag ccctagcagc ctgtctgcct ctgtgggcga tagagtgacc    60
attacctgca gagccagcca ggacatctcc aagtacctga actggtatca gcagaagccc   120
ggcaaggccc ctaagctgct gatctaccac acaagcagac tgcacagcgg cgtgccaagc   180
agattttctg gcagcggctc tggcaccgac ttcaccttca ccatttctag cctgcagcct   240
gaggatatcg ccacctacta ttgccagcag ggcaacaccc tgccttacac ctttggcgga   300
ggcaccaagg tggaaatcaa g                                             321
```

<210> SEQ ID NO 38
<211> LENGTH: 135
<212> TYPE: DNA
<213> ORGANISM: Artificial Sequence
<220> FEATURE:
<223> OTHER INFORMATION: Synthesized - CD8 alpha hinge region nucleotide
      sequence

<400> SEQUENCE: 38
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgat                                                      135

<210> SEQ ID NO 39
<211> LENGTH: 72
<212> TYPE: DNA
<213> ORGANISM: Artificial Sequence
<220> FEATURE:
<223> OTHER INFORMATION: Synthesized - CD8 alpha transmembrane domain
      nucleotide sequence

<400> SEQUENCE: 39
atctacatct gggcgccctt ggccgggact tgtggggtcc ttctcctgtc actggttatc      60 acccttact gc                                                           72

<210> SEQ ID NO 40
<211> LENGTH: 81
<212> TYPE: DNA
<213> ORGANISM: Artificial Sequence
<220> FEATURE:
<223> OTHER INFORMATION: Synthesized  - 4-1BB transmembrane domain
      nucleotide sequence

<400> SEQUENCE: 40
atcatctcat tctttctggc cctgaccagc acagccctgc tgtttctgct gttctttctg      60
acactgcggt tcagcgtggt c                                                81

<210> SEQ ID NO 41
<211> LENGTH: 126
<212> TYPE: DNA
<213> ORGANISM: Artificial Sequence
<220> FEATURE:
<223> OTHER INFORMATION: Synthesized - 4-1BB costimulatory domain
      nucleotide sequence

<400> SEQUENCE: 41
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 42
<211> LENGTH: 336
<212> TYPE: DNA
<213> ORGANISM: Artificial Sequence
<220> FEATURE:
<223> OTHER INFORMATION: Synthesized - CD3 zeta signaling domain
      nucleotide sequence

<400> SEQUENCE: 42
agagtgaagt tcagcaggag cgcagacgcc cccgcgtacc agcagggcca gaaccagctc      60
tataacgagc tcaatctagg acgaagagag gagtacgatg ttttggacaa gagacgtggc     120

```
cgggaccctg agatggggg  aaagccgaga aggaagaacc ctcaggaagg cctgtacaat    180
gaactgcaga aagataagat ggcggaggcc tacagtgaga ttgggatgaa aggcgagcgc    240
cggaggggca agggcacga  tggcctttac cagggtctca gtacagccac caaggacacc    300
tacgacgccc ttcacatgca ggccctgccc cctcgc                              336
```

<210> SEQ ID NO 43
<211> LENGTH: 45
<212> TYPE: DNA
<213> ORGANISM: Artificial Sequence
<220> FEATURE:
<223> OTHER INFORMATION: Synthesized - VH-VL linker nucleotide sequence

<400> SEQUENCE: 43

```
ggaggcggag gaagtggtgg cggaggttct ggcggcggag gatct                    45
```

<210> SEQ ID NO 44
<211> LENGTH: 63
<212> TYPE: DNA
<213> ORGANISM: Artificial Sequence
<220> FEATURE:
<223> OTHER INFORMATION: Synthesized - CD8 alpha leader sequence

<400> SEQUENCE: 44

```
atggcattgc ctgttacagc tctgctgctg cctctggctc tgcttctgca tgctgctaga    60
cct                                                                  63
```

<210> SEQ ID NO 45
<211> LENGTH: 72
<212> TYPE: DNA
<213> ORGANISM: Artificial Sequence
<220> FEATURE:
<223> OTHER INFORMATION: Synthesized - CD8 alpha transmembrane domain
      nucleotide sequence

<400> SEQUENCE: 45

```
atctacattt ggcccctct  ggctggaaca tgtggcgtgc tgctgctcag cctggtcatc    60
accctgtact gc                                                        72
```

<210> SEQ ID NO 46
<211> LENGTH: 45
<212> TYPE: DNA
<213> ORGANISM: Artificial Sequence
<220> FEATURE:
<223> OTHER INFORMATION: Synthesized - VH-VL linker nucleotide sequence

<400> SEQUENCE: 46

```
ggaggcggag gaagtggcgg cggaggatct ggcggtggtg gttct                    45
```

<210> SEQ ID NO 47
<211> LENGTH: 126
<212> TYPE: DNA
<213> ORGANISM: Artificial Sequence
<220> FEATURE:
<223> OTHER INFORMATION: Synthesized - 4-1BB costimulatory domain
      nucleotide sequence

<400> SEQUENCE: 47

```
aagcggggaa gaaagaagct gctgtacatc ttcaagcagc ccttcatgcg gcccgtgcag    60
acaacacaag aggaagatgg ctgctcctgc agattccccg aggaagaaga aggcggctgc    120
gagctg                                                               126
```

<210> SEQ ID NO 48
<211> LENGTH: 339
<212> TYPE: DNA
<213> ORGANISM: Artificial Sequence
<220> FEATURE:
<223> OTHER INFORMATION: Synthesized - CD3 zeta signaling domain
      nucleotide sequence

<400> SEQUENCE: 48
agagtgaagt tctccagatc tgccgacgct cctgcttatc agcagggcca gaaccagctg      60
tacaacgagc tgaatctggg gagaagagaa gagtacgacg tgctggataa gcggagaggc     120
agagatcctg agatgggcgg caagcccaga cggaagaatc ctcaagaggg cctgtataat     180
gagctgcaga agacaagat ggccgaggcc tacagcgaga tcggaatgaa gggcgagcgc     240
agaagaggca aggacacga tggactgtac cagggcctga gcacagccac caaggatacc     300
tatgatgccc tgcacatgca ggccctgcca cctagataa                            339

<210> SEQ ID NO 49
<211> LENGTH: 339
<212> TYPE: DNA
<213> ORGANISM: Artificial Sequence
<220> FEATURE:
<223> OTHER INFORMATION: Synthesized - CD3 zeta signaling domain
      nucleotide sequence

<400> SEQUENCE: 49
agagtgaagt tctccagatc tgccgacgct cctgcctatc agcagggcca gaatcagctg      60
tacaacgagc tgaatctggg gcgcagagaa gagtacgacg tgctggacaa gagaaggggc     120
agagatcctg agatgggcgg caagcccaga cggaagaatc ctcaagaggg cctgtataat     180
gagctgcaga agacaagat ggccgaggcc tacagcgaga tcggaatgaa gggcgaacgc     240
agaagaggca agggccacga tggactgtat cagggcctga gcacagccac caaggatacc     300
tatgatgccc tgcacatgca ggccctgcca cctagataa                            339

<210> SEQ ID NO 50
<211> LENGTH: 321
<212> TYPE: DNA
<213> ORGANISM: Artificial Sequence
<220> FEATURE:
<223> OTHER INFORMATION: Synthesized - Humanized anti-CD19 binding
      domain light chain variable region

<400> SEQUENCE: 50
gatatccaga tgacacagag ccctagcagc ctgtctgcct ctgtgggcga tagagtgacc      60
attacctgca gagccagcca ggacatcagc aagtacctga actggtatca gcagaagccc     120
ggcaaggccc ctaagctgct gatctaccac acaagcagac tgcacagcgg cgtgccaagc     180 agatttctg gcagcggctc tggcaccgac ttcaccttca ccatttctag cctgcagcct     240
gaggatatcg ccacctacta ttgccagcag ggcaacaccc tgccttacac ctttggcgga     300
ggcaccaagg tggaaatcaa g                                                321

<210> SEQ ID NO 51
<211> LENGTH: 321
<212> TYPE: DNA
<213> ORGANISM: Artificial Sequence
<220> FEATURE:
<223> OTHER INFORMATION: Synthesized - Humanized anti-CD19 binding
      domain light chain variable region

<400> SEQUENCE: 51

```
gatatccaga tgacacagag ccctagcagc ctgtctgcct ctgtgggcga tagagtgacc      60
attacctgtc gggccagcca ggacatctcc aagtacctga actggtatca gcagaagccc     120
ggcaaggccc ctaagctgct gatctaccac acaagcagac tgcacagcgg cgtgccaagc     180
agattttctg gcagcggctc tggcaccgac ttcaccttca ccatttctag cctgcagcct     240
gaggatatcg ccacctacta ttgccagcag ggcaacaccc tgccttacac ctttggcgga     300
ggcaccaagg tggaaatcaa g                                               321
```

<210> SEQ ID NO 52
<211> LENGTH: 488
<212> TYPE: PRT
<213> ORGANISM: Artificial Sequence
<220> FEATURE:
<223> OTHER INFORMATION: Synthesized - Humanized anti-CD19 CAR amino
      acid sequence

<400> SEQUENCE: 52

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Trp Gly Ala Gly Leu
            20                  25                  30

Leu Lys Pro Ser Glu Thr Leu Ser Leu Thr Cys Ala Val Tyr Gly Val
        35                  40                  45

Ser Leu Pro Asp Tyr Gly Val Ser Trp Ile Arg Gln Pro Pro Gly Lys
    50                  55                  60

Gly Leu Glu Trp Leu Gly Val Ile Trp Gly Ser Glu Thr Thr Tyr Tyr
65                  70                  75                  80

Ser Ser Ser Leu Lys Ser Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg His Tyr Tyr Gly Gly Ser Tyr Ala Met Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Ile Ser Lys Tyr Leu Asn Trp Tyr Gln
            180                 185                 190

Gln Lys Pro Gly Lys Ala Pro Lys Leu Leu Ile Tyr His Thr Ser Arg
        195                 200                 205

Leu His Ser Gly Val Pro Ser Arg Phe Ser Gly Ser Gly Ser Gly Thr
    210                 215                 220

Asp Phe Thr Phe Thr Ile Ser Ser Leu Gln Pro Glu Asp Ile Ala Thr
225                 230                 235                 240

Tyr Tyr Cys Gln Gln Gly Asn Thr Leu Pro Tyr Thr Phe Gly Gly Gly
                245                 250                 255

Thr Lys Val Glu Ile Lys Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
```

Ala Cys Asp Ile Ile Ser Phe Phe Leu Ala Leu Thr Ser Thr Ala Leu
305                 310                 315                 320

Leu Phe Leu Leu Phe Phe Leu Thr Leu Arg Phe Ser Val Val Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
        370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 53
<211> LENGTH: 1467
<212> TYPE: DNA
<213> ORGANISM: Artificial Sequence
<220> FEATURE:
<223> OTHER INFORMATION: Synthesized - Humanized anti-CD19 CAR
      nucleotide sequence

<400> SEQUENCE: 53
atggccctgc ctgtgacagc tctgctgctg cctcttgctc tgcttctgca tgctgctaga     60
cctcaggttc agctgcagca atggggagcc ggactgctga gccttctga gacactgtct    120 ctgacctgtg ccgtgtatgg cgtgtccctg cctgattacg gcgtgtcctg gattagacag    180
cctcctggca aaggcctgga atggctggga gtgatctggg gcagcgagac aacctactac    240
agcagcagcc tgaagtccgt gaccatcagc gtggacacca gcaagaacca gttctccctg    300
aagctgtcta gcgtgacagc cgccgatacc gccgtgtact actgtgccag acactactac    360
tacggcggca gctacgccat ggattattgg ggccagggca ccacagtgac agtttctagc    420
ggaggcggag gaagtggtgg cggaggttct ggcggcggag gatctgatat ccagatgaca    480
cagagcccta gcagcctgtc tgcctctgtg ggcgatagtg taccattac tgcagagcc     540 agccaggaca tcagcaagta cctgaactgg tatcagcaga gcccggcaa ggcccctaag    600 ctgctgatct accacacaag cagactgcac agcggcgtgc caagcagatt ttctggcagc    660
ggctctggca ccgacttcac cttcaccatt tctagcctgc agcctgagga tatcgccacc    720
tactattgcc agcagggcaa caccctgcct tacacctttg gcggaggcac caaggtggaa    780
atcaagacca ccacaccagc tcctcggcct ccaactcctg ctcctacaat tgcctctcag    840
cctctgagcc tgaggcctga agcttgtaga cctgctgctg gcggagccgt gcataccaga    900

| | |
|---|---|
| ggactggatt tcgcctgcga catcatctca ttctttctgg ccctgaccag cacagccctg | 960 |
| ctgtttctgc tgttctttct gacactgcgg ttcagcgtgg tcaagcgggg cagaaagaag | 1020 |
| ctgctgtaca tcttcaagca gcccttcatg cggcccgtgc agacaacaca agaggaagat | 1080 |
| ggctgctcct gcagattccc cgaggaagaa gaaggcggct gcgagctgag agtgaagttc | 1140 |
| tccagatctg ccgacgctcc tgcttatcag cagggccaga accagctgta caacgagctg | 1200 |
| aatctgggga agagaagaa gtacgacgtg ctggataagc ggagaggcag agatcctgag | 1260 |
| atgggcggca agcccagacg gaagaatcct caagagggcc tgtataatga gctgcagaaa | 1320 |
| gacaagatgg ccgaggccta cagcgagatc ggaatgaagg gcgagcgcag aagaggcaaa | 1380 |
| ggacacgatg gactgtacca gggcctgagc acagccacca aggatacccta tgatgccctg | 1440 |
| cacatgcagg ccctgccacc tagataa | 1467 |

<210> SEQ ID NO 54
<211> LENGTH: 9126
<212> TYPE: DNA
<213> ORGANISM: Artificial Sequence
<220> FEATURE:
<223> OTHER INFORMATION: Synthesized - Vector sequence

<400> SEQUENCE: 54

| | |
|---|---|
| ttcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |

```
aaagtaagac caccgcacag caagcggccg gccgctgatc ttcagacctg gaggaggaga    1560
tatgagggac aattggagaa gtgaattata taaatataaa gtagtaaaaa ttgaaccatt    1620
aggagtagca cccaccaagg caaagagaag agtggtgcag agagaaaaaa gagcagtggg    1680
aataggagct ttgttccttg ggttcttggg agcagcagga agcactatgg gcgcagcgtc    1740
aatgacgctg acggtacagg ccagacaatt attgtctggt atagtgcagc agcagaacaa    1800
tttgctgagg gctattgagg cgcaacagca tctgttgcaa ctcacagtct ggggcatcaa    1860
gcagctccag gcaagaatcc tggctgtgga agatacccta aaggatcaac agctcctggg    1920
gatttggggt tgctctggaa aactcatttg caccactgct gtgccttgga atgctagttg    1980
gagtaataaa tctctggaac agatttggaa tcacacgacc tggatggagt gggacagaga    2040
aattaacaat tacacaagct taatacactc cttaattgaa gaatcgcaaa accagcaaga    2100
aaagaatgaa caagaattat tggaattaga taaatgggca agtttgtgga attggtttaa    2160
cataacaaat tggctgtggt atataaaatt attcataatg atagtaggag gcttggtagg    2220
tttaagaata gttttgctg tactttctat agtgaataga gttaggcagg gatattcacc    2280
attatcgttt cagacccacc tcccaacccc gaggggaccc gacaggcccg aaggaataga    2340
agaagaaggt ggagagagag acagagacag atccattcga ttagtgaacg gatcggcact    2400
gcgtgcgcca attctgcaga caaatggcag tattcatcca caattttaaa agaaaagggg    2460
ggattggggg gtacagtgca ggggaaagaa tagtagacat aatagcaaca gacatacaaa    2520
ctaaagaatt acaaaaacaa attacaaaaa ttcaaaattt tcgggtttat tacagggaca    2580
gcagagatcc agtttggtta gtaccgggcc cgctctagcg tgaggctccg gtgcccgtca    2640
gtgggcagag cgcacatcgc ccacagtccc cgagaagttg gggggagggg tcggcaattg    2700
aaccggtgcc tagagaaggt ggcgcggggt aaactgggaa agtgatgtcg tgtactggct    2760
ccgccttttt cccgagggtg ggggagaacc gtatataagt gcagtagtcg ccgtgaacgt    2820 tcttttcgc aacgggtttg ccgccagaac acaggtaagt gccgtgtgtg gttcccgcgg    2880
gcctggcctc tttacgggtt atggcccttg cgtgccttga attacttcca cctggctgca    2940
gtacgtgatt cttgatcccg agcttcgggt tggaagtggg tgggagagtt cgaggccttg    3000
cgcttaagga gccccttcgc ctcgtgcttg agttgaggcc tggcctgggc gctggggccg    3060
ccgcgtgcga atcggtggc accttcgcgc ctgtctcgct gctttcgata agtctctagc    3120
catttaaaat ttttgatgac ctgctgcgac gctttttttc tggcaagata gtcttgtaaa    3180
tgcgggccaa gatctgcaca ctggtatttc ggttttggg gccgcgggcg cgacggggc    3240 ccgtgcgtcc cagcgcacat gttcggcgag gcgggcctg cgagcgcggc caccgagaat    3300
cggacggggg tagtctcaag ctggccgcc tgctctggtg cctggcctcg cgccgccgtg    3360
tatcgccccg ccctgggcgg caaggctggc ccggtcggca ccagttgcgt gagcggaaag    3420
atggccgctt cccggccctg ctgcaggag ctcaaaatgg aggacgcggc gctcgggaga    3480
gcgggcgggt gagtcaccca cacaaaggaa aagggccttt ccgtcctcag ccgtcgcttc    3540
atgtgactcc acggagtacc gggcgccgtc caggcacctc gattagttct cgagcttttg    3600
gagtacgtcg tctttaggtt ggggggaggg gttttatgcg atggagtttc cccacactga    3660
gtgggtggag actgaagtta ggccagcttg gcacttgatg taattctcct tggaatttgc    3720
cctttttgag tttggatctt ggttcattct caagcctcag acagtggttc aaagtttttt    3780
tcttccattt caggtgtcgt gagcggccgc tgagttaact attatggccc tgcctgtgac    3840
```

```
agctctgctg ctgcctcttg ctctgcttct gcatgctgct agacctcagg ttcagctgca    3900
gcaatgggga gccggactgc tgaagccttc tgagacactg tctctgacct gtgccgtcag    3960
cggagtgtct ctgcctgatt acggcgtgtc ctggatcaga cagcctcctg gcaaaggact    4020
ggaatggctg ggagtgatct ggggcagcga caacctac tacagcagca gcctgaagtc    4080
cgtgaccatc atcaaggaca ccagcaagaa ccagttcttc ctgaagctga gcagcgtgac    4140
agccgccgat acagccgtgt actactgcgc cagacactac tactacgcg gcagctacgc    4200
catggattat tggggccagg gcaccacagt gacagtttct agcggaggcg gaggaagtgg    4260
tggcggaggt tctggcggcg gaggatctga tatccagatg acacagagcc ctagcagcct    4320
gtctgcctct gtgggcgata gagtgaccat tacctgcaga gccagccagg acatctccaa    4380
gtacctgaac tggtatcagc agaagcccgg caaggcccct aagctgctga tctaccacac    4440
aagcagactg cacagcggcg tgccaagcag attttctggc agcggtctg gcaccgactt    4500
caccttcacc atttctagcc tgcagcctga ggatatcgcc acctactatt gccagcaggg    4560
caacaccctg ccttacacct ttggcggagg caccaaggtg gaaatcaaga ccaccacacc    4620
agctcctcgg cctccaactc ctgctcctac aattgcctct cagcctctga gcctgaggcc    4680
tgaagcttgt agacctgctg ctggcggagc cgtgcatacc agaggactgg atttcgcctg    4740
cgacatctac atttgggccc ctctggctgg aacatgtggc gtgctgctgc tctccctggt    4800
catcaccctg tactgcaagc ggggcagaaa gaagctgctg tacatcttca gcagcccttt    4860
catgcggccc gtgcagacaa cacaagagga agatggctgc tcctgcagat tccccgagga    4920
agaagaaggc ggctgcgagc tgagagtgaa gttctccaga tctgccgacg ctcctgccta    4980
tcagcagggc cagaatcagc tgtacaacga gctgaatctg gggcgcagag aagagtacga    5040
cgtgctggac aagagaaggg gcagagatcc tgagatgggc ggcaagccca cacgaagaa    5100
tcctcaagag ggcctgtata atgagctgca gaaagacaag atggccgagg cctacagcga    5160
gatcggaatg aagggcgaac gcagaagagg caagggccac gatggactgt atcagggcct    5220
gagcacagcc accaaggata cctatgatgc cctgcacatg caggccctgc cacctagata    5280
agatccgccc ctctcccctcc ccccccccta acgttactgg ccgaagccgc ttggaataag    5340
gccggtgtgc gttttgtctat atgttatttt ccaccatatt gccgtctttt ggcaatgtga    5400
gggcccggaa acctggccct gtcttcttga cgagcattcc taggggtctt tcccctctcg    5460
ccaaaggaat gcaaggtctg ttgaatgtcg tgaaggaagc agttcctctg gaagcttctt    5520
gaagacaaac aacgtctgta gcgaccctt gcaggcagcg gaaccccca cctggcgaca    5580
ggtgcctctg cggccaaaag ccacgtgtat aagatacacc tgcaaaggcg gcacaacccc    5640
agtgccacgt tgtgagttgg atagttgtgg aaagagtcaa atggctctcc tcaagcgtat    5700
tcaacaaggg gctgaaggat gcccagaagg taccccattg tatgggatct gatctggggc    5760
ctcggtacac atgctttaca tgtgtttagt cgaggttaaa aaacgtcta ggccccccga    5820
accacgggga cgtggttttc ctttgaaaaa cacgatgata atatgccac aaccatggtg    5880
agcaagggcg aggagctgtt caccggggtg gtgcccatcc tggtcgagct ggacggcgac    5940
gtaaacggcc acaagttcag cgtgtccggc gagggcgagg gcgatgccac ctacggcaag    6000
ctgaccctga agttcatctg caccaccggc aagctgcccg tgccctggcc cacctcgtg    6060
accacccctga cctacggcgt gcagtgcttc agccgctacc ccgaccacat gaagcagcac    6120
gacttcttca gtccgccat gcccgaaggc tacgtccagg agcgcaccat cttcttcaag    6180
gacgacggca actacaagac ccgcgccgag gtgaagttcg agggcgacac cctggtgaac    6240
```

```
cgcatcgagc tgaagggcat cgacttcaag gaggacggca acatcctggg gcacaagctg      6300
gagtacaact acaacagcca caacgtctat atcatggccg acaagcagaa gaacggcatc      6360
aaggtgaact tcaagatccg ccacaacatc gaggacggca gcgtgcagct cgccgaccac      6420
taccagcaga acacccccat cggcgacggc cccgtgctgc tgcccgacaa ccactacctg      6480
agcacccagt ccgccctgag caaagacccc aacgagaagc gcgatcacat ggtcctgctg      6540
gagttcgtga ccgccgccgg gatcactctc ggcatggacg agctgtacaa gtaaagcggc      6600
cgcatcgata ccgtcgacct cgatcgagac ctagaaaaac atggagcaat cacaagtagc      6660
aatacagcag ctaccaatgc tgattgtgcc tggctagaag cacaagagga ggaggaggtg      6720
ggttttccag tcacacctca ggtaccttta agaccaatga cttacaaggc agctgtagat      6780
cttagccact ttttaaaaga aaaggggggga ctggaagggc taattcactc ccaacgaaga      6840
caagatatcc ttgatctgtg gatctaccac acacaaggct acttccctga ttggcagaac      6900
tacacaccag ggccagggat cagatatcca ctgacctttg gatggtgcta caagctagta      6960
ccagttgagc aagagaaggt agaagaagcc aatgaaggag agaacacccg cttgttacac      7020
cctgtgagcc tgcatgggat ggatgacccg gagagagaag tattagagtg gaggtttgac      7080
agccgcctag catttcatca catggcccga gagctgcatc cggactgtac tgggtctctc      7140
tggttagacc agatctgagc ctgggagctc tctggctaac tagggaaccc actgcttaag      7200
cctcaataaa gcttgccttg agtgcttcaa gtagtgtgtg cccgtctgtt gtgtgactct      7260
ggtaactaga gatccctcag acccttttag tcagtgtgga aaatctctag cagcatgtga      7320
gcaaaaggcc agcaaaggc caggaaccgt aaaaaggccg cgttgctggc gtttttccat      7380
aggctccgcc cccctgacga gcatcacaaa aatcgacgct caagtcagag gtggcgaaac      7440
ccgacaggac tataaagata ccaggcgttt ccccctggaa gctccctcgt gcgctctcct      7500
gttccgaccc tgccgcttac cggatacctg tccgcctttc tcccttcggg aagcgtggcg      7560
ctttctcata gctcacgctg taggtatctc agttcggtgt aggtcgttcg ctccaagctg      7620
ggctgtgtgc acgaaccccc cgttcagccc gaccgctgcg ccttatccgg taactatcgt      7680
cttgagtcca acccggtaag acacgactta tcgccactgg cagcagccac tggtaacagg      7740
attagcagag cgaggtatgt aggcggtgct acagagttct tgaagtggtg gcctaactac      7800
ggctacacta gaagaacagt atttggtatc tgcgctctgc tgaagccagt taccttcgga      7860
aaaagagttg gtagctcttg atccggcaaa caaaccaccg ctggtagcgg tggtttttt      7920 gtttgcaagc agcagattac gcgcagaaaa aaaggatctc aagaagatcc tttgatcttt      7980
tctacggggt ctgacgctca gtggaacgaa aactcacgtt aagggatttt ggtcatgaga      8040
ttatcaaaaa ggatcttcac ctagatcctt ttaaattaaa aatgaagttt taaatcaatc      8100
taaagtatat atgagtaaac ttggtctgac agttaccaat gcttaatcag tgaggcacct      8160
atctcagcga tctgtctatt tcgttcatcc atagttgcct gactccccgt cgtgtagata      8220
actacgatac gggagggctt accatctggc cccagtgctg caatgatacc gcgagaccca      8280
cgctcaccgg ctccagattt atcagcaata accagccag ccggaagggc cgagcgcaga      8340
agtggtcctg caactttatc cgcctccatc cagtctatta attgttgccg ggaagctaga      8400
gtaagtagtt cgccagttaa tagtttgcgc aacgttgttg ccattgctac aggcatcgtg      8460
gtgtcacgct cgtcgtttgg tatggcttca ttcagctccg gttcccaacg atcaaggcga      8520
gttacatgat cccccatgtt gtgcaaaaaa gcggttagct ccttcggtcc tccgatcgtt      8580
```

| | |
|---|---:|
| gtcagaagta agttggccgc agtgttatca ctcatggtta tggcagcact gcataattct | 8640 |
| cttactgtca tgccatccgt aagatgcttt tctgtgactg gtgagtactc aaccaagtca | 8700 |
| ttctgagaat agtgtatgcg gcgaccgagt tgctcttgcc cggcgtcaat acgggataat | 8760 |
| accgcgccac atagcagaac tttaaaagtg ctcatcattg gaaaacgttc ttcggggcga | 8820 |
| aaactctcaa ggatcttacc gctgttgaga tccagttcga tgtaacccac tcgtgcaccc | 8880 |
| aactgatctt cagcatcttt tactttcacc agcgtttctg ggtgagcaaa aacaggaagg | 8940 |
| caaaatgccg caaaaaaggg aataagggcg acacggaaat gttgaatact catactcttc | 9000 |
| cttttttcaat attattgaag catttatcag ggttattgtc tcatgagcgg atacatattt | 9060 |
| gaatgtattt agaaaaataa acaaataggg gttccgcgca catttccccg aaaagtgcca | 9120 |
| cctgac | 9126 |

<210> SEQ ID NO 55
<211> LENGTH: 9126
<212> TYPE: DNA
<213> ORGANISM: Artificial Sequence
<220> FEATURE:
<223> OTHER INFORMATION: Synthesized - Vector sequence

<400> SEQUENCE: 55

| | |
|---|---:|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |

```
aaagtaagac caccgcacag caagcggccg gccgctgatc ttcagacctg gaggaggaga    1560
tatgagggac aattggagaa gtgaattata taaatataaa gtagtaaaaa ttgaaccatt    1620
aggagtagca cccaccaagg caaagagaag agtggtgcag agagaaaaaa gagcagtggg    1680
aataggagct ttgttccttg ggttcttggg agcagcagga agcactatgg gcgcagcgtc    1740
aatgacgctg acggtacagg ccagacaatt attgtctggt atagtgcagc agcagaacaa    1800
tttgctgagg gctattgagg cgcaacagca tctgttgcaa ctcacagtct ggggcatcaa    1860
gcagctccag gcaagaatcc tggctgtgga agatacctaa aggatcaaca gctcctggga    1920
gatttggggt tgctctggaa aactcatttg caccactgct gtgccttgga atgctagttg    1980
gagtaataaa tctctggaac agatttggaa tcacacgacc tggatggagt gggacagaga    2040
aattaacaat tacacaagct taatacactc cttaattgaa gaatcgcaaa accagcaaga    2100
aaagaatgaa caagaattat tggaattaga taaatgggca gtttgtggaa attggtttaa    2160
cataacaaat tggctgtggt atataaaatt attcataatg atagtaggag gcttggtagg    2220
tttaagaata gttttgctg tactttctat agtgaataga gttaggcagg gatattcacc    2280
attatcgttt cagacccacc tcccaacccc gaggggaccc gacaggcccg aaggaataga    2340
agaagaaggt ggagagagag acagagacag atccattcga ttagtgaacg gatcggcact    2400
gcgtgcgcca attctgcaga caaatggcag tattcatcca cattttaaa agaaaagggg    2460 ggattggggg gtacagtgca ggggaaagaa tagtagacat aatagcaaca gacatacaaa    2520
ctaaagaatt acaaaaacaa attacaaaaa ttcaaaattt tcgggttat tacagggaca    2580 gcagagatcc agtttggtta gtaccgggcc cgctctagcg tgaggctccg gtgcccgtca    2640
gtgggcagag cgcacatcgc ccacagtccc cgagaagttg gggggagggg tcggcaattg    2700
aaccggtgcc tagagaaggt ggcgcgggt aaactgggaa agtgatgtcg tgtactggct    2760
ccgccttttt cccgagggtg ggggagaacc gtatataagt gcagtagtcg ccgtgaacgt    2820 tcttttttcgc aacgggtttg ccgccagaac acaggtaagt gccgtgtgtg gttcccgcgg    2880
gcctggcctc tttacgggtt atggcccttg cgtgccttga attacttcca cctggctgca    2940
gtacgtgatt cttgatcccg agcttcgggt tggaagtggg tgggagagtt cgaggccttg    3000
cgcttaagga gccccttcgc ctcgtgcttg agttgaggcc tggcctgggc gctggggccg    3060
ccgcgtgcga atcggtggc accttcgcgc ctgtctcgct gctttcgata agtctctagc    3120
catttaaaat ttttgatgac ctgctgcgac gctttttttc tggcaagata gtcttgtaaa    3180
tgcgggccaa gatctgcaca ctggtatttc ggttttggg gccgcgggcg cgacggggc    3240 ccgtgcgtcc cagcgcacat gttcggcgag gcggggcctg cgagcgcggc caccgagaat    3300
cggacggggg tagtctcaag ctggccgcc tgctctggtg cctggcctcg cgccgccgtg    3360
tatcgccccg ccctgggcgg caaggctggc ccggtcggca ccagttgcgt gagcggaaag    3420
atggccgctt cccggccctg ctgcaggag ctcaaaatgg aggacgcggc gctcgggaga    3480
gcgggcgggt gagtcacccca cacaaaggaa aagggccttt ccgtcctcag ccgtcgcttc    3540
atgtgactcc acggagtacc gggcgccgtc caggcacctc gattagttct cgagcttttg    3600
gagtacgtcg tctttaggtt gggggaggg gttttatgcg atggagtttc cccacactga    3660
gtgggtggag actgaagtta ggccagcttg gcacttgatg taattctcct tggaatttgc    3720 ccttttttgag tttggatctt ggttcattct caagcctcag acagtggttc aaagttttttt    3780 tcttccattt caggtgtcgt gagcggccgc tgagttaact attatggccc tgcctgtgac    3840
```

```
agctctgctg ctgcctcttg ctctgcttct gcatgctgct agacctcagg ttcagctgca    3900
gcaatgggga gccggactgc tgaagccttc tgagacactg tctctgacct gtgccgtgta    3960
tggcgtgtcc ctgcctgatt acggcgtgtc ctggattaga cagcctcctg gcaaaggcct    4020
ggaatggctg ggagtgatct ggggcagcga acaacctac tacagcagca gcctgaagtc     4080
cgtgaccatc agcgtggaca ccagcaagaa ccagttctcc ctgaagctgt ctagcgtgac    4140
agccgccgat accgccgtgt actactgtgc cagacactac tactacgcg gcagctacgc     4200
catggattat tggggccagg gcaccacagt gacagtttct agcggaggcg aggaagtgg     4260
tggcggaggt tctggcggcg gaggatctga tatccagatg acacagagcc ctagcagcct    4320
gtctgcctct gtgggcgata gagtgaccat tacctgcaga gccagccagg acatcagcaa    4380
gtacctgaac tggtatcagc agaagcccgg caaggcccct aagctgctga tctaccacac    4440
aagcagactg cacagcggcg tgccaagcag atttttctgg agcggctctg gcaccgactt    4500
caccttcacc atttctagcc tgcagcctga ggatatcgcc acctactatt gccagcaggg    4560
caacaccctg ccttacacct ttggcggagg caccaaggtg gaaatcaaga ccaccacacc    4620
agctcctcgg cctccaactc ctgctcctac aattgcctct cagcctctga gcctgaggcc    4680
tgaagcttgt agacctgctg ctggcggagc cgtgcatacc agaggactgg atttcgcctg    4740
cgacatctac atttgggccc ctctggctgg aacatgtggc gtgctgctgc tcagcctggt    4800
catcaccctg tactgcaagc ggggcagaaa gaagctgctg tacatcttca gcagcccttt    4860
catgcggccc gtgcagacaa cacaagagga agatggctgc tcctgcagat tccccgagga    4920
agaagaaggc ggctgcgagc tgagagtgaa gttctccaga tctgccgacg ctcctgctta    4980
tcagcagggc cagaaccagc tgtacaacga gctgaatctg ggagaagag aagagtacga    5040
cgtgctggat aagcggagag gcagagatcc tgagatgggc ggcaagccca cacgaagaa     5100
tcctcaagag ggcctgtata atgagctgca gaaagacaag atggccgagg cctacagcga    5160
gatcggaatg aagggcgagc gcagaagagg caaaggacac gatggactgt accagggcct    5220
gagcacagcc accaaggata cctatgatgc cctgcacatg caggccctgc acctagata     5280
agatccgccc ctctccctcc ccccccccta acgttactgg ccgaagccgc ttggaataag    5340
gccggtgtgc gtttgtctat atgttatttt ccaccatatt gccgtctttt ggcaatgtga    5400
gggcccggaa acctggccct gtcttcttga cgagcattcc taggggtctt tcccctctcg    5460
ccaaaggaat gcaaggtctg ttgaatgtcg tgaaggaagc agttcctctg gaagcttctt    5520
gaagacaaac aacgtctgta gcgaccctt gcaggcagcg aaccccca cctggcgaca      5580
ggtgcctctg cggccaaaag ccacgtgtat aagatacacc tgcaaaggcg gcacaacccc    5640
agtgccacgt tgtgagttgg atagttgtgg aaagagtcaa atggctctcc tcaagcgtat    5700
tcaacaaggg gctgaaggat gcccagaagg taccccattg tatgggatct gatctggggc    5760
ctcggtacac atgctttaca tgtgtttagt cgaggttaaa aaaacgtcta ggccccccga    5820
accacgggga cgtggttttc ctttgaaaaa cacgatgata atatggccac aaccatggtg    5880
agcaagggcg aggagctgtt caccgggtg gtgcccatcc tggtcgagct ggacggcgac     5940
gtaaacggcc acaagttcag cgtgtccggc gagggcgagg gcgatgccac ctacggcaag    6000
ctgaccctga agttcatctg caccaccggc aagctgcccg tgcctggcc caccctcgtg     6060
accaccctga cctacggcgt gcagtgcttc agccgctacc ccgaccacat gaagcagcac    6120
gacttcttca gtccgccat gcccgaaggc tacgtccagg agcgcaccat cttcttcaag     6180
gacgacggca actacaagac ccgcgccgag gtgaagttcg agggcgacac cctggtgaac    6240
```

```
cgcatcgagc tgaagggcat cgacttcaag gaggacggca acatcctggg gcacaagctg    6300
gagtacaact acaacagcca caacgtctat atcatggccg acaagcagaa gaacggcatc    6360
aaggtgaact tcaagatccg ccacaacatc gaggacggca gcgtgcagct cgccgaccac    6420
taccagcaga acacccccat cggcgacggc cccgtgctgc tgcccgacaa ccactacctg    6480
agcacccagt ccgccctgag caaagacccc aacgagaagc gcgatcacat ggtcctgctg    6540
gagttcgtga ccgccgccgg gatcactctc ggcatggacg agctgtacaa gtaaagcggc    6600
cgcatcgata ccgtcgacct cgatcgagac ctagaaaaac atggagcaat cacaagtagc    6660
aatacagcag ctaccaatgc tgattgtgcc tggctagaag cacaagagga ggaggaggtg    6720
ggttttccag tcacacctca ggtaccttta agaccaatga cttacaaggc agctgtagat    6780
cttagccact ttttaaaaga aaagggggga ctggaagggc taattcactc ccaacgaaga    6840
caagatatcc ttgatctgtg gatctaccac acacaaggct acttccctga ttggcagaac    6900
tacacaccag ggccagggat cagatatcca ctgacctttg gatggtgcta caagctagta    6960
ccagttgagc aagagaaggt agaagaagcc aatgaaggag agaacacccg cttgttacac    7020
cctgtgagcc tgcatgggat ggatgacccg gagagagaag tattagagtg gaggtttgac    7080
agccgcctag catttcatca catggcccga gagctgcatc cggactgtac tgggtctctc    7140
tggttagacc agatctgagc ctgggagctc tctggctaac tagggaaccc actgcttaag    7200
cctcaataaa gcttgccttg agtgcttcaa gtagtgtgtg cccgtctgtt gtgtgactct    7260
ggtaactaga gatccctcag acccttttag tcagtgtgga aaatctctag cagcatgtga    7320
gcaaaaggcc agcaaaggcc caggaaccgt aaaaaggccg cgttgctggc gttttccat    7380 aggctccgcc ccctgacga gcatcacaaa aatcgacgct caagtcagag gtggcgaaac    7440
ccgacaggac tataaagata ccaggcgttt ccccctggaa gctccctcgt gcgctctcct    7500
gttccgaccc tgccgcttac cggatacctg tccgccttc tcccttcggg aagcgtggcg    7560
ctttctcata gctcacgctg taggtatctc agttcggtgt aggtcgttcg ctccaagctg    7620
ggctgtgtgc acgaacccc cgttcagccc gaccgctgcg ccttatccgg taactatcgt    7680
cttgagtcca acccggtaag acacgactta tcgccactgg cagcagccac tggtaacagg    7740
attagcagag cgaggtatgt aggcggtgct acagagttct tgaagtggtg gcctaactac    7800
ggctacacta gaagaacagt atttggtatc tgcgctctgc tgaagccagt taccttcgga    7860
aaaagagttg gtagctcttg atccggcaaa caaaccaccg ctggtagcgg tggttttttt    7920
gtttgcaagc agcagattac gcgcagaaaa aaaggatctc aagaagatcc tttgatcttt    7980
tctacggggt ctgacgctca gtggaacgaa aactcacgtt aagggatttt ggtcatgaga    8040
ttatcaaaaa ggatcttcac ctagatcctt ttaaattaaa aatgaagttt taaatcaatc    8100
taaagtatat atgagtaaac ttggtctgac agttaccaat gcttaatcag tgaggcacct    8160
atctcagcga tctgtctatt tcgttcatcc atagttgcct gactccccgt cgtgtagata    8220
actacgatac gggagggctt accatctggc cccagtgctg caatgatacc gcgagaccca    8280
cgctcaccgg ctccagattt atcagcaata aaccagccag ccggaagggc cgagcgcaga    8340
agtggtcctg caactttatc cgcctccatc cagtctatta attgttgccg ggaagctaga    8400
gtaagtagtt cgccagttaa tagtttgcgc aacgttgttg ccattgctac aggcatcgtg    8460
gtgtcacgct cgtcgtttgg tatggcttca ttcagctccg gttcccaacg atcaaggcga    8520
gttacatgat cccccatgtt gtgcaaaaaa gcggttagct ccttcggtcc tccgatcgtt    8580
```

| | |
|---|---:|
| gtcagaagta agttggccgc agtgttatca ctcatggtta tggcagcact gcataattct | 8640 |
| cttactgtca tgccatccgt aagatgcttt tctgtgactg gtgagtactc aaccaagtca | 8700 |
| ttctgagaat agtgtatgcg gcgaccgagt tgctcttgcc cggcgtcaat acgggataat | 8760 |
| accgcgccac atagcagaac tttaaaagtg ctcatcattg gaaaacgttc ttcggggcga | 8820 |
| aaactctcaa ggatcttacc gctgttgaga tccagttcga tgtaacccac tcgtgcaccc | 8880 |
| aactgatctt cagcatcttt tactttcacc agcgtttctg ggtgagcaaa aacaggaagg | 8940 |
| caaaatgccg caaaaaaggg aataagggcg acacggaaat gttgaatact catactcttc | 9000 |
| cttttttcaat attattgaag catttatcag ggttattgtc tcatgagcgg atacatattt | 9060 |
| gaatgtattt agaaaaataa acaaataggg gttccgcgca catttccccg aaaagtgcca | 9120 |
| cctgac | 9126 |

<210> SEQ ID NO 56
<211> LENGTH: 7829
<212> TYPE: DNA
<213> ORGANISM: Artificial Sequence
<220> FEATURE:
<223> OTHER INFORMATION: Synthesized - Vector sequence

<400> SEQUENCE: 56

| | |
|---|---:|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt cgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |

```
aaagtaagac caccgcacag caagcggccg gccgctgatc ttcagacctg gaggaggaga   1560
tatgagggac aattggagaa gtgaattata taaatataaa gtagtaaaaa ttgaaccatt   1620
aggagtagca cccaccaagg caaagagaag agtggtgcag agagaaaaaa gagcagtggg   1680
aataggagct ttgttccttg ggttcttggg agcagcagga agcactatgg gcgcagcgtc   1740
aatgacgctg acggtacagg ccagacaatt attgtctggt atagtgcagc agcagaacaa   1800
tttgctgagg gctattgagg cgcaacagca tctgttgcaa ctcacagtct ggggcatcaa   1860
gcagctccag gcaagaatcc tggctgtgga agatacctaa aggatcaac agctcctggg    1920 gatttggggt tgctctggaa aactcatttg caccactgct gtgccttgga atgctagttg   1980
gagtaataaa tctctggaac agatttggaa tcacacgacc tggatggagt gggacagaga   2040
aattaacaat tacacaagct taatacactc cttaattgaa gaatcgcaaa accagcaaga   2100
aaagaatgaa caagaattat tggaattaga taaatgggca agtttgtgga attggtttaa   2160
cataacaaat tggctgtggt atataaaatt attcataatg atagtaggag gcttggtagg   2220
tttaagaata gttttgctg tactttctat agtgaataga gttaggcagg gatattcacc    2280
attatcgttt cagacccacc tcccaacccc gaggggaccc gacaggcccg aaggaataga   2340
agaagaaggt ggagagagag acagagacag atccattcga ttagtgaacg gatcggcact   2400
gcgtgcgcca attctgcaga caaatggcag tattcatcca caatttttaaa agaaaagggg   2460 ggattggggg gtacagtgca ggggaaagaa tagtagacat aatagcaaca gacatacaaa   2520
ctaaagaatt acaaaaacaa attacaaaaa ttcaaaattt tcgggtttat tacagggaca   2580
gcagagatcc agtttggtta gtaccgggcc cgctctagcg tgaggctccg gtgcccgtca   2640
gtgggcagag cgcacatcgc ccacagtccc cgagaagttg gggggagggg tcggcaattg   2700
aaccggtgcc tagagaaggt ggcgcggggt aaactgggaa agtgatgtcg tgtactggct   2760
ccgccttttt cccgagggtg ggggagaacc gtatataagt gcagtagtcg ccgtgaacgt   2820
tctttttcgc aacgggtttg ccgccagaac acaggtaagt gccgtgtgtg gttcccgcgg   2880
gcctggcctc tttacgggtt atggcccttg cgtgccttga attacttcca cctggctgca   2940
gtacgtgatt cttgatcccg agcttcgggt tggaagtggg tgggagagtt cgaggccttg   3000
cgcttaagga gccccttcgc ctcgtgcttg agttgaggcc tggcctgggc gctggggccg   3060
ccgcgtgcga atcggtggc accttcgcgc ctgtctcgct gctttcgata agtctctagc    3120
catttaaaat ttttgatgac ctgctgcgac gcttttttttc tggcaagata gtcttgtaaa   3180
tgcgggccaa gatctgcaca ctggtatttc ggttttttggg gccgcgggcg gcgacggggc   3240
ccgtgcgtcc cagcgcacat gttcggcgag gcggggcctg cgagcgcggc caccgagaat   3300
cggacggggg tagtctcaag ctggccgcc tgctctggtg cctggcctcg cgccgccgtg    3360
tatcgccccg ccctgggcgg caaggctggc ccggtcggca ccagttgcgt gagcggaaag   3420
atggccgctt cccggccctg ctgcaggag ctcaaaatgg aggacgcggc gctcgggaga    3480
gcgggcgggt gagtcaccca cacaaaggaa aagggccttt ccgtcctcag ccgtcgcttc   3540
atgtgactcc acggagtacc gggcgccgtc caggcacctc gattagttct cgagcttttg   3600
gagtacgtcg tctttaggtt ggggggaggg gttttatgcg atggagtttc cccacactga   3660
gtgggtggag actgaagtta ggccagcttg gcacttgatg taattctcct tggaatttgc   3720 ccttttttgag tttggatctt ggttcattct caagcctcag acagtggttc aaagtttttt   3780
tcttccattt caggtgtcgt gagcggccgc tgagttaact attctagagt acccgggcta   3840
```

-continued

```
gatggcattg cctgttacag ctctgctgct gcctctggct ctgcttctgc atgctgctag    3900
acctcaggtt cagctgcagc aatggggagc cggactgctg aagccttctg agacactgtc    3960
tctgacctgt gccgtcagcg gagtgtctct gcctgattac ggcgtgtcct ggatcagaca    4020
gcctcctggc aaaggactgg aatggctggg agtgatctgg ggcagcgaga caacctacta    4080
cagcagcagc ctgaagtccg tgaccatcat caaggacacc agcaagaacc agttcttcct    4140
gaagctgagc agcgtgacag ccgccgatac agccgtgtac tactgcgcca gacactacta    4200
ctacggcggc agctacgcca tggattattg gggccagggc accacagtga cagtttctag    4260
cggaggcgga ggaagtggcg gcggaggatc tggcggtggt ggttctgata tccagatgac    4320
acagagccct agcagcctgt ctgcctctgt gggcgataga gtgaccatta cctgtcgggc    4380
cagccaggac atctccaagt acctgaactg gtatcagcag aagcccggca aggcccctaa    4440
gctgctgatc taccacacaa gcagactgca cagcggcgtg ccaagcagat ttctggcag    4500 cggctctggc accgacttca ccttcaccat ttctagcctg cagcctgagg atatcgccac    4560
ctactattgc cagcagggca cacccctgcc ttacaccttt ggcggaggca ccaaggtgga    4620
aatcaagacc accacaccag ctcctcggcc tccaactcct gctcctacaa ttgcctctca    4680
gcctctgagc ctgaggcctg aagcttgtag acctgctgct ggcggagccg tgcataccag    4740
aggactggat ttcgcctgcg acatcatctc attctttctg gccctgacca gcacagccct    4800 gctgttctg ctgttctttc tgacactgcg gttcagcgtg gtcaagcggg aagaaagaa    4860 gctgctgtac atcttcaagc agcccttcat gcggcccgtg cagacaacac aagaggaaga    4920
tggctgctcc tgcagattcc ccgaggaaga agaaggcggc tgcgagctga gagtgaagtt    4980
ctctagatct gccgacgctc ccgcctacca gcagggacag aatcagctgt acaacgagct    5040
gaatctgggg cgcagagaag agtacgacgt gctggataag agaagaggca gagatcccga    5100
gatgggcggc aagcctcgga gaaagaatcc tcaagagggc ctctacaatg agctgcagaa    5160
agacaagatg gccgaggcct acagcgagat cggaatgaag ggcgaacgca aagaggaaa    5220 gggccacgac ggactgtatc agggcctgag cacagccacc aaggatacct atgatgccct    5280
gcacatgcag gccctgcctc caagatgacg ataccgtcga cctcgatcga gcctagaaa    5340 aacatggagc aatcacaagt agcaatacag cagctaccaa tgctgattgt gcctggctag    5400
aagcacaaga ggaggaggag gtgggttttc cagtcacacc tcaggtacct ttaagaccaa    5460
tgacttacaa ggcagctgta gatcttagcc actttttaaa agaaagggg ggactggaag    5520 ggctaattca ctcccaacga agacaagata tccttgatct gtggatctac cacacacaag    5580
gctacttccc tgattggcag aactacacac cagggccagg gatcagatat ccactgacct    5640
ttggatggtg ctacaagcta gtaccagttg agcaagagaa ggtagaagaa gccaatgaag    5700
gagagaacac ccgcttgtta caccctgtga gcctgcatgg gatggatgac ccggagagag    5760
aagtattaga gtggaggttt gacagccgcc tagcatttca tcacatggcc cgagagctgc    5820
atccggactg tactgggtct ctctggttag accagatctg agcctgggag ctctctggct    5880
aactagggaa cccactgctt aagcctcaat aaagcttgcc ttgagtgctt caagtagtgt    5940
gtgcccgtct gttgtgtgac tctggtaact agagatccct cagacccttt tagtcagtgt    6000
ggaaaatctc tagcagcatg tgagcaaaag ccagcaaaa ggccaggaac cgtaaaaagg    6060
ccgcgttgct ggcgtttttc cataggctcc gccccctga cgagcatcac aaaaatcgac    6120
gctcaagtca gaggtggcga aacccgacag gactataaag ataccaggcg tttccccctg    6180
gaagctccct cgtgcgctct cctgttccga ccctgccgct taccggatac ctgtccgcct    6240
```

-continued

```
ttctcccttc gggaagcgtg gcgctttctc atagctcacg ctgtaggtat ctcagttcgg    6300
tgtaggtcgt tcgctccaag ctgggctgtg tgcacgaacc ccccgttcag cccgaccgct    6360
gcgccttatc cggtaactat cgtcttgagt ccaacccggt aagacacgac ttatcgccac    6420
tggcagcagc cactggtaac aggattagca gagcgaggta tgtaggcggt gctacagagt    6480
tcttgaagtg gtggcctaac tacggctaca ctagaagaac agtatttggt atctgcgctc    6540
tgctgaagcc agttaccttc ggaaaaagag ttggtagctc ttgatccggc aaacaaacca    6600
ccgctggtag cggtggtttt tttgtttgca agcagcagat tacgcgcaga aaaaaggat    6660 ctcaagaaga tcctttgatc ttttctacgg ggtctgacgc tcagtggaac gaaaactcac    6720
gttaagggat tttggtcatg agattatcaa aaaggatctt cacctagatc cttttaaatt    6780
aaaaatgaag ttttaaatca atctaaagta tatatgagta aacttggtct gacagttacc    6840
aatgcttaat cagtgaggca cctatctcag cgatctgtct atttcgttca tccatagttg    6900
cctgactccc cgtcgtgtag ataactacga tacgggaggg cttaccatct ggccccagtg    6960
ctgcaatgat accgcgagac ccacgctcac cggctccaga tttatcagca ataaaccagc    7020
cagccggaag ggccgagcgc agaagtggtc ctgcaacttt atccgcctcc atccagtcta    7080
ttaattgttg ccgggaagct agagtaagta gttcgccagt taatagtttg cgcaacgttg    7140
ttgccattgc tacaggcatc gtggtgtcac gctcgtcgtt tggtatggct tcattcagct    7200
ccggttccca acgatcaagg cgagttacat gatcccccat gttgtgcaaa aaagcggtta    7260
gctccttcgg tcctccgatc gttgtcagaa gtaagttggc cgcagtgtta tcactcatgg    7320
ttatggcagc actgcataat tctcttactg tcatgccatc cgtaagatgc ttttctgtga    7380
ctggtgagta ctcaaccaag tcattctgag aatagtgtat gcggcgaccg agttgctctt    7440
gcccggcgtc aatacgggat aataccgcgc cacatagcag aactttaaaa gtgctcatca    7500
ttggaaaacg ttcttcgggg cgaaaactct caaggatctt accgctgttg agatccagtt    7560
cgatgtaacc cactcgtgca cccaactgat cttcagcatc ttttactttc accagcgttt    7620
ctgggtgagc aaaaacagga aggcaaaatg ccgcaaaaaa gggaataagg gcgacacgga    7680
aatgttgaat actcatactc ttcctttttc aatattattg aagcatttat cagggttatt    7740
gtctcatgag cggatacata tttgaatgta tttagaaaaa taaacaaata ggggttccgc    7800
gcacatttcc ccgaaaagtg ccacctgac                                      7829
```

<210> SEQ ID NO 57
<211> LENGTH: 9135
<212> TYPE: DNA
<213> ORGANISM: Artificial Sequence
<220> FEATURE:
<223> OTHER INFORMATION: Synthesized - Artificial Sequence

<400> SEQUENCE: 57

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
```

-continued

```
tccattgacg tcaatgggtg gagtatttac ggtaaactgc ccacttggca gtacatcaag      480
tgtatcatat gccaagtacg cccctattg acgtcaatga cggtaaatgg cccgcctggc       540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga gaacttaga tcattatata atacagtagc aaccctctat tgtgtgcatc     1440
aaaggataga gataaaagac accaaggaag ctttagacaa gatagaggaa gagcaaaaca    1500
aaagtaagac caccgcacag caagcggccg gccgctgatc ttcagacctg gaggaggaga    1560
tatgagggac aattggagaa gtgaattata taaatataaa gtagtaaaaa ttgaaccatt    1620
aggagtagca cccaccaagg caaagagaag agtggtgcag agagaaaaaa gagcagtggg    1680
aataggagct ttgttccttg ggttcttggg agcagcagga agcactatgg gcgcagcgtc    1740
aatgacgctg acgtacagg ccagacaatt attgtctggt atagtgcagc agcagaacaa     1800
tttgctgagg gctattgagg cgcaacagca tctgttgcaa ctcacagtct ggggcatcaa    1860
gcagctccag gcaagaatcc tggctgtgga agataccta aaggatcaac agctcctggg    1920
gatttggggt tgctctggaa aactcatttg caccactgct gtgccttgga atgctagttg    1980
gagtaataaa tctctggaac agatttggaa tcacacgacc tggatggagt gggacagaga    2040
aattaacaat tacacaagct taatacactc cttaattgaa gaatcgcaaa accagcaaga    2100
aaagaatgaa caagaattat tggaattaga taaatgggca agtttgtgga attggtttaa    2160
cataacaaat tggctgtggt atataaaatt attcataatg atagtaggag gcttggtagg    2220
tttaagaata gtttttgctg tactttctat agtgaataga gttaggcagg gatattcacc    2280
attatcgttt cagacccacc tcccaacccc gaggggaccc gacaggcccg aaggaataga    2340
agaagaaggt ggagagagag acagagacag atccattcga ttagtgaacg gatcggcact    2400
gcgtgcgcca attctgcaga caaatggcag tattcatcca caattttaaa agaaaagggg    2460
ggattggggg gtacagtgca ggggaaagaa tagtagacat aatagcaaca gacatacaaa    2520
ctaaagaatt acaaaaacaa attacaaaaa ttcaaaattt tcgggtttat tacagggaca    2580
gcagagatcc agtttggtta gtaccgggcc cgctctagcg tgaggctccg gtgcccgtca    2640
gtgggcagag cgcacatcgc ccacagtccc cgagaagttg gggggagggg tcggcaattg    2700
aaccggtgcc tagagaaggt ggcgcggggt aaactgggaa agtgatgtcg tgtactggct    2760 ccgcctttt cccgagggtg ggggagaacc gtatataagt gcagtagtcg ccgtgaacgt     2820
```

```
tcttttcgc aacgggtttg ccgccagaac acaggtaagt gccgtgtgtg gttcccgcgg    2880
gcctggcctc tttacgggtt atggcccttg cgtgccttga attacttcca cctggctgca    2940
gtacgtgatt cttgatcccg agcttcgggt tggaagtggg tgggagagtt cgaggccttg    3000
cgcttaagga gccccttcgc ctcgtgcttg agttgaggcc tggcctgggc gctggggccg    3060
ccgcgtgcga atctggtggc accttcgcgc ctgtctcgct gctttcgata agtctctagc    3120
catttaaaat ttttgatgac ctgctgcgac gcttttttc tggcaagata gtcttgtaaa    3180
tgcgggccaa gatctgcaca ctggtatttc ggttttggg gccgcgggcg gcgacggggc    3240
ccgtgcgtcc cagcgcacat gttcggcgag gcggggcctg cgagcgcggc caccgagaat    3300
cggacggggg tagtctcaag ctggccggcc tgctctggtg cctggcctcg cgccgccgtg    3360
tatcgccccg ccctgggcgg caaggctggc ccggtcggca ccagttgcgt gagcggaaag    3420
atggccgctt cccggccctg ctgcaggag ctcaaaatgg aggacgcggc gctcgggaga    3480
gcgggcgggt gagtcaccca cacaaaggaa aagggccttt ccgtcctcag ccgtcgcttc    3540
atgtgactcc acggagtacc gggcgccgtc caggcacctc gattagttct cgagcttttg    3600
gagtacgtcg tctttaggtt ggggggaggg gttttatgcg atggagtttc cccacactga    3660
gtgggtggag actgaagtta ggccagcttg gcacttgatg taattctcct tggaatttgc    3720
cctttttgag tttggatctt ggttcattct caagcctcag acagtggttc aaagttttt    3780 tcttccattt caggtgtcgt gagcggccgc tgagttaact attatggccc tgcctgtgac    3840
agctctgctg ctgcctcttg ctctgcttct gcatgctgct agacctcagg ttcagctgca    3900
gcaatgggga ccggactgc tgaagccttc tgagacactg tctctgacct gtgccgtgta    3960
tggcgtgtcc ctgcctgatt acggcgtgtc ctggattaga cagcctcctg gcaaaggcct    4020
ggaatggctg ggagtgatct ggggcagcga gacaacctac tacagcagca gcctgaagtc    4080
cgtgaccatc agcgtggaca ccagcaagaa ccagttctcc ctgaagctgt ctagcgtgac    4140
agccgccgat accgccgtgt actactgtgc cagacactac tactacggcg gcagctacgc    4200
catggattat tggggccagg gcaccacagt gacagtttct gcggaggcg gaggaagtgg    4260 tggcggaggt tctggcggcg gaggatctga tatccagatg acacagagcc ctagcagcct    4320
gtctgcctct gtgggcgata gagtgaccat tacctgcaga gccagccagg acatcagcaa    4380
gtacctgaac tggtatcagc agaagcccgg caaggcccct aagctgctga tctaccacac    4440
aagcagactg cacagcggcg tgccaagcag attttctggc agcggctctg gcaccgactt    4500
caccttcacc atttctagcc tgcagcctga ggatatcgcc acctactatt gccagcaggg    4560
caacaccctg ccttacacct ttggcggagg caccaaggtg gaaatcaaga ccaccacacc    4620
agctcctcgg cctccaactc ctgctcctac aattgcctct cagcctctga gcctgaggcc    4680
tgaagcttgt agacctgctg ctggcggagc cgtgcatacc agaggactgg atttcgcctg    4740
cgacatcatc tcattctttc tggccctgac cagcacagcc ctgctgtttc tgctgttctt    4800
tctgacactg cggttcagcg tggtcaagcg gggcagaaag aagctgctgt acatcttcaa    4860
gcagcccttc atgcggcccg tgcagacaac acaagaggaa gatggctgct cctgcagatt    4920
ccccgaggaa gaagaaggcg gctgcgagct gagagtgaag ttctccagat ctgccgacgc    4980
tcctgcttat cagcagggcc agaaccagct gtacaacgag ctgaatctgg ggagaagaga    5040
agagtacgac gtgctggata gcggagagg cagagatcct gagatgggcg gcaagcccag    5100
acggaagaat cctcaagagg gcctgtataa tgagctgcag aaagacaaga tggccgaggc    5160
```

```
ctacagcgag atcggaatga agggcgagcg cagaagaggc aaaggacacg atggactgta      5220
ccagggcctg agcacagcca ccaaggatac ctatgatgcc ctgcacatgc aggccctgcc      5280
acctagataa gatccgcccc tctccctccc cccccctaa cgttactggc cgaagccgct       5340
tggaataagg ccggtgtgcg tttgtctata tgttattttc caccatattg ccgtcttttg      5400
gcaatgtgag ggcccggaaa cctggccctg tcttcttgac gagcattcct aggggtcttt      5460
ccctctcgc caaaggaatg caaggtctgt tgaatgtcgt gaaggaagca gttcctctgg       5520
aagcttcttg aagacaaaca acgtctgtag cgacccttg caggcagcgg aaccccccac       5580
ctggcgacag gtgcctctgc ggccaaaagc cacgtgtata agatacacct gcaaaggcgg      5640
cacaaccca gtgccacgtt gtgagttgga tagttgtgga aagagtcaaa tggctctcct       5700
caagcgtatt caacaagggg ctgaaggatg cccagaaggt accccattgt atgggatctg      5760
atctggggcc tcggtacaca tgctttacat gtgtttagtc gaggttaaaa aaacgtctag      5820
gcccccgaa ccacggggac gtggttttcc tttgaaaaac acgatgataa tatggccaca       5880
accatggtga gcaagggcga ggagctgttc accggggtgg tgcccatcct ggtcgagctg      5940
gacggcgacg taaacggcca caagttcagc gtgtccggcg agggcgaggg cgatgccacc      6000
tacggcaagc tgaccctgaa gttcatctgc accaccggca agctgcccgt gccctggccc      6060
accctcgtga ccaccctgac ctacggcgtg cagtgcttca gccgctaccc cgaccacatg      6120
aagcagcacg acttcttcaa gtccgccatg cccgaaggct acgtccagga gcgcaccatc      6180
ttcttcaagg acgacggcaa ctacaagacc cgcgccgagg tgaagttcga gggcgacacc      6240
ctggtgaacc gcatcgagct gaagggcatc gacttcaagg aggacggcaa catcctgggg      6300
cacaagctgg agtacaacta caacagccac aacgtctata tcatggccga caagcagaag      6360
aacggcatca aggtgaactt caagatccgc cacaacatcg aggacggcag cgtgcagctc      6420
gccgaccact accagcagaa cacccccatc ggcgacggcc ccgtgctgct gcccgacaac      6480
cactacctga gcacccagtc cgccctgagc aaagaccca acgagaagcg cgatcacatg       6540
gtcctgctgg agttcgtgac cgccgccggg atcactctcg gcatggacga gctgtacaag      6600
taaagcggcc gcatcgatac cgtcgacctc gatcgagacc tagaaaaaca tggagcaatc      6660
acaagtagca atacagcagc taccaatgct gattgtgcct ggctagaagc acaagaggag      6720
gaggaggtgg gttttccagt cacacctcag gtacctttaa gaccaatgac ttacaaggca      6780
gctgtagatc ttagccactt tttaaaagaa aaggggggac tggaagggct aattcactcc      6840
caacgaagac aagatatcct tgatctgtgg atctaccaca cacaaggcta cttccctgat      6900
tggcagaact acacaccagg gccagggatc agatatccac tgacctttgg atggtgctac      6960
aagctagtac cagttgagca agagaaggta gaagaagcca atgaaggaga acacccgc        7020
tgttacacc ctgtgagcct gcatgggatg gatgacccgg agagagaagt attagagtgg       7080
aggtttgaca gccgcctagc atttcatcac atggcccgag agctgcatcc ggactgtact      7140
gggtctctct ggttagacca gatctgagcc tgggagctct ctggctaact agggaaccca      7200
ctgcttaagc ctcaataaag cttgccttga gtgcttcaag tagtgtgtgc ccgtctgttg      7260
tgtgactctg gtaactagag atccctcaga cccttttagt cagtgtggaa aatctctagc      7320
agcatgtgag caaaaggcca gcaaaaggcc aggaaccgta aaaaggccgc gttgctggcg      7380
ttttccata ggctccgccc ccctgacgag catcacaaaa atcgacgctc aagtcagagg       7440
tggcgaaacc cgacaggact ataaagatac caggcgtttc ccctggaag ctccctcgtg       7500
cgctctcctg ttccgaccct gccgcttacc ggatacctgt ccgcctttct cccttcggga      7560
```

```
agcgtggcgc tttctcatag ctcacgctgt aggtatctca gttcggtgta ggtcgttcgc   7620
tccaagctgg gctgtgtgca cgaacccccc gttcagcccg accgctgcgc cttatccggt   7680
aactatcgtc ttgagtccaa cccggtaaga cacgacttat cgccactggc agcagccact   7740
ggtaacagga ttagcagagc gaggtatgta ggcggtgcta cagagttctt gaagtggtgg   7800
cctaactacg gctacactag aagaacagta tttggtatct gcgctctgct gaagccagtt   7860
accttcggaa aaagagttgg tagctcttga tccggcaaac aaaccaccgc tggtagcggt   7920 ggttttttg tttgcaagca gcagattacg cgcagaaaaa aaggatctca agaagatcct   7980
ttgatctttt ctacggggtc tgacgctcag tggaacgaaa actcacgtta agggattttg   8040
gtcatgagat tatcaaaaag gatcttcacc tagatccttt taaattaaaa atgaagtttt   8100
aaatcaatct aaagtatata tgagtaaact tggtctgaca gttaccaatg cttaatcagt   8160
gaggcaccta tctcagcgat ctgtctattt cgttcatcca tagttgcctg actccccgtc   8220
gtgtagataa ctacgatacg ggagggctta ccatctggcc ccagtgctgc aatgataccg   8280
cgagacccac gctcaccggc tccagattta tcagcaataa accagccagc cggaagggcc   8340
gagcgcagaa gtggtcctgc aactttatcc gcctccatcc agtctattaa ttgttgccgg   8400
gaagctagag taagtagttc gccagttaat agtttgcgca acgttgttgc cattgctaca   8460
ggcatcgtgg tgtcacgctc gtcgtttggt atggcttcat tcagctccgg ttcccaacga   8520
tcaaggcgag ttacatgatc ccccatgttg tgcaaaaaag cggttagctc cttcggtcct   8580
ccgatcgttg tcagaagtaa gttggccgca gtgttatcac tcatggttat ggcagcactg   8640
cataattctc ttactgtcat gccatccgta agatgctttt ctgtgactgg tgagtactca   8700
accaagtcat tctgagaata gtgtatgcgg cgaccgagtt gctcttgccc ggcgtcaata   8760
cgggataata ccgcgccaca tagcagaact ttaaaagtgc tcatcattgg aaaacgttct   8820
tcggggcgaa aactctcaag gatcttaccg ctgttgagat ccagttcgat gtaacccact   8880
cgtgcaccca actgatcttc agcatctttt actttcacca gcgtttctgg gtgagcaaaa   8940
acaggaaggc aaaatgccgc aaaaaaggga ataagggcga cacggaaatg ttgaatactc   9000
atactcttcc tttttcaata ttattgaagc atttatcagg gttattgtct catgagcgga   9060
tacatatttg aatgtattta gaaaaataaa caaataggg ttccgcgcac atttccccga   9120
aaagtgccac ctgac                                                    9135
```

<210> SEQ ID NO 58
<211> LENGTH: 119
<212> TYPE: PRT
<213> ORGANISM: Artificial Sequence
<220> FEATURE:
<223> OTHER INFORMATION: Synthesized - Humanized anti-CD19 binding
      domain heavy chain variable region

<400> SEQUENCE: 58

Gln Val Gln Leu Gln Gln Trp Gly Ala Gly Leu Leu Lys Pro Ser Glu
1               5                   10                  15

Thr Leu Ser Leu Thr Cys Ala Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Val Thr Ile Ile Lys Asp Thr Ser Lys Asn Gln Phe Phe Leu Lys

```
                65                  70                  75                  80
Leu Ser Ser Val Thr Ala Ala Asp Thr Ala Val Tyr Tyr Cys Ala Arg
                    85                  90                  95

His Tyr Tyr Gly Gly Ser Tyr Ala Met Asp Tyr Trp Gly Gln Gly
            100                 105                 110

Thr Thr Val Thr Val Ser Ser
        115

<210> SEQ ID NO 59
<211> LENGTH: 14
<212> TYPE: PRT
<213> ORGANISM: Artificial Sequence
<220> FEATURE:
<223> OTHER INFORMATION: Synthesized - Humanized anti-CD19 binding
      domain HCVR framework region 2

<400> SEQUENCE: 59

Trp Ile Arg Gln Pro Pro Gly Lys Gly Leu Glu Trp Ile Gly
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Synthesized - Humanized anti-CD19 binding
      domain HC CDR2

<400> SEQUENCE: 60

Val Ile Trp Gly Ser Glu Thr Thr Tyr Tyr Asn Ser Ala Leu Lys Ser
1               5                   10                  15

<210> SEQ ID NO 61
<211> LENGTH: 488
<212> TYPE: PRT
<213> ORGANISM: Artificial Sequence
<220> FEATURE:
<223> OTHER INFORMATION: Synthesized - Humanized anti-CD19 CAR amino
      acid sequence

<400> SEQUENCE: 61

Met Ala Leu Pro Val Thr Ala Leu Leu Leu Pro Leu Ala Leu Leu Leu
1               5                   10                  15

His Ala Ala Arg Pro Gln Val Gln Leu Gln Gln Trp Gly Ala Gly Leu
            20                  25                  30

Leu Lys Pro Ser Glu Thr Leu Ser Leu Thr Cys Ala Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ala Leu Lys Ser Val Thr Ile Ile Lys Asp Thr Ser Lys Asn
                85                  90                  95

Gln Phe Phe Leu Lys Leu Ser Ser Val Thr Ala Ala Asp Thr Ala Val
            100                 105                 110

Tyr Tyr Cys Ala Arg His Tyr Tyr Gly Gly Ser Tyr Ala Met Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Gln Met Thr
145                 150                 155                 160
```

```
Gln Ser Pro Ser Ser Leu Ser Ala Ser Val Gly Asp Arg Val Thr Ile
            165                 170                 175
Thr Cys Arg Ala Ser Gln Asp Ile Ser Lys Tyr Leu Asn Trp Tyr Gln
        180                 185                 190
Gln Lys Pro Gly Lys Ala Pro Lys Leu Leu Ile Tyr His Thr Ser Arg
    195                 200                 205
Leu His Ser Gly Val Pro Ser Arg Phe Ser Gly Ser Gly Ser Gly Thr
210                 215                 220
Asp Phe Thr Phe Thr Ile Ser Ser Leu Gln Pro Glu Asp Ile Ala Thr
225                 230                 235                 240
Tyr Tyr Cys Gln Gln Gly Asn Thr Leu Pro Tyr Thr Phe Gly Gly Gly
            245                 250                 255
Thr Lys Val Glu Ile Lys Thr Thr Thr Pro Ala Pro Arg Pro Pro Thr
        260                 265                 270
Pro Ala Pro Thr Ile Ala Ser Gln Pro Leu Ser Leu Arg Pro Glu Ala
    275                 280                 285
Cys Arg Pro Ala Ala Gly Gly Ala Val His Thr Arg Gly Leu Asp Phe
290                 295                 300
Ala Cys Asp Ile Ile Ser Phe Phe Leu Ala Leu Thr Ser Thr Ala Leu
305                 310                 315                 320
Leu Phe Leu Leu Phe Phe Leu Thr Leu Arg Phe Ser Val Val Lys Arg
            325                 330                 335
Gly Arg Lys Lys Leu Leu Tyr Ile Phe Lys Gln Pro Phe Met Arg Pro
        340                 345                 350
Val Gln Thr Thr Gln Glu Glu Asp Gly Cys Ser Cys Arg Phe Pro Glu
    355                 360                 365
Glu Glu Glu Gly Gly Cys Glu Leu Arg Val Lys Phe Ser Arg Ser Ala
370                 375                 380
Asp Ala Pro Ala Tyr Gln Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
            405                 410                 415
Arg Asp Pro Glu Met Gly Gly Lys Pro Arg Arg Lys Asn Pro Gln Glu
        420                 425                 430
Gly Leu Tyr Asn Glu Leu Gln Lys Asp Lys Met Ala Glu Ala Tyr Ser
    435                 440                 445
Glu Ile Gly Met Lys Gly Glu Arg Arg Arg Gly Lys Gly His Asp Gly
450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg
            485

<210> SEQ ID NO 62
<211> LENGTH: 1458
<212> TYPE: DNA
<213> ORGANISM: Artificial Sequence
<220> FEATURE:
<223> OTHER INFORMATION: Synthesized - Humanized anti-CD19 CAR
      nucleotide sequence

<400> SEQUENCE: 62
atggccctgc ctgtgacagc tctgctgctg cctcttgctc tgcttctgca tgctgctaga      60
cctcaggttc agctgcagca atggggagcc ggactgctga agccttctga gacactgtct     120
```

```
ctgacctgtg ccgtcagcgg agtgtctctg cctgattacg gcgtgtcctg gatcagacag      180
cctcctggca aaggcctgga atggatcgga gtgatctggg gcagcgagac aacctactac      240
aacagcgccc tgaagtccgt gaccatcatc aaggacacca gcaagaacca gttcttcctg      300
aagctgagca gcgtgacagc cgccgataca gccgtgtact actgcgccag acactactac      360
tacggcggca gctacgccat ggattattgg ggccagggca ccacagtgac agtttctagc      420
ggaggcggag aagtggtgg cggaggttct ggcggcggag gatctgatat ccagatgaca       480
cagagcccta gcagcctgtc tgcctctgtg ggcgatagag tgaccattac ctgcagagcc      540
agccaggaca tctccaagta cctgaactgg tatcagcaga agcccggcaa ggcccctaag      600
ctgctgatct accacacaag cagactgcac agcggcgtgc caagcagatt ttctggcagc      660
ggctctggca ccgacttcac cttcaccatt tctagcctgc agcctgagga tatcgccacc      720
tactactgcc agcagggcaa caccctgcct tacacatttg gcggaggcac caaggtggaa      780
atcaagacca ccacaccagc tcctcggcct ccaactcctg ctcctacaat tgcctctcag      840
cctctgagcc tgaggcctga agcttgtaga cctgctgctg gcggagccgt gcataccaga      900
ggactggatt tcgcctgcga catctacatt tgggccctc tggctggaac atgtggcgtg       960
ctgctgctga gcctggtcat caccctgtac tgcaagcggg gcagaaagaa gctgctgtac     1020
atcttcaagc agcccttcat gcggcccgtg cagacaacac aagaggaaga tggctgctcc     1080
tgcagattcc ccgaggaaga agaaggcggc tgcgagctga gagtgaagtt ctccagatct     1140
gccgacgctc ctgcctatca gcagggccag aatcagctgt acaacgagct gaatctgggg     1200
cgcagagaag agtacgacgt gctggacaag agaaggggca gagatcctga gatgggcggc     1260
aagcccagac ggaagaatcc tcaagagggc ctgtataatg agctgcagaa agacaagatg     1320
gccgaggcct acagcgagat cggaatgaag ggcgaacgca agaggcaa gggccacgat      1380 ggactgtatc agggcctgag cacagccacc aaggatacct atgatgccct gcacatgcag     1440
gccctgccac ctagataa                                                   1458
```

<210> SEQ ID NO 63
<211> LENGTH: 357
<212> TYPE: DNA
<213> ORGANISM: Artificial Sequence
<220> FEATURE:
<223> OTHER INFORMATION: Synthesized - Humanized anti-CD19 binding
      domain heavy chain variable region

<400> SEQUENCE: 63

```
caggttcagc tgcagcaatg gggagccgga ctgctgaagc cttctgagac actgtctctg       60
acctgtgccg tcagcggagt gtctctgcct gattacggcg tgtcctggat cagacagcct      120
cctggcaaag gcctggaatg gatcggagtg atctggggca gcgagacaac ctactacaac      180
agcgccctga agtccgtgac catcatcaag gacaccagca agaaccagtt cttcctgaag      240
ctgagcagcg tgacagccgc cgatacagcc gtgtactact gcgccagaca ctactactac      300
ggcggcagct acgccatgga ttattggggc cagggcacca cagtgacagt ttctagc        357
```

<210> SEQ ID NO 64
<211> LENGTH: 9126
<212> TYPE: DNA
<213> ORGANISM: Artificial Sequence
<220> FEATURE:
<223> OTHER INFORMATION: Synthesized - Vector sequence

<400> SEQUENCE: 64

-continued

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ccgctgatc ttcagacctg gaggaggaga     1560
tatgagggac aattggagaa gtgaattata taaatataaa gtagtaaaaa ttgaaccatt    1620
aggagtagca cccaccaagg caaagagaag agtggtgcag agagaaaaaa gagcagtggg    1680
aataggagct ttgttccttg ggttcttggg agcagcagga agcactatgg gcgcagcgtc    1740
aatgacgctg acggtacagg ccagacaatt attgtctggt atagtgcagc agcagaacaa    1800
tttgctgagg gctattgagg cgcaacagca tctgttgcaa ctcacagtct ggggcatcaa    1860
gcagctccag gcaagaatcc tggctgtgga agatacccta aaggatcaac agctcctggg    1920
gatttggggt tgctctggaa aactcatttg caccactgct gtgccttgga atgctagttg    1980
gagtaataaa tctctggaac agatttgaa tcacacgacc tggatggagt gggacagaga    2040
aattaacaat tacacaagct taatacactc cttaattgaa gaatcgcaaa accagcaaga    2100
aaagaatgaa caagaattat tggaattaga taaatgggca agtttgtgga attggtttaa    2160
cataacaaat tggctgtggt atataaaatt attcataatg atagtaggag gcttggtagg    2220
tttaagaata gttttttgctg tactttctat agtgaataga gttaggcagg gatattcacc    2280
attatcgttt cagacccacc tcccaacccc gaggggaccc gacaggcccg aaggaataga    2340
agaagaaggt ggagagagag acagagacag atccattcga ttagtgaacg gatcggcact    2400
```

```
gcgtgcgcca attctgcaga caaatggcag tattcatcca caattttaaa agaaaagggg    2460
ggattggggg gtacagtgca ggggaaagaa tagtagacat aatagcaaca gacatacaaa    2520
ctaaagaatt acaaaaacaa attacaaaaa ttcaaaattt tcgggtttat tacagggaca   2580
gcagagatcc agtttggtta gtaccgggcc cgctctagcg tgaggctccg gtgcccgtca    2640
gtgggcagag cgcacatcgc ccacagtccc cgagaagttg ggggaggggt cggcaattg    2700 aaccggtgcc tagagaaggt ggcgcggggt aaactgggaa agtgatgtcg tgtactggct    2760
ccgccttttt cccgagggtg ggggagaacc gtatataagt gcagtagtcg ccgtgaacgt    2820 tcttttcgc aacgggtttg ccgccagaac acaggtaagt gccgtgtgtg gttcccgcgg     2880
gcctggcctc tttacgggtt atggcccttg cgtgccttga attacttcca cctggctgca    2940
gtacgtgatt cttgatcccg agcttcgggt tggaagtggg tgggagagtt cgaggccttg    3000
cgcttaagga gccccttcgc ctcgtgcttg agttgaggcc tggcctgggc gctggggccg    3060
ccgcgtgcga atctggtggc accttcgcgc ctgtctcgct gctttcgata agtctctagc    3120
catttaaaat ttttgatgac ctgctgcgac gcttttttc tggcaagata gtcttgtaaa     3180
tgcgggccaa gatctgcaca ctggtatttc ggttttggg gccgcgggcg gcgacggggc      3240
ccgtgcgtcc cagcgcacat gttcggcgag gcggggcctg cgagcgcggc caccgagaat    3300
cggacggggg tagtctcaag ctggccggcc tgctctggtg cctggcctcg cgccgccgtg    3360
tatcgccccg ccctgggcgg caaggctggc ccggtcggca ccagttgcgt gagcggaaag    3420
atggccgctt cccggccctg ctgcaggag ctcaaaatgg aggacgcggc gctcgggaga      3480
gcgggcgggt gagtcaccca cacaaaggaa aagggccttt ccgtcctcag ccgtcgcttc    3540
atgtgactcc acgagtacc gggcgccgtc caggcacctc gattagttct cgagcttttg     3600
gagtacgtcg tctttaggtt gggggagggg gttttatgcg atggagtttc cccacactga    3660
gtgggtggag actgaagtta ggccagcttg gcacttgatg taattctcct tggaatttgc    3720 ccttttttgag tttggatctt ggttcattct caagcctcag acagtggttc aaagttttt    3780 tcttccattt caggtgtcgt gagcggccgc tgagttaact attatggccc tgcctgtgac    3840
agctctgctg ctgcctcttg ctctgcttct gcatgctgct agacctcagg ttcagctgca    3900
gcaatgggga gccggactgc tgaagccttc tgagacactg tctctgacct gtgccgtcag    3960
cggagtgtct ctgcctgatt acggcgtgtc ctggatcaga cagcctcctg gcaaaggcct    4020
ggaatggatc ggagtgatct ggggcagcga gacaacctac tacaacagcg ccctgaagtc    4080
cgtgaccatc atcaaggaca ccagcaagaa ccagttcttc ctgaagctga gcagcgtgac    4140
agccgccgat acagccgtgt actactgcgc cagacactac tactacggcg gcagctacgc    4200
catggattat tggggccagg gcaccacagt gacagtttct gcggaggcg gaggaagtgg     4260 tggcggaggt tctggcggcg gaggatctga tatccagatg acacagagcc ctagcagcct    4320
gtctgcctct gtgggcgata gagtgaccat tacctgcaga gccagccagg acatctccaa    4380
gtacctgaac tggtatcagc agaagcccgg caaggcccct aagctgctga tctaccacac    4440
aagcagactg cacagcggcg tgccaagcag attttctggc agcggctctg gcaccgactt    4500
caccttcacc atttctagcc tgcagcctga ggatatcgcc acctactact gccagcaggg    4560
caacaccctg ccttacacat ttggcggagg caccaaggtg gaaatcaaga ccaccacacc    4620
agctcctcgg cctccaactc ctgctcctac aattgcctct cagcctctga gcctgaggcc    4680
tgaagcttgt agacctgctg ctggcggagc cgtgcatacc agaggactgg atttcgcctg    4740
```

```
cgacatctac atttgggccc ctctggctgg aacatgtggc gtgctgctgc tgagcctggt    4800
catcaccctg tactgcaagc ggggcagaaa gaagctgctg tacatcttca agcagccctt    4860
catgcggccc gtgcagacaa cacaagagga agatggctgc tcctgcagat tccccgagga    4920
agaagaaggc ggctgcgagc tgagagtgaa gttctccaga tctgccgacg ctcctgccta    4980
tcagcagggc cagaatcagc tgtacaacga gctgaatctg gggcgcagag aagagtacga    5040
cgtgctggac aagagaaggg gcagagatcc tgagatgggc ggcaagccca gacggaagaa    5100
tcctcaagag ggcctgtata tgagctgcag gaaagacaag atggccgagg cctacagcga    5160
gatcggaatg aagggcgaac gcagaagagg caagggccac gatggactgt atcagggcct    5220
gagcacagcc accaaggata cctatgatgc cctgcacatg caggccctgc cacctagata    5280
agatccgccc ctctccctcc ccccccccta acgttactgg ccgaagccgc ttggaataag    5340
gccggtgtgc gtttgtctat atgttatttt ccaccatatt gccgtctttt ggcaatgtga    5400
gggcccggaa acctggccct gtcttcttga cgagcattcc tagggggtctt tcccctctcg    5460
ccaaaggaat gcaaggtctg ttgaatgtcg tgaaggaagc agttcctctg gaagcttctt    5520
gaagacaaac aacgtctgta gcgaccctt gcaggcagcg aaccccccca cctggcgaca    5580
ggtgcctctg cggccaaaag ccacgtgtat aagatacacc tgcaaaggcg cacaacccc    5640
agtgccacgt tgtgagttgg atagttgtgg aaagagtcaa atggctctcc tcaagcgtat    5700
tcaacaaggg gctgaaggat gcccagaagg tacccccattg tatgggatct gatctggggc    5760
ctcggtacac atgctttaca tgtgtttagt cgaggttaaa aaacgtctcta ggccccccga    5820
accacgggga cgtggttttc ctttgaaaaa cacgatgata atatgggccac aaccatggtg    5880
agcaagggcg aggagctgtt caccggggtg gtgcccatcc tggtcgagct ggacggcgac    5940
gtaaacggcc acaagttcag cgtgtccggc gagggcgagg gcgatgccac ctacggcaag    6000
ctgaccctga gttcatctg caccaccggc aagctgcccg tgccctggcc caccctcgtg    6060
accaccctga cctacggcgt gcagtgcttc agccgctacc ccgaccacat gaagcagcac    6120
gacttcttca gtccgccat gcccgaaggc tacgtccagg agcgcaccat cttcttcaag    6180
gacgacggca actacaagac ccgcgccgag gtgaagttcg agggcgacac cctggtgaac    6240
cgcatcgagc tgaagggcat cgacttcaag gaggacggca acatcctggg gcacaagctg    6300
gagtacaact acaacagcca caacgtctat atcatggccg acaagcagaa gaacggcatc    6360
aaggtgaact tcaagatccg ccacaacatc gaggacggca gcgtgcagct cgccgaccac    6420
taccagcaga cacccccat cggcgacggc cccgtgctgc tgcccgacaa ccactacctg    6480
agcacccagt ccgccctgag caaagacccc aacgagaagc gcgatcacat ggtcctgctg    6540
gagttcgtga ccgccgccgg gatcactctc ggcatggacg agctgtacaa gtaaagcggc    6600
cgcatcgata ccgtcgacct cgatcgagac ctagaaaaac atggagcaat cacaagtagc    6660
aatacagcag ctaccaatgc tgattgtgcc tggctagaag cacaagagga ggaggaggtg    6720
ggttttccag tcacacctca ggtacccttta agaccaatga cttacaaggc agctgtagat    6780
cttagccact ttttaaaaga aaagggggga ctggaaggggc taattcactc ccaacgaaga    6840
caagatatcc ttgatctgtg gatctaccac acacaaggct acttccctga ttggcagaac    6900
tacacaccag ggcagggat cagatatcca ctgacctttg gatggtgcta caagctagta    6960
ccagttgagc aagagaaggt agaagaagcc aatgaaggag agaacacccg cttgttacac    7020
cctgtgagcc tgcatgggat ggatgacccg gagagagaag tattagagtg gaggtttgac    7080
agccgcctag catttcatca catggcccga gagctgcatc cggactgtac tgggtctctc    7140
```

```
tggttagacc agatctgagc ctgggagctc tctggctaac tagggaaccc actgcttaag    7200
cctcaataaa gcttgccttg agtgcttcaa gtagtgtgtg cccgtctgtt gtgtgactct    7260
ggtaactaga gatccctcag acccttttag tcagtgtgga aaatctctag cagcatgtga    7320
gcaaaaggcc agcaaaaggc caggaaccgt aaaaaggccg cgttgctggc gttttttccat   7380 aggctccgcc cccctgacga gcatcacaaa aatcgacgct caagtcagag gtggcgaaac    7440
ccgacaggac tataaagata ccaggcgttt ccccctggaa gctccctcgt gcgctctcct    7500
gttccgaccc tgccgcttac cggatacctg tccgcctttc tcccttcggg aagcgtggcg    7560
ctttctcata gctcacgctg taggtatctc agttcggtgt aggtcgttcg ctccaagctg    7620
ggctgtgtgc acgaaccccc cgttcagccc gaccgctgcg ccttatccgg taactatcgt    7680
cttgagtcca acccggtaag acacgactta tcgccactgg cagcagccac tggtaacagg    7740
attagcagag cgaggtatgt aggcggtgct acagagttct tgaagtggtg cctaactac     7800 ggctacacta agaagaacagt atttggtatc tgcgctctgc tgaagccagt taccttcgga   7860
aaaagagttg gtagctcttg atccggcaaa caaaccaccg ctggtagcgg tggtttttttt  7920 gtttgcaagc agcagattac gcgcagaaaa aaaggatctc aagaagatcc tttgatcttt    7980
tctacggggt ctgacgctca gtggaacgaa aactcacgtt aagggatttt ggtcatgaga    8040
ttatcaaaaa ggatcttcac ctagatcctt ttaaattaaa aatgaagttt taaatcaatc    8100
taaagtatat atgagtaaac ttggtctgac agttaccaat gcttaatcag tgaggcacct    8160
atctcagcga tctgtctatt tcgttcatcc atagttgcct gactccccgt cgtgtagata    8220
actacgatac gggagggctt accatctggc cccagtgctg caatgatacc gcgagaccca    8280
cgctcaccgg ctccagattt atcagcaata accagccag ccggaagggc cgagcgcaga    8340
agtggtcctg caactttatc cgcctccatc cagtctatta attgttgccg ggaagctaga    8400
gtaagtagtt cgccagttaa tagtttgcgc aacgttgttg ccattgctac aggcatcgtg    8460
gtgtcacgct cgtcgtttgg tatggcttca ttcagctccg gttcccaacg atcaaggcga    8520
gttacatgat cccccatgtt gtgcaaaaaa gcggttagct ccttcggtcc tccgatcgtt    8580
gtcagaagta agttggccgc agtgttatca ctcatggtta tggcagcact gcataattct    8640
cttactgtca tgccatccgt aagatgcttt tctgtgactg gtgagtactc aaccaagtca    8700
ttctgagaat agtgtatgcg gcgaccgagt tgctcttgcc cggcgtcaat acgggataat    8760
accgcgccac atagcagaac tttaaaagtg ctcatcattg gaaaacgttc ttcggggcga    8820
aaactctcaa ggatcttacc gctgttgaga tccagttcga tgtaacccac tcgtgcaccc    8880
aactgatctt cagcatcttt tactttcacc agcgtttctg ggtgagcaaa aacaggaagg    8940
caaaatgccg caaaaaaggg aataagggcg acacggaaat gttgaatact catactcttc    9000 cttttttcaat attattgaag catttatcag ggttattgtc tcatgagcgg atacatattt    9060
gaatgtattt agaaaaataa acaaataggg gttccgcgca catttccccg aaaagtgcca    9120
cctgac                                                              9126
```

<210> SEQ ID NO 65
<211> LENGTH: 120
<212> TYPE: PRT
<213> ORGANISM: Artificial Sequence
<220> FEATURE:
<223> OTHER INFORMATION: Murine FMC63 heavy chain variable region

<400> SEQUENCE: 65

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser
                115             120

<210> SEQ ID NO 66
<211> LENGTH: 109
<212> TYPE: PRT
<213> ORGANISM: Artificial Sequence
<220> FEATURE:
<223> OTHER INFORMATION: Murine FMC63 light chain variable region

<400> SEQUENCE: 66

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Leu Leu Ile Tyr
            35                  40                  45

His Thr Ser Arg Leu His Ser Gly Val Pro Ser Arg Phe Ser Gly Ser
        50                  55                  60

Gly Ser Gly Thr Asp Tyr Ser Leu Thr Ile Ser Asn Leu Glu Gln Glu
65                  70                  75                  80

Asp Ile Ala Thr Tyr Phe Cys Gln Gln Gly Asn Thr Leu Pro Tyr Thr
                85                  90                  95

Phe Gly Gly Gly Thr Lys Leu Glu Ile Thr Arg Ala Asp
                100                 105
```

HUMANIZED ANTI-CD19 CHIMERIC ANTIGEN RECEPTOR, ITS NUCLEIC ACID SEQUENCE AND ITS PREPARATION

FIELD OF THE INVENTION

The present invention relates to novel humanized anti-CD19 chimeric antigen receptor containing an optimized anti-CD19 binding domain effective against the treatment of disease associated with expression of the Cluster of Differentiation 19 protein (CD19), and to a nucleic acid molecule encoding the humanized CAR. The invention also encompasses a process forth preparation of the CAR, composition containing the CAR, vectors containing the polynucleotide encoding the CAR and cells expressing the Carat their surface, in particular for their use in immunotherapy.

BACKGROUND OF THE INVENTION

Immunotherapy is emerging as a highly promising approach for the treatment of cancer. Genetically modifying T cells with chimeric antigen receptors (CARs) are a common approach to design tumor-specific T cells. CAR-T cells targeting tumor-associated antigens can be infused into patients (called adoptive T cell therapy) representing an efficient immunotherapy approach. The advantage of CAR-T technology compared with chemotherapy or antibody is that reprogrammed engineered T cells can proliferate and persist in the patient and work like a living drug.

CARs ordinarily consist of a monoclonal antibody-derived single-chain variable fragment (scFv) linked by a hinge and transmembrane domain to a variable number of intracellular signaling domains. CARs have successfully allowed T cells to be redirected against antigens expressed at the surface of tumor cells from various malignancies including lymphomas and solid tumors (Dotti, Gottschalk, Savoldo, & Brenner, 2014).

CD19 represents an attractive target for immunotherapy because the vast majority of B-acute lymphoblastic leukemia (B-ALL) uniformly express CD19, whereas expression is absent on non-hematopoietic cells, as well as myeloid, erythroid, and T cells, and bone marrow stem cells (Uckun et al., 1988).

Numerous groups from USA and Europe have generated anti-CD19CAR-T cells for the treatment of B cell malignancies. Multiple clinical trials were conducted by numerous scientific groups and biopharmaceuticals using anti-CD19CAR-T cells. The results from these trials have demonstrated remarkable success in long-term remission of CD19+B-cell ALL patients. These studies reported effective complete remission. These results are all the more remarkable as most of the patients eligible for early trials have failed several lines of chemotherapy, including stem cell transplant in few, and had less chances of survival (Kochenderfer et al., 2017; Maude et al., 2014; Park et al., 2018).

Recently, US Food and Drug Administration approved the anti-CD19 CAR T cells therapy developed by Prof. Carl June, and commercialized by Novartis (CTL019 or Kymriah) for the treatment of young and adults' relapse/refractory B-ALL. Currently approved CAR-T cell technology is tested and validated on patients who were either received the bone marrow transplantation (BMT) or were ineligible to BMT after multiple relapse (Maude et al., 2018).

However, the major disadvantage associated with the anti-CD 19 CAR therapies reported to date is that the T cells suffer from the problem of not surviving and remaining active in vivo for longer duration of time. Also, the potential risk associated with current anti-CD19 CARs are the generation of human anti-mouse immune responses which can induce significant toxicity associated with elevated levels of serum cytokines (Brudno & Kochenderfer, 2016). Further, it is also essential that the generated CAR-T cells remain active for longer duration and not induce toxicity.

Thus, there remains a need in the art for an improved anti-CD19 CARs for treatment of B-cell malignancies with improved efficacy and reduced toxicities.

SUMMARY OF THE INVENTION

Accordingly, in one aspect, the invention pertains to a recombinant nucleic acid molecule encoding a humanized chimeric antigen receptor (CAR), wherein the humanized CAR comprises:
(a) a single chain antibody or single chain antibody fragments comprising a humanized anti-CD19 binding domain;
(b) a hinge region;
(c) a transmembrane domain; and
(d) a cytoplasmic domain comprising a human 4-1BB costimulatory signaling domain and a CD3ζ signaling domain;

wherein said humanized anti-CD19 binding domain is scFv, and comprises a heavy chain framework region 1 (HFR1) of SEQ ID No: 4 or SEQ ID No: 5, a heavy chain framework region 2 (HFR2) of SEQ ID No: 7 or SEQ ID No: 59, a heavy chain framework region 3 (HFR3) of SEQ ID No: 9 or SEQ ID No: 10, a heavy chain framework region 4 (HFR4) of SEQ ID No: 12 and a light chain framework region 1 (LFR1) of SEQ ID No: 13, a light chain framework region 2 (LFR2) of SEQ ID No: 15, a light chain framework region 3 (LFR3) of SEQ ID No: 17 and a light chain framework region 4 (LFR4) of SEQ ID No: 19.

In an embodiment, the nucleic acid encodes a heavy chain complementary determining region 1 (HC CDR1) of SEQ ID No: 6, a heavy chain complementary determining region 2 (HC CDR2) of SEQ ID No: 8 or SEQ ID No: 60, a heavy chain complementary determining region 3 (HC CDR3) of SEQ ID No: 11 and a light chain complementary determining region 1 (LC CDR1) of SEQ ID No: 14, a light chain complementary determining region 2 (LC CDR2) of SEQ ID No: 16, and a light chain complementary determining region 3 (LC CDR3) of SEQ ID No: 18.

In an embodiment, the nucleic acid molecule encodes a heavy chain variable region (HCVR) selected from SEQ ID No: 1, SEQ ID No: 2 & SEQ ID No: 58 and a light chain variable region (LCVR) of SEQ ID No: 3.

In an embodiment, the nucleic acid molecule comprises a nucleic acid sequences encoding the HCVR and the LCVR, wherein the nucleic acid sequence encoding the HCVR comprises the nucleotide sequence selected from SEQ ID No. 35, SEQ ID No. 36 & SEQ ID No. 63, or nucleotide sequence with at least 95% identity thereof, and the nucleic acid sequence encoding the LCVR comprises the nucleotide sequence selected from SEQ ID No. 37, SEQ ID No. 50 and SEQ ID No. 51, or nucleotide sequence with at least 95% identity thereof.

In an embodiment, the encoded HCVR is attached to the encoded LCVR via a linker.

In an embodiment, the encoded linker comprises an amino acid sequence of SEQ ID No. 20.

In an embodiment, the nucleic acid molecule comprises a nucleic acid sequences encoding the linker, wherein the nucleic acid sequence encoding the linker comprises the nucleotide sequence selected from SEQ ID No. 43 and SEQ ID No. 46, or a nucleotide sequence with at least 95% identity thereof.

In an embodiment, the nucleic acid molecule encodes transmembrane domain comprising the amino acid sequence selected from SEQ ID No. 21 and SEQ ID No. 29.

In an embodiment, the nucleic acid molecule comprises a nucleic acid sequences encoding the transmembrane domain, wherein the nucleic acid sequence encoding the transmembrane domain comprises the nucleotide sequence selected from SEQ ID No. 39, SEQ ID No. 40 and SEQ ID No. 45, or a nucleotide sequence with at least 95% identity thereof.

In an embodiment, the encoded anti-CD19 binding domain is connected to the transmembrane domain by the hinge region.

In an embodiment, the encoded hinge region comprises the amino acid sequences of SEQ ID No. 22.

In an embodiment, the nucleic acid molecule comprises a nucleic acid sequences encoding the hinge region, wherein the nucleic acid sequence encoding the hinge region comprises the nucleotide sequence of SEQ ID No. 38, or a nucleotide sequence with at least 95% identity thereof.

In an embodiment, the nucleic acid molecule encodes costimulatory domain comprising the amino acid sequence of SEQ ID No. 23.

In an embodiment, the nucleic acid molecule comprises a nucleic acid sequences encoding the costimulatory domain, wherein the nucleic acid sequence encoding the costimulatory domain comprises the nucleotide sequence selected from SEQ ID No. 41 and SEQ ID No. 47, or a nucleotide sequence with at least 95% identity thereof.

In an embodiment, the nucleic acid molecule encodes signaling domain comprising the amino acid sequence of SEQ ID No. 24.

In an embodiment, the nucleic acid molecule comprises a nucleic acid sequences encoding the signaling domain, wherein the nucleic acid sequence encoding the signaling domain comprises the nucleotide sequence selected from SEQ ID No. 42, SEQ ID No. 48 and SEQ ID No. 49, or a nucleotide sequence with at least 95% identity thereof.

In an embodiment, the nucleic acid encodes humanized CAR further comprises a leader sequence.

In an embodiment, the encoded leader sequence comprises the amino acid sequences of SEQ ID No. 30.

In an embodiment, the nucleic acid molecule comprises a nucleic acid sequences encoding the leader sequence, wherein the nucleic acid sequence encoding the leader sequence comprises the nucleotide sequence selected from SEQ ID No. 31 and SEQ ID No. 44, or a nucleotide sequence with at least 95% identity thereof.

In an embodiment, the nucleic acid molecule comprises a nucleic acid sequence selected from SEQ ID No. 26, SEQ ID No. 28, SEQ ID No. 34, SEQ ID No. 53 & SEQ ID No. 63, or a nucleotide sequence with at least 95% identity thereof.

In an embodiment, the nucleic acid molecule comprises of nucleic acid sequence optimized for human codon usage selected from SEQ ID No. 26, SEQ ID No. 28, SEQ ID No. 34, SEQ ID No. 53 & SEQ ID No. 63, or a nucleotide sequence with at least 95% identity thereof.

In another aspect, the invention pertains to a humanized anti-CD19 chimeric antigen receptor (CAR) polypeptide, which comprises,
(a) a single chain antibody or single chain antibody fragments comprising a humanized anti-CD19 binding domain;
(b) a hinge region;
(c) a transmembrane domain; and
(d) a cytoplasmic domain comprising a human 4-1BB costimulatory signaling domain and a CD3ζ signaling domain;
wherein said humanized anti-CD19 binding domain is scFv, and comprises a heavy chain framework region 1 (HFR1) of SEQ ID No: 4 or SEQ ID No: 5, a heavy chain framework region 2 (HFR2) of SEQ ID No: 7 or SEQ ID No: 59, a heavy chain framework region 3 (HFR3) of SEQ ID No: 9 or SEQ ID No: 10, a heavy chain framework region 4 (HFR4) of SEQ ID No: 12 and a light chain framework region 1 (LFR1) of SEQ ID No: 13, a light chain framework region 2 (LFR2) of SEQ ID No: 15, a light chain framework region 3 (LFR3) of SEQ ID No: 17 and a light chain framework region 4 (LFR4) of SEQ ID No: 19.

In an embodiment, the anti-CD19 binding domain comprises a heavy chain complementary determining region 1 (HC CDR1) of SEQ ID No: 6, a heavy chain complementary determining region 2 (HC CDR2) of SEQ ID No: 8 or SEQ ID No: 60, a heavy chain complementary determining region 3 (HC CDR3) of SEQ ID No: 11 and a light chain complementary determining region 1 (LC CDR1) of SEQ ID No: 14, a light chain complementary determining region 2 (LC CDR2) of SEQ ID No: 16, and a light chain complementary determining region 3 (LC CDR3) of SEQ ID No: 18.

In an embodiment, the anti-CD19 binding domain comprises a heavy chain variable region (HCVR) selected from SEQ ID No: 1, SEQ ID No: 2 & SEQ ID No: 58, and a light chain variable region (LCVR) of SEQ ID No: 3.

In an embodiment, the heavy chain variable region is attached to the light chain variable region via a linker, comprising the amino acid of SEQ ID NO: 20.

In an embodiment, the transmembrane domain comprises the amino acid sequence selected from SEQ ID No. 21 and SEQ ID No. 29.

In an embodiment, the anti-CD19 binding domain is connected to the transmembrane domain by a hinge region comprising the amino acid sequences of SEQ ID No 22.

In an embodiment, the costimulatory domain comprises an amino acid sequence of SEQ ID NO: 23.

In an embodiment, the signaling domain comprises an amino acid sequence of SEQ ID NO: 24.

In an embodiment, the humanized anti-CD19CAR further contains a leader sequence comprising an amino acid sequence of SEQ ID No: 30.

In an embodiment, the CAR comprises an amino acid sequence selected from SEQ ID No. 25, SEQ ID No. 27, SEQ ID No. 33, SEQ ID No. 52 and SEQ ID No. 61.

In a further aspect, the invention pertains to a vector comprising the nucleic acid molecule encoding the humanized CAR according to the present invention.

In an embodiment, the vector is lentiviral vector.

In an embodiment, the vector further comprising a promoter, wherein the promoter is EF-1 alpha promoter comprising the nucleotide sequence of SEQ ID No. 32.

In an embodiment, the vector comprises the nucleotide sequence selected from SEQ ID No. 54, SEQ ID No. 55, SEQ ID No. 56, SEQ ID No. 57 & SEQ ID No. 64.

In an additional aspect, the invention pertains to an immune cell comprising the vector comprising the nucleic acid molecule encoding the humanized CAR according to the present invention.

In an embodiment, the immune cell is a human T lymphocyte including but not restricted to CD8+ and CD4+T lymphocyte and its possible subsets and NK cells.

In a further aspect, the invention pertains to a pharmaceutical composition comprising the nucleic acid molecule encoding the humanized CAR or the humanized CAR or the vector comprising the nucleic acid molecule encoding the CAR or the immune cell comprising the vector, with a pharmaceutically acceptable carrier, diluent or excipient, and optionally one or more further pharmaceutically active polypeptides and/or compounds.

In an additional aspect, the invention pertains to a method of making a humanized anti-CD19 CAR according to the present invention, comprising transducing a T cell with a vector comprising the nucleic acid molecule encoding the CAR.

In another aspect, the invention pertains to a method for preparing immune cells expressing a humanized anti-CD19CAR according to the present invention, comprising:
(i) providing a population of immune cells;
(ii) introducing into the immune cells a nucleic acid encoding the humanized CAR; and
(iii) culturing the immune cells under conditions allowing for expression of the chimeric receptor.

In an embodiment, the population of immune cells is derived from peripheral blood mononuclear cells (PBMC).

In an embodiment, the immune cells comprise of CD3+ and CD8+ and CD4+T lymphocyte and its possible subsets or natural killer cells.

In an embodiment, the immune cells are derived from a human cancer patient.

In another aspect, the invention pertains to method of treating a subject having a disease associated with expression of a CD19, comprising administering to the subject an effective amount of an immune effector cell according to the present invention.

In an embodiment, the disease associated with CD19 expression is selected from a proliferative disease, such as a cancer or malignancy or a precancerous conditions such as a myelodysplasia, a myelodysplastic syndrome or a preleukemia, or is a non-cancer related indication associated with expression of CD19.

In an embodiment, the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma.

In an embodiment, the cancer of B-cell origin is selected from the group consisting of B-lineage acute lymphoblastic leukemia, B-cell chronic lymphocytic leukemia, and B-cell non-Hodgkin's lymphoma including other CD19 positive malignancies.

In a further aspect, the invention pertains to the nucleic acid molecule, the humanized CAR, the vector or the cell according to the present invention, for use as a medicament.

In a further aspect, the invention pertains to the nucleic acid molecule, the humanized CAR, the vector or the cell according to the present invention, for use in the treatment of disease expressing CD19.

BRIEF DESCRIPTION OF THE DRAWINGS

The foregoing summary, as well as the following detailed description of the invention will be better understood when read in conjunction with the appended drawings. For the purpose of assisting in the explanation of the invention, there are shown in the drawings embodiments which are presently preferred and considered illustrative. It should be understood, however, that the invention is not limited to the precise arrangements and instrumentation shown therein.

DETAILED DESCRIPTION

Figure 1:
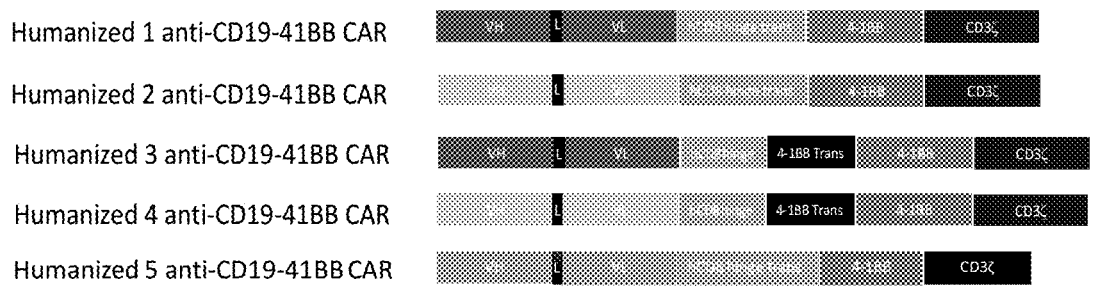
FIG. 1: Schematic representation of humanized anti-CD19 chimeric antigen receptor.
Figure 2:
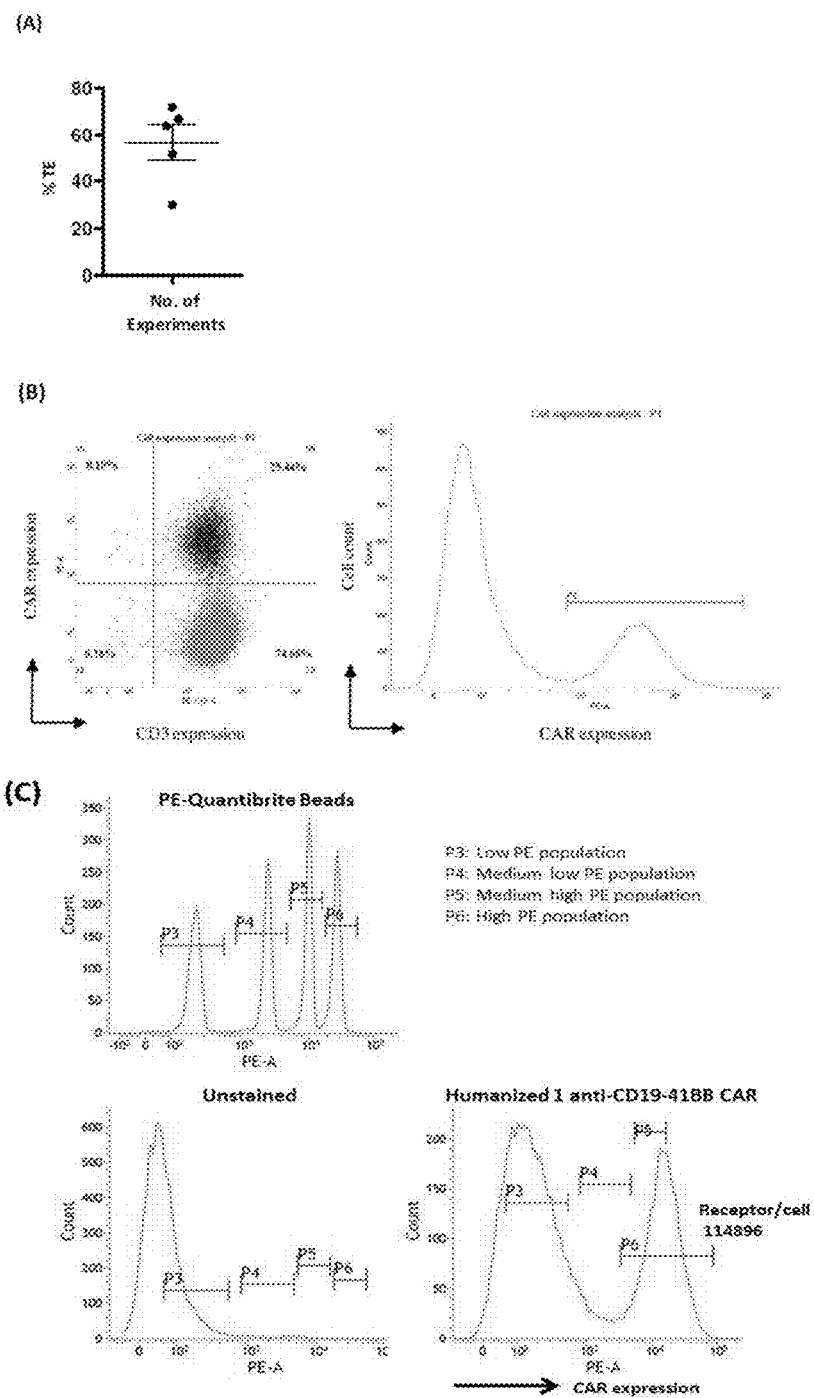
FIG. 2: Data of humanized anti-CD19 CAR from multiple experiments:
  The indigenous process of manufacturing humanized anti-CD19CAR according to the present invention provides highly efficacious CAR-T cells for CD19+B cell malignancies.
  (A) Depicts the percentage transduction efficiency/percentage of cells expressing humanized anti CD19 Chimeric Antigen Receptor generated from healthy donor T cells.
  (B) Determination of humanized anti CD19 Chimeric Antigen Receptor expression by flowcytometry.
  Left: Dot plot indicating the percentage of cells expressing humanized anti CD19Chimeric Antigen Receptor (upper right quadrant) gated against CD3 expression (Y-axis) as a marker for T cell.
  Right: Expression of humanized anti CD19 Chimeric Antigen Receptor in each cell as analysed by flowcytometry and represented in histogram.
  (C) Quantification of CAR receptor per cell by PE-quantibrite beads assay.

The present invention includes a recombinant nucleic acid molecule encoding a humanized chimeric antigen receptor (CAR) comprising a humanized anti-CD19 binding domain, which provides anti-tumor immunity against tumor cells expressing CD19. The present invention also includes the humanized chimeric antigen receptor (CAR) comprising a humanized anti-CD19 binding domain.

A Chimeric Antigen Receptor (CAR) comprises of an extracellular domain, an intracellular domain connected via a transmembrane domain. The extracellular domain is usually an antigen binding domain against a particular target antigen based on cancer type. The antigen binding domain is derived from a monoclonal antibody against the target antigen which helps in directing the anti-tumor response. The intracellular domain in CAR is usually derived from group of T cell receptors especially the cytoplasmic domain. This cytoplasmic domain primes the CAR expressing T cells against the target antigen recognition based on the extracellular domain. The membrane anchorage and joining of intracellular domain to extracellular domain is done by a transmembrane domain. A transmembrane domain is usually derived from a naturally occurring membrane protein or designed synthetically. All these domains individually or in combination have an impact on anti-tumor response, CAR T cell persistence, toxicity and thus determine the efficacy of CAR T cells (Alka, Atharva, Sarbari, Afrin, & Rahul, 2019).

For the purposes of the following detailed description, it is to be understood that the invention may assume various alternative variations and step sequences, except where expressly specified to the contrary. Thus, before describing the present invention in detail, it is to be understood that this invention is not limited to particularly exemplified process parameters that may of course, vary. It is also to be understood that the terminology used herein is for the purpose of describing particular embodiments of the invention only, and is not intended to limit the scope of the invention in any manner.

1. Humanized anti-CD19 Chimeric Antigen Receptor:

As described herein, the CAR according to the present invention comprises of a humanized CD19 binding domain which provides anti-tumor immunity against tumor cells expressing CD19. The humanized anti-CD19 chimeric antigen receptor (CAR) polypeptide, according to the present invention, comprises,
  (a) a single chain antibody or single chain antibody fragments comprising a humanized anti-CD19 binding domain;
  (b) a hinge region;
  (c) a transmembrane domain; and
  (d) a cytoplasmic domain comprising a human 4-1BB costimulatory signaling domain and a CD3ζ signaling domain;

a. Humanized Anti-CD19 Binding Domain

The antigen binding domain is an extracellular domain for the chimeric antigen receptor which governs the target antigen binding element. The current invention pertains to treat B cell malignancies preferably CD19 expressing B cell malignancies. Therefore, CD19 serves as an attractive target antigen for designing of antigen binding domain. The B-cell lineage throughout its maturation and development acquires various protein molecules expressed on its surface, one of it being CD19. It has been observed that CD19 antigen is expressed in all B-cell malignancies and absent on the hematopoietic stem cells (Uckun et al., 1988). Thus the CAR T cells directed against CD19 antigen would effectively kill the malignant cells with causing lesser toxicity for other population.

The antigen binding domain is constructed form murine monoclonal antibodies in many chimeric antigen receptors so far. The potential problem with use of murine monoclonal antibody is immunogenicity. The murine monoclonal antibodies can be recognized as foreign protein and an immune response can be mounted in the host body. This disadvantage might not allow the repeated infusion of chimeric antigen receptor expressing cells, leading to reactions like Human Anti-Mouse Antibody (HAMA) response (Maus et al., 2013)

In certain aspects, of this invention a chimeric antigen receptor contains all human genes to improve the efficacy and reduce toxicity and immunogenicity. The antigen binding domain described herein, recognizing CD19, is a humanized CD19 binding domain.

Humanization is a process by which xenogeneic antibody sequences are modified to reduce this immunogenicity and several approaches have been developed since the first approved humanized antibody in 1997 (Daclizumab) (Waldmann, 2007). In order to humanize an antibody/binding domain, it includes various critical choices including the extents of the CDRs, the human frameworks to use and the substitution of residues from the murine antibody into the human framework regions (Almagro & Fransson, 2008). There is no single parameter to decide the right choice of the heavy and light chain. However these choices can severely impact the safety, efficacy, toxicity and immunogenicity of the CAR T cells.

In one embodiment, the humanized anti-CD19 binding domain is designed from fragment of murine monoclonal antibody also called as single chain variable fragment (scFv) against CD19 as known in prior art. The CD19 binding domain contains complementarity determining region (CDRs) from the murine monoclonal antibody with or without modification and variable framework region (FRs) from the human origin. In an embodiment, the FRs is selected from VH4_34 and/or VH4_34 (I to L). The complementarity determining region is a sequence of amino acids present in an antibody which provides specificity for the target antigen. There are usually three CDRs (CDR1, CDR2, and CDR3) which in combination form a hypervariable region recognizing the target antigen.

The humanization of scFv is a complex process and simple grafting of the murine complementarity-determining regions (CDRs) into human frameworks does not always reconstitute the binding affinity and specificity of the murine anti-CD19 binding domain. The strategies involved in humanization of scFv are known to skilled artisan. The present approach uses human framework regions which show high amino acid similarity to the murine framework regions. The advantage is that hypervariable regions or CDRs are not affected, and unnecessary grafting and back mutations are avoided.

In one aspect, the humanized anti-CD19 binding domain comprises a heavy chain framework region 1 (HFR1) of SEQ ID No: 4 or SEQ ID No: 5, a heavy chain framework region 2 (HFR2) of SEQ ID No: 7 or SEQ ID No: 59, a heavy chain framework region 3 (HFR3) of SEQ ID No: 9 or SEQ ID No: 10, a heavy chain framework region 4 (HFR4) of SEQ ID No: 12 and a light chain framework region 1 (LFR1) of SEQ ID No: 13, a light chain framework region 2 (LFR2) of SEQ ID No: 15, a light chain framework region 3 (LFR3) of SEQ ID No: 17 and a light chain framework region 4 (LFR4) of SEQ ID No: 19.

In another aspect, the humanized anti-CD19 binding domain comprises a heavy chain complementary determining region 1 (HC CDR1) of SEQ ID No: 6, a heavy chain complementary determining region 2 (HC CDR2) of SEQ ID No: 8 or SEQ ID No: 60, a heavy chain complementary determining region 3 (HC CDR3) of SEQ ID No: 11 and a light chain complementary determining region 1 (LC CDR1) of SEQ ID No: 14, a light chain complementary determining region 2 (LC CDR2) of SEQ ID No: 16, and a light chain complementary determining region 3 (LC CDR3) of SEQ ID No: 18.

In further aspect, the humanized anti-CD19 binding domain comprises of variable heavy chain (VH) and variable light chain (VL) region. Preferably, the heavy chain variable region (VH) of the humanized anti-CD19 binding domain according to the present invention is configured such that amino acid sequences of FRs and CDRs have high identity to FRs of the human heavy chain sequence and CDRs of the murine heavy chain sequence, respectively. VH4-34 human germline heavy chain variable region was chosen as it has highest identity with the murine FMC63 (Table 1).

More preferably, the variable heavy chain of the humanized anti-CD19 binding domain according to the present invention is composed of a polypeptide including an amino acid sequence represented by SEQ ID NO: 1. However, the VH region is not limited thereto, and includes various variants derived from the amino acid sequence represented by SEQ ID NO: 2 and SEQ ID No: 58, while having both complementarity specific to T cells and the minimum antigenicity to a human immune system. In one embodiment, the VH region is encoded by nucleotide sequence selected from SEQ ID NO: 35 and SEQ ID No. 36, or nucleotide sequence with at least 95% identity thereof.

In a further aspect, the light chain variable region (VL) of the humanized anti-CD19 binding domain according to the present invention is configured such that amino acid sequences of FRs and CDRs have high identity to FRs of the human light chain sequence and CDRs of the murine light chain sequence, respectively. VK1-018 human germline light chain sequence was selected from Vbase database based on highest similarity with murine FMC63 light chain (Table 2). More preferably, the variable light chain of the humanized anti-CD19 binding domain according to the present invention is composed of a polypeptide including an amino acid sequence represented by SEQ ID NO: 3. In one embodiment, the VL region is encoded by nucleotide sequence selected from SEQ ID NO: 37, SEQ ID No. 50 and SEQ ID No. 51, or nucleotide sequence with at least 95% identity thereof.

The light chain variable region is attached to a heavy chain variable region, via a linker. The light chain variable region and heavy chain variable region of a scFv can be, e.g., in any of the following orientations: light chain variable region-linker-heavy chain variable region or heavy chain variable region-linker-light chain variable region. In one embodiment, the humanized anti-CD19 binding domain includes a (Gly$_4$-Ser) n linker, wherein n is 1, 2, 3, 4, 5, or 6, preferably 3, comprising the amino acid sequence of SEQ ID NO: 20. In an embodiment, the linker is encoded by nucleotide sequence selected from SEQ ID NO: 43 and SEQ ID No. 46, or nucleotide sequence with at least 95% identity thereof. In more specific embodiment, the humanized anti-CD19 binding domain is arranged in variable heavy chain region-linker-variable light chain region orientation.

b. Transmembrane Domain:

The transmembrane domain in the CAR helps for membrane anchorage of the antigen recognizing extracellular domain. The transmembrane domain is the connecting link between the extracellular domain and the intracellular domain of the CAR. The transmembrane domain of the CARs is usually chosen from Type I proteins such as CD3z, CD28, CD8α, CD4 and also other T cell related molecules like ICOS and 4-1BB. The choice of transmembrane domain has an impact on stability and functionality of the CAR and hence using different combination of transmembrane domain can change the potency of the CAR T cells (Guedan et al., 2018).

In this invention, the humanized anti-CD19 CAR described herein comprises of transmembrane domain. In one embodiment the transmembrane domain is derived from human CD8α comprising of amino acid from the sequence SEQ ID NO: 21. In one embodiment the CD8α transmembrane domain is encoded by nucleotide sequence selected from SEQ ID NO: 39 and SEQ ID No. 45, or nucleotide sequence with at least 95% identity thereof.

In another embodiment the transmembrane domain is derived from human 4-1BB comprising of amino acid from the sequence SEQ ID NO: 29. In one embodiment the 4-1BB transmembrane domain is encoded by nucleotide sequence comprising of SEQ ID NO: 40, or nucleotide sequence with at least 95% identity thereof.

The antigen binding domain of the chimeric antigen receptor is connected to the transmembrane domain directly or through a hinge domain. The hinge region provides flexibility and length to the CAR and hence affects its functionality (Qin et al., 2017). The choice of hinge region is made from T cell related molecules such as CD8α and/or from the immunoglobulin molecules such as IgG1, IgG2 and IgG4.

In this invention, the humanized anti-CD19 CAR described herein comprises of hinge region to connect the extracellular domain to the transmembrane domain. In one embodiment the hinge region is derived from human CD8α comprising of amino acid from the sequence SEQ ID NO: 22. In one embodiment the CD8α hinge region is encoded by nucleotide sequence comprising of SEQ ID NO: 38, or nucleotide sequence with at least 95% identity thereof.

c. Intracellular Domain:

The intracellular domain of the CAR provides the antitumor activity to the cells preferably T cells expressing it. The intracellular domain is derived from cytoplasmic domains of T cell receptor complex and other related receptor which play a role in the biological functions of the T cells. Therefore, intracellular domain usually plays a role in providing the effector function to the CAR T cells. After antigen recognition, receptors cluster and a signal is transmitted to the cell. The most commonly used endodomain component is that of CD3-zeta which contains 3 ITAMs. This transmits an activation signal to the T cell after antigen is bound. The T cell activation though occurs through T cell receptor signaling, an additional co-stimulatory activation is required for an enhanced T cell response. The intracellular domain in CARs usually comprises of a T cell receptor signaling domain CD3z and a cytoplasmic fragment of the costimulatory receptors. The cytoplasmic fragment can be selected from a group of receptors such as CD3z, CD28, 4-1BB, ICOS and OX40.

The choice of intracellular domain has an impact on the activation of signaling cascades in the T cells which confer the effector functions like the anti-tumor response, cytokine secretion and the T cell phenotype. In this invention, the humanized anti-CD19 CAR described herein comprises of intracellular domain. In one embodiment the cytoplasmic domain is derived from human CD3z comprising of amino acid from the sequence SEQ ID NO: 24. In one embodiment the CD3z cytoplasmic domain is encoded by nucleotide sequence selected from SEQ ID NO: 42, SEQ ID No. 48 and SEQ ID No. 49, or nucleotide sequence with at least 95% identity thereof. In one embodiment the co-stimulatory domain of cytoplasmic domain is derived from human 4-1BB comprising of amino acid from the sequence SEQ ID NO: 23. In one embodiment the 4-1BB co-stimulatory domain is encoded by nucleotide sequence selected from SEQ ID NO: 41 and SEQ ID No. 47, or nucleotide sequence with at least 95% identity thereof.

d. Leader Sequence

The humanized anti-CD19 chimeric antigen receptor polypeptide described herein comprises of a leader sequence at the amino terminal (N-ter). The leader sequence may comprise the amino acid sequence of SEQ ID No: 30 and is encoded by the nucleotide sequence selected from SEQ ID No. 31 and SEQ ID No. 44, or nucleotide sequence with at least 95% identity thereof.

e. CAR Polypeptide

The invention pertains to a novel anti-CD19 chimeric antigen receptor (CAR) polypeptide wherein the CAR comprises (a) a single chain antibody or single chain antibody fragments comprising a humanized anti-CD19 binding domain; (b) a hinge region; (c) a transmembrane domain; and (d) a cytoplasmic domain comprising a human 4-1BB costimulatory signaling domain and a CD32 signaling domain.

The humanized anti-CD19 chimeric antigen receptor thus is a combination of the humanized anti-CD19 binding domain in combination with the transmembrane and the intracellular domain as described herein. The humanized anti-CD19 chimeric antigen receptor polypeptide comprises of amino acid sequence selected from SEQ ID NO: 25, SEQ ID NO: 27, SEQ ID NO: 33, SEQ ID No. 52 and SEQ ID No. 61.

f. Nucleic Acid Sequence

The invention pertains to a nucleic acid sequence which codes for a humanized anti-CD19CAR of the present invention comprising (a) a single chain antibody or single chain antibody fragments comprising a humanized anti-CD19 binding domain; (b) a hinge region; (c) a transmembrane domain; and (d) a cytoplasmic domain comprising a human 4-1BB costimulatory signaling domain and a CD35 signaling domain.

In one aspect, the nucleic acid sequence may be capable of encoding a CAR having the amino acid sequence shown as any of SEQ ID NO: 25, SEQ ID NO: 27, SEQ ID NO: 33, SEQ ID No. 52 or SEQ ID No. 61. The nucleic acid sequence may encode the same amino acid sequence of the respective domain, but may have a different nucleic acid sequence, due to the degeneracy of the genetic code.

The nucleotide sequence of SEQ ID NO: 26, SEQ ID NO: 28, SEQ ID NO: 34, SEQ ID No. 53 & SEQ ID No. 62, encoding the humanized CAR, has been optimized for human codon usage to enhance the expression, efficacy and persistence of CAR T cells.

In another aspect, the nucleic acid sequence capable of encoding the humanized anti-CD19 CAR as described herein is encoded by nucleotide sequence selected from SEQ ID NO: 26, SEQ ID NO: 28, SEQ ID NO: 34, SEQ ID No. 53 & SEQ ID No. 62, or nucleotide sequence with at least 95% identity thereof.

g. Vector

A vector is a molecule which contains nucleotide sequence encoding humanized anti-CD19 CAR. In the invention described herein, the vector used is a lentiviral vector. Lentiviral vectors are known in art to facilitate long term stable gene transfer in the host cell and allowing its propagation in the daughter cells. The self-inactivating lentiviral vectors are more advantageous due to their capacity to accommodate larger gene of interest, can transduce non proliferating cells and possess low immunogenicity (Milone & O'Doherty, 2018). The strategies for packaging of desired nucleic acid into viral vectors preferably lentiviral vectors are known in the art. The lentiviral particles expressing the gene of interest can be harvested and used for transducing the cells ex vivo.

In one embodiment, the vector used for generation of humanized anti-CD19 CAR comprises of nucleotide sequence selected from SEQ ID NO: 26, SEQ ID NO: 28, SEQ ID NO: 34, SEQ ID No. 53 & SEQ ID No. 62. The nucleotide sequence of the CAR construct is cloned into an expression vector suitable for integration and stable expression in mammalian cells with techniques known in art. The CAR construct can also be synthesized chemically and cloned into the expression vector. The expression of CAR is under the control of a constitutive promoter usually derived from a mammalian cell. A promoter is a DNA sequence usually present upstream of the gene of interest which drives the expression of the target gene in the cells.

The choice of the promoter has an impact on the expression in a particular cell type and pertaining to this invention can have a role in determining the efficacy of the CAR. The promoter is chosen from a group of widely studied constitutive promoters from mammalian origin such as elongation factor-1 alpha (EF-1a) promoter, Ubiquitin-C (UbiC) promoter, and phosphoglycerate kinase (PGK) promoter or from promoters from the non-mammalian origin like immediate early cytomegalovirus (CMV) promoter and simian virus 40 (SV40) early promoter A strong promoter is required for enhanced expression of the gene of interest and use of different promoters described herein is been known in art to affect the expression of chimeric antigen receptor (Milone et al., 2009).

In one embodiment, the promoter chosen for expression of humanized anti-CD19 CAR comprises of EF-1a promoter encoded by the nucleotide sequence of SEQ ID No: 32.

Along with promoter, the vector comprising humanized anti-CD19 CAR also comprises of the termination sequences for transcription and translation and other non-coding sequences which regulate the expression of desired gene of interest. The non-coding sequences usually called introns also play a role in enhancing the gene expression in synergy with the promoter such as the EF-1a intron A (Kim, Lee, Shin, Kang, & Kim, 2002)

In one embodiment, the EF-1a promoter chosen for expression of humanized anti-CD19 CAR comprises of EF-1a intron A. The nucleotide sequence of EF-1a intron-A in the vector described herein comprises of nucleotide sequence of SEQ ID No: 32.

The vector encoding the gene of interest usually possesses a reporter gene which allows the identification of expression of the target gene in a particular host. The reporter genes are usually selectable markers like the enzymes providing resistance to antibiotics such as zeocin, bioluminescent proteins derived from organisms of lower order like firefly luciferase or a simple fluorescent proteins such as green fluorescent protein (GFP), red fluorescent protein (RFP) and others.

The expression vector encoding humanized anti-CD19 CAR possess an enhanced green fluorescent protein which allows detection of CAR expression in T cells using molecular biology and immunological assays known in the art.

In an embodiment, the vector comprises a nucleic acid sequence encoding promoter sequence. In a preferred embodiment, the promoter sequence is EF-1 alpha comprising the nucleotide sequence of SEQ ID No. 32.

In a further embodiment, the vector according to the present invention comprises the nucleotide sequence from SEQ ID No. 54, SEQ ID No. 55, SEQ ID No. 56 and SEQ ID No. 57, or nucleotide sequence with at least 95% identity thereof.

h. Immune Cell

The invention also provides immune cell which comprises a nucleic acid according to the invention. The immune cell may be capable of expressing a CAR according to the first aspect of the invention.

In a preferred embodiment, the immune cell may be a cytolytic immune cell such as a human T lymphocyte including but not restricted to CD8+ and CD4+T lymphocyte, and its possible subsets and NK cells.

In one embodiment, the immune cell expressing the humanized anti-CD19 CAR is preferably a human T cells. T cells are the cells of adaptive immune system which generate from pluripotent hematopoietic stem cells, migrate and mature in thymus to express the T cell receptor (TCR). The T cell receptor can recognize an antigen in conjugation with a major histocompatibility complex (MHC) which is displayed by antigen presenting cells. The TCR activated T cells are antigen primed and are signaled to generate cell mediated response. The chimeric antigen receptor expressing T cells are unique in a way to recognize cancer antigens without involvement of MHC molecule.

i. Pharmaceutical Composition

The present invention also relates to a pharmaceutical composition comprising the nucleic acid molecule encoding the humanized anti-CD19 CAR or the humanized CAR polypeptide or the vector comprising the nucleic acid molecule encoding the CAR or the immune cell comprising the vector, with a pharmaceutically acceptable carrier, diluent or excipient, and optionally one or more further pharmaceutically active polypeptides and/or compounds.

2. Method of Generation of Humanized Anti-CD19 CAR T Cells:

The invention includes methods of generation humanized anti-CD19 CAR T cells by using a vector encoding the humanized anti-CD19 CAR and its expansion into clinically meaningful numbers to be used as a therapy.

In another aspect, the invention pertains to method of transducing T cells with the vector encoding humanized anti-CD19 CAR.

Prior to the generation of humanized anti-CD19 CAR expressing T cells, human T cells are isolated from the healthy donors or beneficiary patients using the techniques known in art. The source of T cells can be peripheral blood, apheresis product or other tissues harboring these cells. In one embodiment, the T cells are isolated form the human peripheral blood by a technique known to a skilled artisan.

The peripheral blood mononuclear cells (PBMCs) are isolated using density gradient centrifugation by a self-forming gradient of Histopaque™. The PBMCs are washed with a suitable buffer such as phosphate buffer saline to clear impurities if any. A skilled artisan will appreciate the use of density gradient centrifugation and washing step can be performed using the techniques known in art.

The T cells from the PBMCs are activated and enriched using anti-CD3/anti-CD28 Dynabeads™ in appropriate amount of growth factor cytokines such as IL-2. The anti-CD3 antibody provides a TCR mimic activation signal whereas the anti-CD28 provides a costimulatory signal required for enhanced proliferation of T cells. The magnetic beads coated with anti-CD3/anti-CD28 are used to allow easy separation prior infusion of anti-tumor cells into the patient.

The isolated PBMCs are incubated with anti-CD3/anti-CD28 Dynabeads™ for a period sufficient for enrichment of entire T cells population. In one embodiment, the PBMCs are incubated with the anti-CD3/anti-CD28 Dynabeads™ for 36-48 hours. The strength of antigen stimulus determines the activation status of T cells required for transducing with lentiviral particles. The ratio of PBMCs: Dynabeads impact the activation status of T cells and ratios 1:1, 2:1, 3:1 are known in art for generation of chimeric antigen receptor T cells. In one embodiment, the ratio of PBMCs: Dynabeads was adjusted to 1:1 for specific period of incubation as described herein.

The activated T cells are transduced with lentiviral particles encoding the humanized anti-CD19 CAR using techniques known in the prior art. The transduced T cells are analyzed for expression and stable integration of humanized anti-CD19 CAR using flow cytometry. The humanized anti-CD19 CAR expressing T cells are expanded into clinically meaningful numbers using T cell culture media along with serum and other growth factors like IL-2, IL-7, and IL-15 prior to infusion. In one embodiment, the humanized anti-CD19 CAR expressing T cells are expanded for more than a week prior to cryopreservation. The cryopreservation of T cells can be performed by techniques known in art using cryoprotectants like DMSO. The generated humanized anti-CD19 CAR T cells are assessed preclinically for their anti-tumor efficacy using effector and target co-culture method and cytokines assay. The detail description of preclinical assessment is described in example section.

3. Method of Treatment

T cells expressing a CAR molecule of the present invention are capable of killing cancer cells. CAR-expressing T cells may either be created ex vivo either from a patient's own peripheral blood ($1^{st}$ party), or in the setting of a hematopoietic stem cell transplant from donor peripheral blood ($2^{nd}$ party), or peripheral blood from an unconnected donor ($3^{rd}$ party). Alternatively, CAR T-cells may be derived from ex-vivo differentiation of inducible progenitor cells or embryonic progenitor cells to T-cells. In these instances, CAR T-cells are generated by introducing DNA coding for the CAR by one of many means including transduction with a viral vector, transfection with DNA.

T cells expressing a CAR molecule of the present invention may be used for the treatment of a cancerous disease, in particular a cancerous disease associated with CD19 expression.

A method for the treatment of disease relates to the therapeutic use of a vector or T cell of the invention. In this respect, the vector or T cell may be administered to a subject having an existing disease or condition in order to lessen, reduce or improve at least one symptom associated with the disease and/or to slow down, reduce or block the progression of the disease.

In certain aspects, the invention pertains to provide immune response to the patient affected with CD19 associated using humanized anti-CD19 CAR described herein. In one aspect, the humanized anti-CD19 CAR is expressed by T cells, which provide the anti-tumor response.

The invention pertains to treatment of CD19 associated disease preferably B cell malignancies using cells expressing the humanized anti-CD19 CAR. The disease associated with CD19 expression is selected from a proliferative disease, such as a cancer or malignancy or a precancerous conditions such as a myelodysplasia, a myelodysplastic syndrome or a preleukemia, or is a non-cancer related indication associated with expression of CD19. In a preferred embodiment, the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In another embodiment, the cancer of B-cell origin is selected from the group consisting of B-lineage acute lymphoblastic leukemia, B-cell chronic lymphocytic leukemia, and B-cell non-Hodgkin's lymphoma including other CD19 positive malignancies.

EXAMPLES

Example 1: Humanization of Murine FMC63 scFv

The present inventors developed 2nd generation anti-CD19 binding domain containing FRs and CDRs identified based on Kabat numbering amino acid annotation.

A humanized antibody can be produced using a variety of techniques known in the art, including but not limited to, CDR-grafting, verneering or resurfacing, chain shuffling, etc.

Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions.

Figure 6:
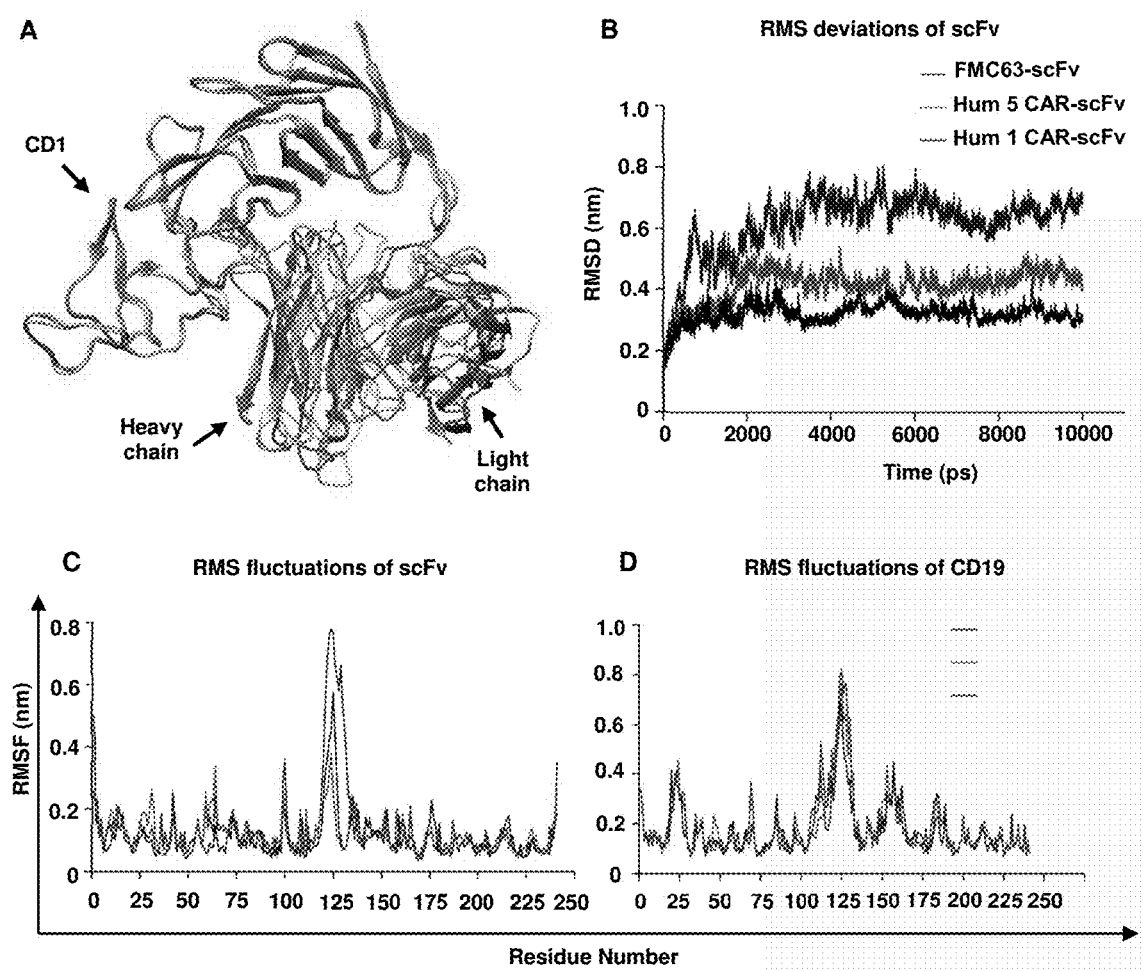
FIG. 6: Humanized scFv establishes higher binding affinity and flexibility with CD19 antigen compared to FMC63 scFv. (A) Overlapped docked structures of CD19 and scFvs (CD19-FMC63: cyan, CD19-hum 1 CAR: purple, and CD19-hum 5 CAR: orange (B) Root mean square deviations (RMSD) of CD19-scFv complexes. The CD19-FMC63-scFv: black color, CD19-hum 1 CAR-scFv: blue color, and CD19-hum 5 CAR-scFv complex: red color. The RMSD of CD19-FMC63 scFv and CD19-hum 5 CAR scFv is stabilized within 3-4 Å, whereas the CD19-hum 1 CAR scFv shows higher fluctuations. (C) Root mean square fluctuations (RMSF) of Ca atoms of all three scFvs (FMC63 scFv: black color, hum 1 CAR scFv: blue color and hum 5 CAR scFv: red color) in complexes with CD19 antigen. (D) RMSF of the CD19 protein only (color codes are similar to C) in complex with all three scFvs. Higher RMSF value indicates the high flexibility while the constrained regions show low RMSF value. Hum 1 CAR denotes Humanized anti-CD19-41BB CAR and Hum 5 CAR denotes Humanized 5 anti-CD19-41BB CAR.

Humanized Anti-CD19 Binding Domain:

The method for generating humanized anti-CD19 CAR according to the present invention with surface expression of CAR majorly comprises humanization of the murine FMC63 mAb derived ScFv (Nicholson et al., 1997). The method involves following steps:

1. Sequence analysis of murine FMC63mAb derived scFv: FRs and CDRs were identified based on Kabat numbering amino acid annotation.
2. Collection of acceptor framework sequences: Acceptor framework sequences were collected from human germline Vbase database (http://www2.mrc-lmb.cam.ac.uk/yb base-intro2.php) (Retter, Althaus, Munch, & Muller, 2005). Based on best fit with donor amino acids (FMC63 scFv), VH4_34 and VK1_O18 sequences were chosen for heavy and light chain respectively. Next human J elements JH6 and JK4 were taken for heavy chain and light chain respectively (Table 1-6).
3. Sequence analysis of acceptor framework: FRs and CDRs were identified based on Kabat numbering amino acid annotation.
4. Replacement of CDRs of acceptor framework: CDRs of acceptor framework replaced with CDRs of FMC63 scFv.
5. Structural analysis: Structural models of humanized scFv were predicted by I-TASSER. Total five models were predicted and most stable model was selected based on C score closest to zero. Critical interacting residues were identified by Pymol. VH #24, #25, #70-72, #66-70, #77-83 were critical interacting residues of acceptor framework of CDRs of heavy chain. Four residues VH #25, #70, #69, #78 were supposed to maintain the structural integrity so they were retained from the mouse framework (FMC63 scFv).
6. Sequence modification (Mutagenesis): It is identified that humanization as well as CDR modifications give optimal binding affinity to the CAR upon binding to CD19 antigen. These modifications affect the binding affinity and flexibility of scFv upon binding with CD19 target protein (FIG. 6).

Table 1 and 2 shows the similarity of heavy and light chain variable regions of human germline sequences available in Vbase database with murine FMC63 heavy and light chain variable regions.

TABLE 1

| Heavy chain human germline sequences of Vbase database | % identity with FMC63 heavy chain |
| --- | --- |
| VH3-13 | 47 |
| VH3-53 | 51 |
| VH3-66 | 51 |
| VH4-34 | 56 |
| VH4-4 | 53 |

TABLE 2

| Light chain human germline sequence of Vbase database | % identity with FMC63 heavy chain |
| --- | --- |
| VK1-O12 | 73% |
| VK1-O18 | 73% |
| VK1-A30 | 67% |
| VK1-L14 | 66% |
| VK1-L1 | 51% |
| VK1-L15 | 71% |
| VK1-L18 | 70% |
| VK1-L5 | 71% |
| VK1-L8 | 69% |
| VK1-L23 | 68% |
| VK1-L9 | 69% |
| VK1-L11 | 68% |
| VK3-L2 | 57% |
| VK3-L6 | 58% |
| VK5-B2 | 52% |
| VK6-A10 | 57% |
| VK6-A14 | 61% |
| VK1-A20 | 73% |
| VK1-L12 | 69% |
| VK3-L20 | 59% |
| VK1-L24 | 69% |

Tables 3 and 4 shows the similarity of framework 4 region (FR4) of human heavy and light chain variable regions with murine FMC63 respectively.

TABLE 3

| Heavy chain FR4 sequences of human germilneVbase database | % identity with FMC63 FR4 region |
|---|---|
| JH1 | 91 |
| JH3 | 91 |
| JH6 | 91 |

TABLE 4

| Light chain FR4 sequences of human germilneVbase database | % identity with FMC63 FR4 region |
|---|---|
| JL2 | 100 |

Table 5: Table below describes the amino acid sequence of humanized regions and CDR regions in heavy chain of humanized anti-CD19 CAR. Unique regions are highlighted in bold and underlined, FMC63 heavy chain is identified by SEQ ID No. 65, Humanized 1 heavy chain is identified by SEQ ID No. 1. Humanized 2 heavy chain is identified by SEQ ID No. 2.

TABLE 5

Tables below describes the amino acid sequence of humanized regions and CDR regions in heavy chain of humized anti-CD-19 CAR. Unique regions are highlighted in bold and underlined. FMC63 heavy chain is identified by SEQ ID NO: 65, Humanized 1 heavy chain is identified by SEQ ID NO: 1, Humanized 2 heavy chain is identified by SEQ ID NO: 2.

Heavy Chain

| Kabat number | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| FMC63 heavy chain | E | V | K | L | Q | E | S | G | P | G | L | V | A | P | S | Q | S | L |
| Humanized 1 heavy chain | Q | V | Q | L | Q | Q | W | G | A | G | L | L | K | P | S | E | T | L |
| Humamized 2 heavy chain | Q | V | Q | L | Q | Q | W | G | A | G | L | L | K | P | S | E | T | L |

| Kabat number | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|
| | | | | | | | | CDR H1 | | | | | | | | | |
| FMC63 heavy chain | S | V | T | C | T | V | S | G | V | S | L | P | Y | G | V | S | |
| Humanized 1 heavy chain | S | L | T | C | A | V | S | G | V | S | L | P | Y | G | V | S | |
| Humanized 2 heavy chain | S | L | T | C | A | V | Y | G | V | S | L | P | Y | G | V | S | |

| | 36 | 37 | 38 | 39 | 40 | 41 | 42 | 43 | 44 | 45 | 46 | 47 | 48 | 49 |
|---|---|---|---|---|---|---|---|---|---|---|---|---|---|---|
| FMC63 heavy chain | W | I | R | Q | P | P | R | K | G | L | E | W | L | G |
| Humamized 1 heavy chain | W | I | R | Q | P | P | G | K | G | L | E | W | L | G |
| Humamized 2 heavy chain | W | I | R | Q | P | P | G | K | G | L | E | W | L | G |

| | 50 | 51 | 52 | 53 | 54 | 55 | 56 | 57 | 58 | 59 | 60 | 61 | 62 | 63 | 64 | 65 | 66 | 67 | 68 |
|---|---|---|---|---|---|---|---|---|---|---|---|---|---|---|---|---|---|---|---|
| | | | | | | | | CDR H2 | | | | | | | | | | | |
| FMC63 heavy chain | V | I | W | G | S | E | T | T | Y | Y | N | S | A | L | K | S | R | L | T |
| Humanized 1 heavy chain | V | I | W | G | S | E | T | T | Y | Y | S | S | S | L | K | S | - | V | T |
| Humanized 2 heavy chain | V | I | W | G | S | E | T | T | Y | Y | S | S | S | L | K | S | - | V | T |

| | 69 | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|
| FMC63 heavy chain | I | I | K | D | N | S | K | S | Q | V | F | L | K | M | N |
| Humanized 1 heavy chain | I | I | K | D | T | S | K | N | Q | F | F | L | K | L | S |

TABLE 5-continued

Tables below describes the amino acid sequence of humanized regions and CDR regions in heavy chain of humized anti-CD-19 CAR. Unique regions are highlighted in bold and underlined. FMC63 heavy chain is identified by SEQ ID NO: 65, Humanized 1 heavy chain is identified by SEQ ID NO: 1, Humanized 2 heavy chain is identified by SEQ ID NO: 2.

Heavy Chain

| | | | | | | | | | | | | | | |
|---|---|---|---|---|---|---|---|---|---|---|---|---|---|---|
| Humanized 2 heavy chain | I | _S_ | _V_ | D | T | S | K | N | Q | F | _S_ | L | K | L | S |

| | 82b | 82c | 83 | 84 | 85 | 86 | 87 | 88 | 89 | 90 | 91 | 92 | 93 | 94 |
|---|---|---|---|---|---|---|---|---|---|---|---|---|---|---|
| FMC63 heavy chain | S | L | Q | T | D | D | T | A | I | Y | Y | C | A | K |
| Humanized 1 heavy chain | S | V | T | A | A | D | T | A | V | Y | Y | C | A | R |
| Humanized 2 heavy chain | S | V | T | A | A | D | T | A | V | Y | Y | C | A | R |

| | 95 | 96 | 97 | 98 | 99 | 100 | 100a | 100b | 100c | 100d | 101 | 102 |
|---|---|---|---|---|---|---|---|---|---|---|---|---|
| FMC63 heavy chain | H | Y | Y | Y | G | G | S | Y | A | M | D | Y |
| | | | | | | CDR H3 | | | | | | |
| Humamized 1 heavy chain | H | Y | Y | Y | G | G | S | Y | A | M | D | Y |
| Humamized 2 heavy chain | H | Y | Y | Y | G | G | S | Y | A | M | D | Y |

| | 103 | 104 | 105 | 106 | 107 | 108 | 109 | 110 | 111 | 112 | 113 |
|---|---|---|---|---|---|---|---|---|---|---|---|
| FMC63 heavy chain | W | G | Q | G | T | S | V | T | V | S | S |
| Humanized 1 heavy chain | W | G | Q | G | T | T | V | T | V | S | S |
| Humanized 2 heavy chain | W | G | Q | G | T | T | V | T | V | S | S |

Table 6: Table below describes the amino acid sequence of humanized regions and CDR regions in light chain of humanized anti-CD19 CAR. Unique regions are highlighted in bold and underlined, FMC63 light chain is identified by SEQ ID No. 66. Both Humanized 1 light chain and Humanized 2 light chain are identified by SEQ ID No. 3.

TABLE 6

Table below described the amino acid sequence of humanized regions and CDR regions in light chain of humanized anti-CD19 CAR. Unique regions are highlighted in bold and underlined. FMC63 light chain is identified by SEQ ID NO: 66, Both Humanized 1 light chain and Humanized 2 light 2 light chain are identified by SEQ ID NO: 3.

Light Chain

| Kabat number | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| FMC63 Light chain | D | I | Q | M | T | Q | T | T | S | S | L | S | A | S | L | G | D | R |
| Humamized 1 Light chain | D | I | Q | M | T | Q | S | P | S | S | L | S | A | S | V | G | D | R |
| Humamized 2 Light chain | D | I | Q | M | T | Q | S | P | S | S | L | S | A | S | V | G | D | R |

| Kabat number | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|
| | | | | | | CDR L1 | | | | | | | | | | |
| FMC63 Light chain | V | T | I | S | C | R | A | S | Q | D | I | S | K | Y | L | N |
| Humanized 1 Light chain | V | T | I | I | C | R | A | S | Q | D | I | S | K | Y | L | N |
| Humanized 2 Light chain | V | T | I | I | C | R | A | S | Q | D | I | S | K | Y | L | N |

TABLE 6-continued

Table below described the amino acid sequence of humanized regions and CDR regions in light chain of humanized anti-CD19 CAR. Unique regions are highlighted in bold and underlined. FMC63 light chain is identified by SEQ ID NO: 66, Both Humanized 1 light chain and Humanized 2 light 2 light chain are identified by SEQ ID NO: 3.

Light Chain

| | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|
| FMC63 Light chain | W | Y | Q | Q | K | P | D | G | T | V | - | L | L | I | Y |
| Humanized 1 Light chain | W | Y | Q | Q | K | P | G | K | A | P | K | L | L | I | Y |
| Humanized 2 Light chain | W | Y | Q | Q | K | P | G | K | A | P | K | L | L | I | Y |

| | 50 | 51 | 52 | 53 | 54 | 55 | 56 | 57 | 58 | 59 | 60 | 61 | 62 |
|---|---|---|---|---|---|---|---|---|---|---|---|---|---|
| | | | CDR L2 | | | | | | | | | | |
| FMC63 Light chain | H | T | S | R | L | H | S | G | V | P | S | R | F |
| Humanized 1 Light chain | H | T | S | R | L | H | S | G | V | P | S | R | F |
| Humanized 2 Light chain | H | T | S | R | L | H | S | G | V | P | S | R | F |

| | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|
| FMC63 Light chain | S | G | S | G | S | G | T | D | Y | S | L | T | I | S | N | L | E |
| Humanized 1 Light chain | S | G | S | G | S | G | T | D | F | T | F | T | I | S | S | L | Q |
| Humanized 2 Light chain | S | G | S | G | S | G | T | D | F | T | F | T | I | S | S | L | Q |

| | 80 | 81 | 82 | 83 | 84 | 85 | 86 | 87 | 88 | 89 | 90 | 91 | 92 | 93 | 94 | 95 | 96 | 97 |
|---|---|---|---|---|---|---|---|---|---|---|---|---|---|---|---|---|---|---|
| | | | | | | | | | | | | CDR L3 | | | | | | |
| FMC63 Light chain | Q | E | D | I | A | T | Y | F | C | Q | Q | G | N | T | L | P | Y | T |
| Humanized 1 Light chain | P | E | D | I | A | T | Y | Y | C | Q | Q | G | N | T | L | P | Y | T |
| Humanized 2 Light chain | P | E | D | I | A | T | Y | Y | C | Q | Q | G | N | T | L | P | Y | T |

| | 98 | 99 | 100 | 101 | 102 | 103 | 104 | 105 | 106 | 106A | 107 | 108 | 109 |
|---|---|---|---|---|---|---|---|---|---|---|---|---|---|
| FMC63 Light chain | F | G | G | G | T | K | L | E | I | T | R | A | D |
| Humanized 1 Light chain | I | G | G | G | T | K | V | E | I | K | | | |
| Humanized 2 Light chain | I | G | G | G | T | K | V | E | I | K | | | |

Example 2: Product Design of Humanized Anti-CD19 CARs According to the Present Invention According to the present invention five different humanized anti-CD19 CARs were designed (FIG. 1). Their scFv domains were adapted from murine clone FMC63 and humanized by the method mentioned in example 1. In the process of humanization, the complementarity determining region (CDRs) from the murine monoclonal antibody FMC63 are maintained as such, or modified to get optimal binding affinity. The variable framework region (FRs) is selected from human origin HV4_34 and may further include the modification VH4_34 (I to L) to get optimal binding affinity.

In humanized 1 and 2, leader peptide, hinge and transmembrane domain taken from human CD8α receptor (UniProtKB-P01732). Signaling domain of 4-1BB (CD137) (UniProtKB-Q07011) used as a co-stimulatory domain. CD3 zeta (UniProtKB-P20963) used as a signaling domain.

In humanized 3 and 4 anti-CD19-41BB CAR, leader peptide and hinge domain taken from human CD8α receptor (UniProtKB-P01732). 4-1BB (CD137) (UniProtKB-Q07011 used as both transmembrane domain and co-stimulatory domain. CD3 zeta (UniProtKB-P20963) used as a signaling domain.

These humanized anti-CD19CAR constructs were chemically synthesized by GeneArt (Life Technologies) after codon optimization and cloned into pHIV-EGFP lentiviral transfer plasmid.

Example 3: Gene Optimization and Selection of Promoter

Efficacy of anti-CD19 CAR T cells critically depends on the CAR expression on T cell surface, which is regulated by many factors including "species" specific codon usage in nucleotide sequence and selection of promoter under which CAR is expressed. Gene optimization was performed by multi-parametric Gene-Optimizer tool which deals with the different sequence related parameters such as transcription, splicing, stability and translation to achieve higher gene expression and performance in the expression system.

1. Gene Optimization:
   (1) The codon usage was adapted to the codon bias of *Homo sapiens* genes.
   (2) Regions of very high (>80%) or very low (<30%) GC content have been avoided where possible.
   (3) During the optimization process the following cis-acting sequence motifs were avoided where applicable:
       Internal TATA-boxes, chi-sites and ribosomal entry sites
       AT-rich or GC-rich sequence stretches
       RNA instability motifs
       Repeat sequences and RNA secondary structures
       (Cryptic) splice donor and acceptor sites in higher eukaryotes
       Average GC content: 57%

2. Expression of CAR Construct Under EF1a Promoter in $3^{rd}$ Generation Lentiviral Vector System:

The anti-CD19 CAR constructs according to the present invention were expressed under EF1alpha promoter. This promoter increases the expression of anti-CD19 CAR gene on CAR T cell surface.

In addition $3^{rd}$ generation lentiviral vector system was used to generate the lentivirus gene delivery vehicle. According to the literature $3^{rd}$ generation lentivirus system is safer in clinic compared to second generation lentiviral vector system and retroviral vector system.

Example 3: Production of Humanized Anti-CD19 CAR Gene Delivery Vehicle (Lentiviral Vector)

Lentiviral particles carrying humanized anti-CD19 CAR gene were generated and used for transducing T cells. To produce lentiviral particles, Lenti-X 293T packaging cells (clontech, USA) were seeded for overnight in T-75 flasks (Corning) in lentiviral packaging medium (LPM) at 37° C. Next day these cells were transfected with above CAR plasmid along with packaging plasmid pMDLg/pRRE (Addgene reference number-12251), pRSV-REV (Addgene reference number-12253) and envelop plasmid pMD2G (Addgene reference number-12259) with lipofectamine 3000 (Life technologies, USA). Post 6 hr media was replaced with fresh LPM and incubated for next 18 hr. Media containing viral supernatant was collected and again fresh media was added into the flask. Collected virus supernatant was centrifuged at 2000 rpm for 5 min to remove cell debris and then filtered with 0.45 µm PVDF filter (Merck Millipore). Filtered viral supernatant was transferred into the open top polypropylene tube of SW32 Ti (Beckman, USA) clean autoclaved polyallomer tube (38 ml tube). Ultracentrifugation was done at 24200 rpm for 2 hr at 4° C. Virus pellet was re-suspended by pipetting as well as vortexing in appropriate volume of 1×HBSS (Hanks' Balanced Salt Solution, Thermo scientific) and incubated at 4 degree for overnight. Again re-suspended virus supernatant was spin down at 14000 rpm (max speed) for 1 min at 4 degree to pellet down the cell debris if any. Supernatant containing humanized anti-CD19 CAR carrying lentiviral particles was collected and stored at −80° C. in the aliquots.

Example 4: Generation of T Cell Expressing Humanized Anti-CD19 CAR and its Efficacy Study This example demonstrates the methods of generating T cells expressing humanized anti-CD19 CAR.

Peripheral blood mononuclear cells (PBMCs) were isolated from healthy individual. Monocytes were depleted by adherence method for 1 hr incubation at 37° C. Non adherent cells were activated for 36-48 hr by anti-CD3/anti-CD28 magnetic beads (Life Technologies, USA) in 1:1 cell to bead ratio in 24 well plate (Corning, USA) with cell density 1 million cells per 2 ml of T cell media (AIM-V with 5% heat inactivated FBS; thermo scientific) supplemented with 50 ng/ml recombinant IL-2 (Life Technologies).

T Cell Transduction Using Retronectin Mediated Method:

Non tissue culture treated 24 well plate (Eppendorf) was coated with 5 ug/cm2 of Retronectin (Takara, Clontech, CA) diluted in 250 ul of 1× phosphate buffer saline (PBS). Plate was incubated for overnight at 4° C. Next day retronectin solution was aspirated and wells were blocked by 2% BSA in PBS for 30 min at RT. After incubation wells were washed once with 2.5% HEPES (Thermo scientific, USA) in 1×PBS.

Virus supernatant were rapidly thawed at 37° C. water bath and diluted with T cell media then added to retronectin coated wells keeping the multiplicity of infection (MOI) 2-10. Plate was incubated for 6 hr at 37° C. CO2 incubator. After incubation virus was aspirated and wells were washed with T cell media. 1 million activated PBMCs were re-suspended in 1 ml of T cell media supplemented with 100 ng/ml IL-2 and added into the virus bound well and incubated for next 24 hr. Post 24 hr transduction was repeated in fresh virus bound retronectin coated well followed by 24 hr incubation. After incubation cells were transferred into new tissue culture treated 6 well plate with 6 ml of T cell media supplemented with 50 ng/ml of IL-2 then further incubated for 48 hr.

T cell transduction using spinocultaion method: $1 \times 10^6$ activated cells were cultured in tissue culture treated 24-well plate and lentiviral particles were added (MOI: 1-10) along with protamine sulfate (20 ug/ml) and centrifuged for 2 h at 32 degree at 1000 g. After centrifugation plate were kept for 24 h in incubator (37 degree) with 5% CO2 in air. After 24 h, similar process was repeated. Next day, virus was removed and cells were expanded as required by maintaining the cell density (0.3 million per ml). Cell count and FACS analysis done post 48 hr after beads removal.

CAR surface expression was confirmed by Protein L (Genescript: Cat #M00097) staining as well as % GFP positive cells by flowcytometry. For Protein L staining, $1 \times 10^5$ cells were washed thrice in FACS staining buffer (2% FBS in 1×PBS). 1 µl of Protein L was added in the tube and incubated for 30 min on ice. After incubation cells were washed thrice with staining buffer. PE labeled streptavidin was added and incubated for 10 min on ice then washed twice with staining buffer and acquisition was performed by flowcytometry.

CAR receptor per cell was quantified by BD-Quantibrite beads assay kit. These quantibrite beads are bound with four levels of PE molecules. PE stained CAR T cells were analysed in flowcytometry using the same instrument settings after running the quantibrite beads and CAR receptor per cell identified using a standard curve. Humanized 1 anti-CD19-41BB CAR intensity falls in high PE population and 114896 receptor per cell was obtained.

These humanized anti-CD19 CAR modified T cells were used to check the killing of CD19 positive tumor cells. Following experiments showed that our indigenous anti CD19 CAR construct are potent killer of tumor cells:

(a) Cytotoxicity Assay: Co-Culture with Target Cells

Figure 3:
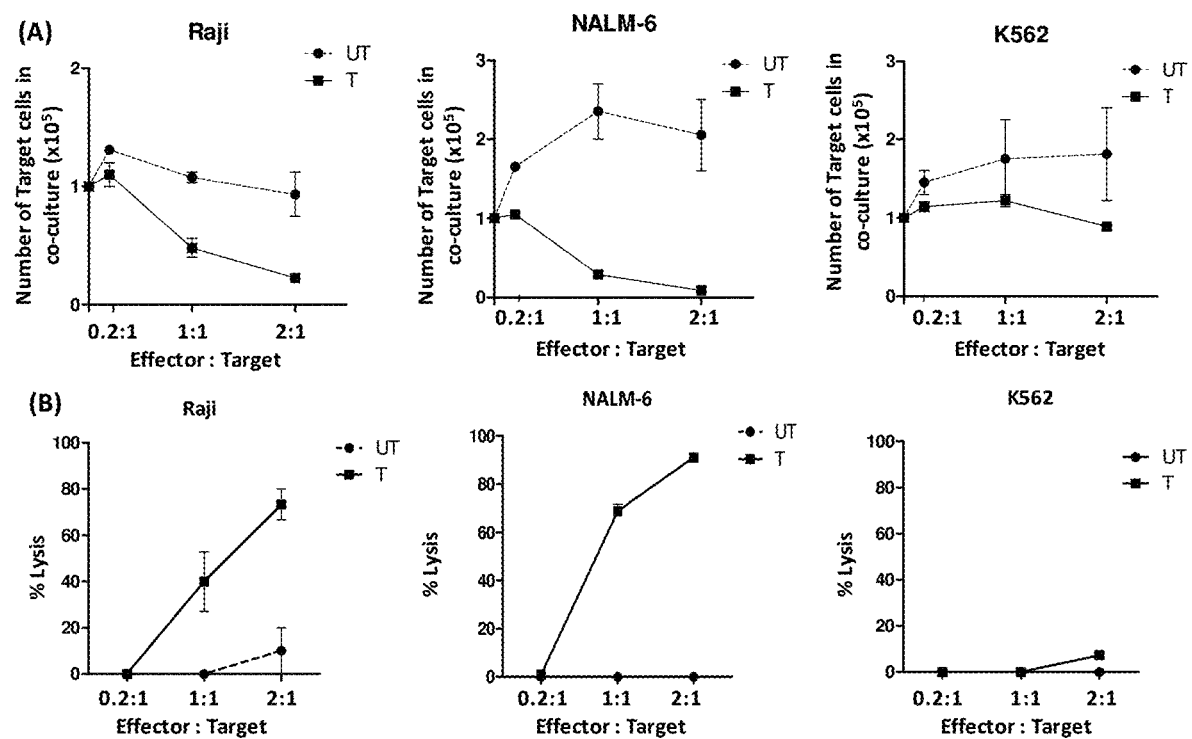
FIG. 3: Cytotoxicity mediated by T cells expressing humanized anti-CD19 Chimeric Antigen Receptor co-cultured in increasing Effector (CAR+T cells): Target (Tumor cells)
  (A) Analysis of proliferation of tumor cells in co-culture with humanized anti-CD19 Chimeric Antigen Receptor expressing T cells (T) compared to untransduced T cells (UT) with starting population as 1×105 target cells. Raji and Nalm-6 are the cell lines of B cell origin expressing CD19 antigen, whereas K562 cell line is negative for CD19 antigen.
  (B) Analysis of lysis/killing of tumor cells in co-culture with humanized anti CD19 Chimeric Antigen Receptor expressing T cells (T) compared to untransduced T cells (UT) determined by flowcytometry. Raji and Nalm-6 are the cell lines of B cell origin expressing CD19 antigen, whereas K562 cell line is negative for CD19 antigen.

Humanized anti-CD19 CAR T cells were co-cultured with CD19+ (Raji and NALM-6) and CD19 negative (K562) tumor cells in different E: T ratio. Proliferation of tumor cells were observed in co-cultured humanized anti-CD19 Chimeric Antigen Receptor expressing T cells (T) compared to untransduced T cells (UT) with starting population as $1\times10^5$ target cells (FIG. 3A). Percent lysis/killing of tumor cells in co-culture experiment was also shown with humanized anti CD19 CAR T cells (T) compared to untransduced T cells (UT) determined by flowcytometry (FIG. 3B).

(b) Cytokine Assay

Figure 4:
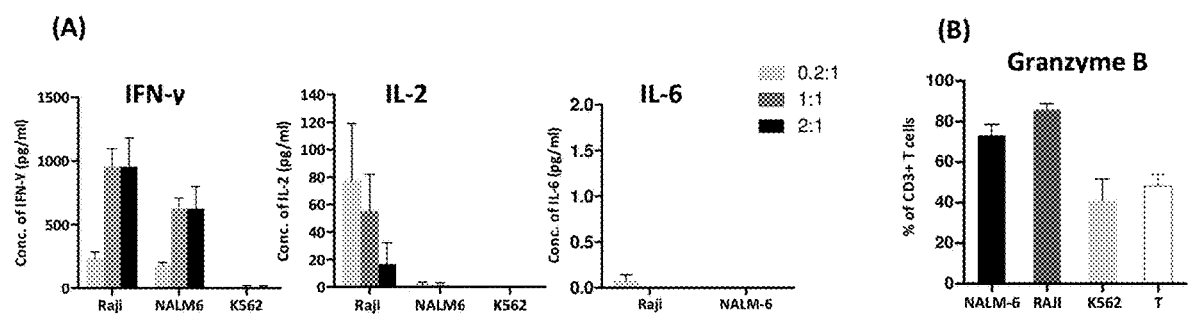
FIG. 4: Cytokine secretion by T cells expressing humanized anti-CD19 Chimeric Antigen Receptor upon incubation with target cells for 18-24 hours in different effector:target ratios.
  (A) Depicts the graphical representation of concentration of Interferon-gamma, Interleukin-2 and Interleukin-6 analyzed from supernatants of the co-culture experiment using ELISA respectively.
  (B) Represents the percentage granzyme B producing CD3 positive cells upon co-culture of effector cells with different target cells in 5:1 effector:target ratio by intracellular staining using flowcytometry.
Figure 5:
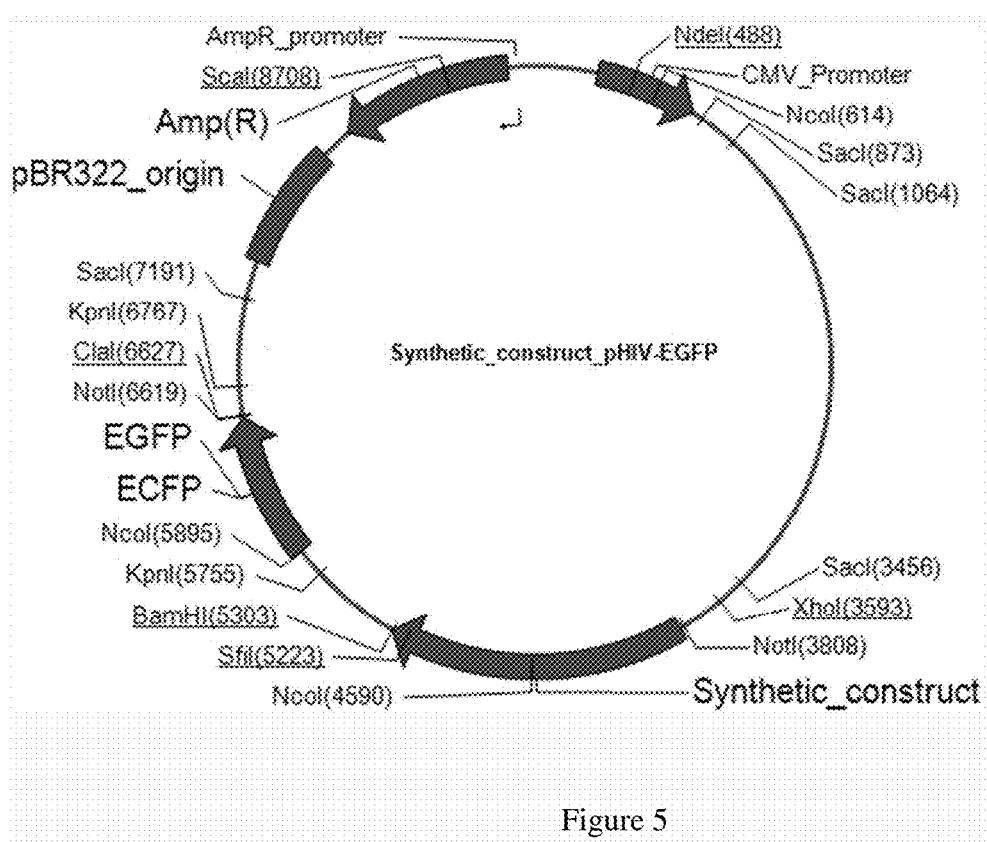
FIG. 5: pHIV-EGFP lentiviral vector under the EF1 alpha promoter for expression of humanized anti-CD19 CAR according to the present invention.

Immune effector cytokines such as IFN-gamma and IL-2 were checked by ELISA in 18 hrs culture supernatant upon co-culture of anti-CD19 CAR T cells with CD19 positive cells (Raji and NALM-6) and CD19 negative cells (K562). (FIGS. 4A and 4B). We have seen increase in IFN-gamma and IL-2 in transduced cells (CAR T cells) as compared to untransduced cells (only activated T cells no CAR surface expression) when co-cultured with CD19 positive cells and negligible cytokine were seen in CD19 negative cells.

(c) Granzyme B Assay

We have checked the percentage granzyme B producing CD3 positive cells upon co-culture of effector cells with different target cells (Raji, NALM-6 and K562) in 5:1 effector: target ratio by intracellular staining using flowcytometry and observed that there was significant increase in the CD3+ granzyme B compared to only transduced cells (T) post 18 hr of co-culture (FIG. 4C).

Example 5: Comparative Study Between Humanized Anti-CD19 CAR-T Cell According to the Present Invention and the Available Anti-CD19 CAR T Cell Therapy Developed by Prof. Carl June (CTL019)

The humanized anti-CD19 CAR-T cell according to the present invention differs from the available art at least with respect to the choice of frame work region, CDR region and presence of critical residues around CDRs, which have a major role in target recognition affinity and hence impacts the anti-tumor efficacy.

Following critical changes were made in scFv by the present inventors to increase the efficacy of the humanized anti-CD19 CAR-T cell according to the present invention:
1. Human frame work region were selected from Vbase database which have higher identity with amino acid sequence of frame work regions of donor FMC63 clone.
2. As the CDRs affect the binding affinity of CARs, grafting was done with or without any modification in the CDR sequences.
3. The vernier zones around CDRs containing critical residues which majorly impacts 3D confirmation and affinity towards antigen were identified and changed to its conserved amino acids from FMC63 to in order to maintain its affinity.
4. The orientation VH and VL domain of the humanized anti-CD 19 binding domain according to the present invention also have an impact on the anti-tumor efficacy.

These major changes in humanized scFv are absent in comparable CAR available in prior art, hence making indigenous humanized CAR a novel drug with enhanced efficacy and not a mere alternative. Along with these changes, the other changes above have led to improvement of efficacy of indigenously developed humanized CAR T cells. The improvement in anti-tumor efficacy can be highlighted by following two characteristics of the CARs.

1. Cytotoxicity Against CD19+ Malignancies:

The anti-tumor efficacy of humanized CAR T cells is analyzed by co-culture experiment of anti-CD19 CAR T cells with CD19 expressing tumor cells. It can be observed that humanized CAR according to the present invention shows 80-90% tumor efficacy in CD19+ Nalm-6 and Raji cells in 2:1 E:T ratio, whereas a comparable efficacy is observed in Prof. Carl June's humanized CAR T cells at 10:1 E: T (US20140271635). One of the reasons of high efficacy of anti-CD19 CAR T cells is the high anti-CD19 CAR receptor per cell expression (~150000) on CAR T cells. Therefore, it can be inferred that indigenous humanized CAR T cells are more potent anti-tumor cells compared to available humanized CAR. It has to be noted that Prof. Carl June's humanized CAR has been tested on genetically engineered CD19 expressing K562 cell line. The present experimental design involves use of CD19 expressing Nalm-6 and CD19 expressing Raji cells which are cell lines derived from acute lymphoblastic leukemia (ALL) and Burkitt's lymphoma origin respectively. These cell lines are better representative of the patient population for which CAR T cells have been approved by FDA as a therapeutic drug.

2. Cytokine Profile:

Upon antigen encounter the T cells secrete various cytokines, which severe as growth factors for the T cells and also a few cytotoxic molecules against antigen expressing target cells. The higher levels of cytokines can also be a risk factor in CAR T cell therapy as it can hyper activate the immune system leading to potential side effects known as cytokine release syndrome as reported in many clinical trials.

Prof. Carl June's humanized CAR T cells cytokine profile was compared with indigenous humanized CAR T according to the present invention in the ratios with 80-90% efficacy. It was observed that cytokine secretion in Humanized indigenous CAR T according to the present invention showed ~4 fold less IFN-gamma as compared to Humanized CAR T cells (US20140271635).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

We claim:

1. A recombinant nucleic acid molecule encoding a humanized chimeric antigen receptor (CAR), wherein the humanized CAR comprises:

(a) a single chain antibody or single chain antibody fragments comprising a humanized anti-CD 19 binding domain;

(b) a hinge region wherein said hinge region comprises the nucleic acid sequences of SEQ ID No. 38;

(c) a transmembrane domain wherein said transmembrane domain comprises the nucleotide sequence selected from SEQ ID No. 39, SEQ ID No. 40 and SEQ ID No. 45; and (d) a cytoplasmic domain comprising a human 4-1BB costimulatory signaling domain wherein said costimulatory signaling domain comprises the nucleotide sequence selected from SEQ ID No. 41 and SEQ ID No. 47 and a CD33 signaling domain wherein said signaling domain comprises the nucleotide sequence selected from SEQ ID No. 42, SEQ ID No. 48 and SEQ ID No. 49;

wherein said humanized anti-CD 19 binding domain is scFv and comprises a heavy chain framework region 1 (HFR1) of SEQ ID No: 4 or SEQ ID No: 5, a heavy chain framework region 2 (HFR2) of SEQ ID No: 7, a heavy chain framework region 3 (HFR3) of SEQ ID No: 9 or SEQ ID No: 10, a heavy chain framework region 4 (HFR4) of SEQ ID No: 12 and a light chain framework region 1 (LFR1) of SEQ ID No: 13, a light chain framework region 2 (LFR2) of SEQ ID No: 15, a light chain framework region 3 (LFR3) of SEQ ID No: 17 and a light chain framework region 4 (LFR4) of SEQ ID No: 19;

wherein said nucleic acid molecule encodes a heavy chain complementary determining region 1 (HC CDR1) of SEQ ID No: 6, a heavy chain complementary determining region 2 (HC CDR2) of SEQ ID No: 8, a heavy chain complementary determining region 3 (HC CDR3) of SEQ ID No: 11 and a light chain complementary determining region 1 (LC CDR1) of SEQ ID No: 14, a light chain complementary determining region 2 (LC CDR2) of SEQ ID No: 16, and a light chain complementary determining region 3 (LC CDR3) of SEQ ID No: 18.

2. The nucleic acid molecule as claimed in claim 1, which encodes a heavy chain variable region (HCVR) selected from SEQ ID No: 1 and SEQ ID No: 2 and a light chain variable region (LCVR) of SEQ ID No: 3.

3. The nucleic acid molecule as claimed in claim 1, which comprises a nucleic acid sequences encoding the HCVR and the LCVR, wherein the nucleic acid sequence encoding the HCVR comprises the nucleotide sequence selected from SEQ ID No. 35 and SEQ ID No. 36, or nucleotide sequence with at least 95% identity thereof, and the nucleic acid sequence encoding the LCVR comprises the nucleotide sequence selected from SEQ ID No. 37, SEQ ID No. 50 and SEQ ID No. 51, or nucleotide sequence with at least 95% identity thereof.

4. The nucleic acid molecule as claimed in claim 1, wherein the encoded HCVR is attached to the encoded LCVR via a linker comprising an amino acid sequence of SEQ ID No. 20.

5. The nucleic acid molecule as claimed claim 4, which comprises a nucleic acid sequences encoding the linker, wherein the nucleic acid sequence encoding the linker comprises the nucleotide sequence selected from SEQ ID No. 43 and SEQ ID No. 46, or a nucleotide sequence with at least 95% identity thereof.

6. The nucleic acid molecule as claimed in claim 1, wherein the encoded transmembrane domain comprises the amino acid sequence selected from SEQ ID No. 21 and SEQ ID No. 29.

7. The nucleic acid molecule as claimed in claim 1, wherein the encoded anti-CD 19 binding domain is connected to the transmembrane domain by the hinge region comprising the amino acid sequences of SEQ ID No. 22.

8. The nucleic acid molecule as claimed in claim 1, wherein the encoded costimulatory domain comprises the amino acid sequence of SEQ ID No. 23.

9. The nucleic acid molecule as claimed in claim 1, wherein the encoded signaling domain comprises the amino acid sequence of SEQ ID No. 24.

10. The nucleic acid molecule as claimed in claim 1, wherein the encoded humanized CAR further comprises a leader sequence comprising the amino acid sequences of SEQ ID No. 30.

11. The nucleic acid molecule as claimed claim 10, which comprises a nucleic acid sequences encoding the leader sequence, wherein the nucleic acid sequence encoding the leader sequence comprises the nucleotide sequence selected from SEQ ID No. 31 and SEQ ID No. 44, or a nucleotide sequence with at least 95% identity thereof.

12. The nucleic acid molecule as claimed in claim 1, wherein it comprises a nucleic acid sequence optimized for human codon usage and selected from SEQ ID No. 26, SEQ ID No. 28, SEQ ID No. 34, SEQ ID No. 53, and SEQ ID No. 62, or a nucleotide sequence with at least 95% identity thereof.

13. A vector comprising the nucleic acid molecule as claimed in claim 1 which comprises the nucleotide sequence selected from SEQ ID No. 54, SEQ ID No. 55, SEQ ID No. 56 and SEQ ID No. 57, or nucleotide sequence with at least 95% identity thereof.

14. An immune cell comprising the vector according to claim 13 wherein the immune cell is a human T lymphocyte including but not restricted to CD8+ and CD4+T lymphocyte and its possible subsets.

15. A pharmaceutical composition comprising the nucleic acid molecule according to claim 1 or the vector according to claim 13 or the cell according to claim 14, with a pharmaceutically acceptable carrier, diluent or excipient, and optionally one or more further pharmaceutically active polypeptides and/or compounds.

16. A recombinant nucleic acid molecule encoding a humanized chimeric antigen receptor (CAR), wherein the humanized CAR comprises:
  (a) a single chain antibody or single chain antibody fragments comprising a humanized anti-CD 19 binding domain;
  (b) a hinge region wherein said hinge region comprises the nucleic acid sequences of SEQ ID No. 38;
  (c) a transmembrane domain wherein said transmembrane domain comprises the nucleotide sequence selected from SEQ ID No. 39, SEQ ID No. 40 and SEQ ID No. 45; and
  (d) a cytoplasmic domain comprising a human 4-1BB costimulatory signaling domain wherein said costimulatory signaling domain comprises the nucleotide sequence selected from SEQ ID No. 41 and SEQ ID No. 47 and a CD35 signaling domain wherein said signaling domain comprises the nucleotide sequence selected from SEQ ID No. 42, SEQ ID No. 48 and SEQ ID No. 49;
  wherein said humanized anti-CD 19 binding domain is scFv and comprises a heavy chain framework region 1 (HFR1) of SEQ ID No: 4 or SEQ ID No: 5, a heavy chain framework region 2 (HFR2) of SEQ ID No: 7, a heavy chain framework region 3 (HFR3) of SEQ ID No: 9 or SEQ ID No: 10, a heavy chain framework region 4 (HFR4) of SEQ ID No: 12 and a light chain framework region 1 (LFR1) of SEQ ID No: 13, a light chain framework region 2 (LFR2) of SEQ ID No: 15, a light chain framework region 3 (LFR3) of SEQ ID No: 17 and a light chain framework region 4 (LFR4) of SEQ ID No: 19;
  wherein said nucleic acid molecule encodes a heavy chain variable region (HCVR) selected from SEQ ID No: 1 and SEQ ID No: 2 and a light chain variable region (LCVR) of SEQ ID No: 3.

\* \* \* \* \*